US012569274B2

(12) United States Patent
Sorajja et al.

(10) Patent No.: US 12,569,274 B2
(45) Date of Patent: Mar. 10, 2026

(54) METHOD AND APPARATUS FOR REMOVING HEART VALVE THERAPY

(71) Applicant: AMX Technologies, LLC, Plymouth, MN (US)

(72) Inventors: Paul Sorajja, Plymouth, MN (US); David M. Costello, Plymouth, MN (US); Daniel P. Coyle, Plymouth, MN (US); Karl Alexander Kabarowski, Plymouth, MN (US); Alex Alden Peterson, Plymouth, MN (US)

(73) Assignee: AMX Technologies, LLC, Plymouth, MN (US)

( * ) Notice: Subject to any disclaimer, the term of this patent is extended or adjusted under 35 U.S.C. 154(b) by 740 days.

(21) Appl. No.: 17/597,011

(22) PCT Filed: Jul. 8, 2020

(86) PCT No.: PCT/US2020/041206
§ 371 (c)(1),
(2) Date: Dec. 22, 2021

(87) PCT Pub. No.: WO2021/007324
PCT Pub. Date: Jan. 14, 2021

(65) Prior Publication Data
US 2022/0265311 A1 Aug. 25, 2022

Related U.S. Application Data

(60) Provisional application No. 62/977,021, filed on Feb. 14, 2020, provisional application No. 62/872,139, filed on Jul. 9, 2019.

(51) Int. Cl.
*A61B 17/3207* (2006.01)
*A61B 17/00* (2006.01)
(Continued)

(52) U.S. Cl.
CPC .. *A61B 17/320783* (2013.01); *A61B 18/1492* (2013.01); *A61F 2/2466* (2013.01);
(Continued)

(58) Field of Classification Search
CPC .............. A61B 17/221; A61B 17/3205; A61B 2017/2212; A61B 2018/141
See application file for complete search history.

(56) References Cited

U.S. PATENT DOCUMENTS 4,493,320 A 1/1985 Treat
5,190,542 A * 3/1993 Nakao .............. A61B 17/32056
606/49
(Continued)

FOREIGN PATENT DOCUMENTS

EP 2326264 B1 11/2017
EP 3471628 B8 4/2021
(Continued)

OTHER PUBLICATIONS

Khan, J.M. et al., "Transcatheter Mitral Valve Replacement After Transcatheter Electrosurgical Laceration of Alfieri STItCh (Elastic)," *JACC: Cardiovascular Interventions*, vol. 11, No. 8, 2018, Elsevier on Behalf of The American College of Cardiology Foundation, Apr. 23, 2018, pp. 808-811.
(Continued)

*Primary Examiner* — Ronald Hupczey, Jr.
(74) *Attorney, Agent, or Firm* — Inskeep IP Group, Inc.

(57) ABSTRACT
A retrieval catheter and methods of use are described for removing a heart valve therapy such as a leaflet clip or artificial leaflet cord. The retrieval catheter can include a cutting element and a basket, piercing element, clamping mechanism, or similar grasping device. The method includes delivering a catheter to the region of the heart valve therapy and then manipulating the catheter and associated instru-
(Continued)

ments to cut tissue as necessary and then remove the heart valve therapy and withdraw the catheter.

32 Claims, 48 Drawing Sheets

(51) Int. Cl.
| | |
|---|---|
| *A61B 17/22* | (2006.01) |
| *A61B 17/221* | (2006.01) |
| *A61B 18/14* | (2006.01) |
| *A61F 2/24* | (2006.01) |

(52) U.S. Cl.
CPC .................. *A61B 2017/003* (2013.01); *A61B 2017/22097* (2013.01); *A61B 17/221* (2013.01)

(56) References Cited

U.S. PATENT DOCUMENTS

| | | | |
|---|---|---|---|
| 5,417,697 | A | 5/1995 | Wilk et al. |
| 5,465,731 | A * | 11/1995 | Bell ................. A61B 17/00234 |
| | | | 600/562 |
| 5,673,695 | A | 10/1997 | McGee et al. |
| 5,735,289 | A | 4/1998 | Pfeffer et al. |
| 5,741,271 | A | 4/1998 | Nakao et al. |
| 5,759,187 | A * | 6/1998 | Nakao .................... A61B 1/018 |
| | | | 606/113 |
| 6,050,995 | A * | 4/2000 | Durgin ................... A61B 18/14 |
| | | | 606/50 |
| 7,367,975 | B2 | 5/2008 | Malecki et al. |
| 7,618,437 | B2 | 11/2009 | Nakao |
| 7,815,676 | B2 | 10/2010 | Greenberg |
| 8,142,443 | B2 | 3/2012 | Saleh |
| 8,579,964 | B2 | 11/2013 | Lane et al. |
| 9,572,666 | B2 | 2/2017 | Basude et al. |
| 9,770,256 | B2 | 9/2017 | Cohen et al. |
| 10,624,664 | B2 | 4/2020 | Cohen |
| 10,667,804 | B2 | 6/2020 | Basude et al. |
| 10,736,632 | B2 | 8/2020 | Khairkhahan |
| 11,071,562 | B2 | 7/2021 | Joseph |
| 11,071,564 | B2 | 7/2021 | Prabhu |
| 11,337,775 | B2 | 5/2022 | Wang |
| 11,602,367 | B2 | 3/2023 | Cohen |
| 11,653,947 | B2 | 5/2023 | Prabhu |
| 11,963,712 | B2 | 4/2024 | De Marchena |
| 2002/0013571 | A1 | 1/2002 | Goldfarb et al. |
| 2002/0123761 | A1 | 9/2002 | Barbut et al. |
| 2003/0120341 | A1* | 6/2003 | Shennib ............... A61B 5/0215 |
| | | | 623/2.12 |
| 2004/0059345 | A1 | 3/2004 | Nakao et al. |
| 2007/0016225 | A1 | 1/2007 | Nakao |
| 2007/0287999 | A1 | 12/2007 | Malecki et al. |
| 2008/0015409 | A1 | 1/2008 | Barlow et al. |
| 2008/0039881 | A1 | 2/2008 | Greenberg |
| 2008/0103508 | A1 | 5/2008 | Karakurum |
| 2009/0209955 | A1 | 8/2009 | Forster et al. |
| 2010/0036375 | A1 | 2/2010 | Regadas |
| 2010/0268226 | A1 | 10/2010 | Epp et al. |
| 2013/0006262 | A1 | 1/2013 | Lampropoulos et al. |
| 2014/0046320 | A1 | 2/2014 | Kappel et al. |
| 2014/0155924 | A1 | 6/2014 | McDonald |
| 2014/0276810 | A1 | 9/2014 | Raybin et al. |
| 2015/0038988 | A1 | 2/2015 | Tegels et al. |
| 2015/0045788 | A1* | 2/2015 | Litscher ........... A61B 17/12104 |
| | | | 606/41 |
| 2015/0066015 | A1 | 3/2015 | Miles et al. |
| 2015/0157401 | A1 | 6/2015 | Falwell et al. |
| 2015/0257883 | A1 | 9/2015 | Basude et al. |
| 2016/0174956 | A1* | 6/2016 | Ciulla ................. A61B 17/221 |
| | | | 606/1 |
| 2016/0206426 | A1 | 7/2016 | Khoynezhad et al. |
| 2016/0213919 | A1 | 7/2016 | Suwito et al. |
| 2017/0105743 | A1 | 4/2017 | Vale et al. |
| 2018/0008268 | A1 | 1/2018 | Khairkhahan |
| 2018/0092661 | A1 | 4/2018 | Prabhu |
| 2019/0183571 | A1* | 6/2019 | De Marchena .. A61B 17/22031 |
| 2020/0001053 | A1 | 1/2020 | Rafiee |
| 2020/0061340 | A1 | 2/2020 | Mixter et al. |
| 2020/0121460 | A1 | 4/2020 | Dale et al. |
| 2020/0245998 | A1 | 8/2020 | Basude et al. |
| 2020/0289196 | A1* | 9/2020 | Arevalos ........ A61B 17/320016 |
| 2020/0323528 | A1 | 10/2020 | Khairkhahan |
| 2020/0345493 | A1 | 11/2020 | Gregg et al. |
| 2020/0352694 | A1 | 11/2020 | Bak-Boychuk et al. |
| 2021/0137579 | A1 | 5/2021 | Rafiee et al. |
| 2021/0212756 | A1 | 7/2021 | Rafiee |
| 2021/0330355 | A1 | 10/2021 | Leung et al. |
| 2021/0401434 | A1 | 12/2021 | Tien et al. |
| 2022/0000544 | A1 | 1/2022 | Rafiee et al. |
| 2022/0008096 | A1 | 1/2022 | Prabhu |
| 2022/0054185 | A1 | 2/2022 | Rafiee et al. |
| 2022/0054186 | A1 | 2/2022 | Rafiee et al. |
| 2022/0079754 | A1 | 3/2022 | Mei et al. |
| 2022/0111193 | A1 | 4/2022 | Geddie et al. |
| 2022/0265311 | A1 | 8/2022 | Sorajja et al. |
| 2022/0323148 | A1 | 10/2022 | Rothstein et al. |
| 2022/0361907 | A1 | 11/2022 | Osterbauer et al. |
| 2023/0000609 | A1 | 1/2023 | Wood et al. |
| 2023/0248956 | A1 | 8/2023 | Eidenschink et al. |
| 2023/0380900 | A1 | 11/2023 | De Marchena |
| 2023/0380973 | A1 | 11/2023 | De Marchena et al. |
| 2023/0404758 | A1 | 12/2023 | Tennenbaum et al. |
| 2023/0414357 | A1 | 12/2023 | Costello et al. |

FOREIGN PATENT DOCUMENTS

| | | | |
|---|---|---|---|
| EP | 3996608 | A1 | 5/2022 |
| JP | 2002-524112 | A | 8/2002 |
| JP | 5483125 | B2 | 5/2014 |
| WO | WO 1995/010318 | A1 | 4/1995 |
| WO | WO 2000/013192 | A1 | 3/2000 |
| WO | WO 2010/014515 | A2 | 2/2010 |
| WO | WO 2010/014515 | A3 | 2/2010 |
| WO | WO 2010/118064 | A1 | 10/2010 |
| WO | WO 2014/151869 | A1 | 9/2014 |
| WO | WO 2015/031898 | A2 | 3/2015 |
| WO | WO 2017/095689 | A1 | 6/2017 |
| WO | WO 2021/007324 | A1 | 1/2021 |
| WO | WO 2021/092576 | A1 | 5/2021 |
| WO | WO 2022/056317 | A1 | 3/2022 |
| WO | WO 2022/066621 | A1 | 3/2022 |
| WO | WO 2023/137497 | A3 | 7/2023 |
| WO | WO 2023/215908 | A2 | 11/2023 |

OTHER PUBLICATIONS

WIPO, U.S. International Search Authority, International Search Report and Written Opinion mailed Sep. 30, 2020 in International Patent Application No. PCT/US2020/041206, 11 pages.

European Patent Office, Extended European Search Report dated Jun. 15, 2023 in European Patent Application No. 20837883.6, 8 pages.

European Patent Office, Communication pursuant to Article 94(3) EPC dated Oct. 9, 2024 in European Patent Application No. 20837883.6, 8 pages.

European Patent Office, Extended European Search Report dated Sep. 23, 2024 in European Patent Application No. 21873270.9, 9 pages.

WIPO, U.S. International Search Authority, Re-Published Application with International Search Report mailed Jan. 18, 2024 in International Patent Application No. PCT/US2023/06671, 4 pages.

WIPO, U.S. International Search Authority, International Search Report and Written Opinion mailed Dec. 12, 2023 in International Patent Application No. PCT/US2023/06671, 15 pages.

WIPO, U.S. International Search Authority, International Search Report and Written Opinion mailed Jul. 24, 2023 in International Patent Application No. PCT/US2023/060773, 12 pages.

WIPO, U.S. International Search Authority, International Search Report and Written Opinion mailed Feb. 2, 2022 in International Patent Application No. PCT/US/2021/051258, 12 pages.

(56) References Cited

OTHER PUBLICATIONS

WIPO, U.S. International Search Authority, International Search Report and Written Opinion mailed Mar. 7, 2025 in International Patent Application No. PCT/US2024/057855, 18 pages.

Japan Patent Office, Office Action dated May 7, 2025 with English translation in Japanese Patent Application No. 2023-517942, 8 pages.

China National Intellectual Property Administration, Office Action dated Mar. 21, 2025 with English translation in Chinese Patent Application No. 202080050018.6, 11 pages.

WIPO, U.S. International Search Authority, Invitation to Pay Additional Fees and, Where Applicable, Protest Fee mailed Apr. 10, 2025 in International Patent Application No. PCT/US2025/016897, 2 pages.

Japan Patent Office, Office Action dated Jun. 3, 2025 with English translation in Japanese Patent Application No. 2022-501174, 13 pages.

WIPO, U.S. International Search Authority, International Search Report and Written Opinion mailed Jun. 9, 2025 in International Patent Application No. PCT/US2025/016897, 18 pages.

Capps, S. et al., "Body surface area as a predictor of aortic and pulmonary valve diameter," *The Journal of Thoracic Cardiovascular Surgery*, vol. 119, Issue 5, URL: https://www.jtcvs.org/article/S0022-5223(00)70092-4/fulltext, May 2000, pp. 975-982.

European Patent Office, Extended European Search Report dated Nov. 17, 2025 in European Patent Application No. 23740912.3, 10 pages.

Japan Patent Office, Decision of Refusal dated Nov. 25, 2025 in Japanese Patent Application Serial No. 2022-501174 with English translation, 15 pages.

* cited by examiner 104B          104A          104C

104

104B

104C

104A 104B   104A

104C

104A

104B

104C

104A 104B     104C

104A 104B    104C

104D

104A 104B    104C

104D

104D

104B

104A

104C 104C    104A

104D

104B

104A 104B    104C

104D

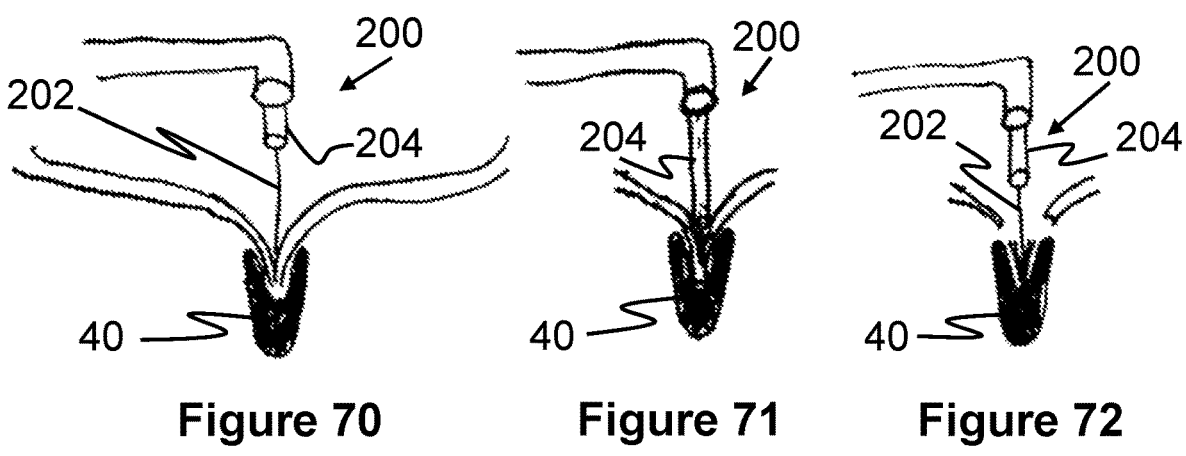
Figure 70 Figure 71 Figure 72
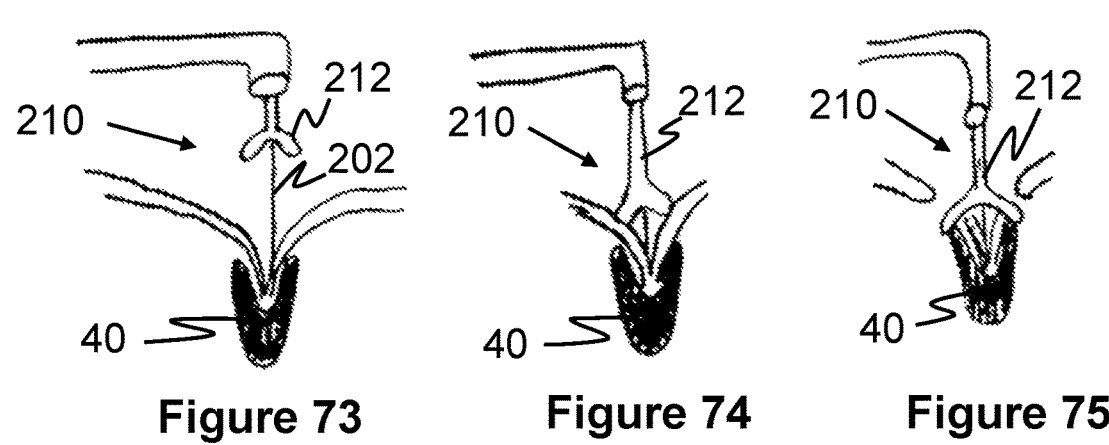
Figure 73 Figure 74 Figure 75
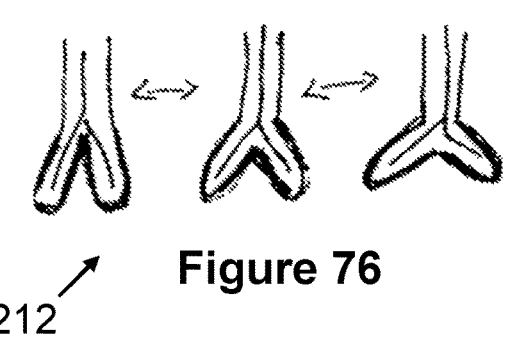
Figure 76

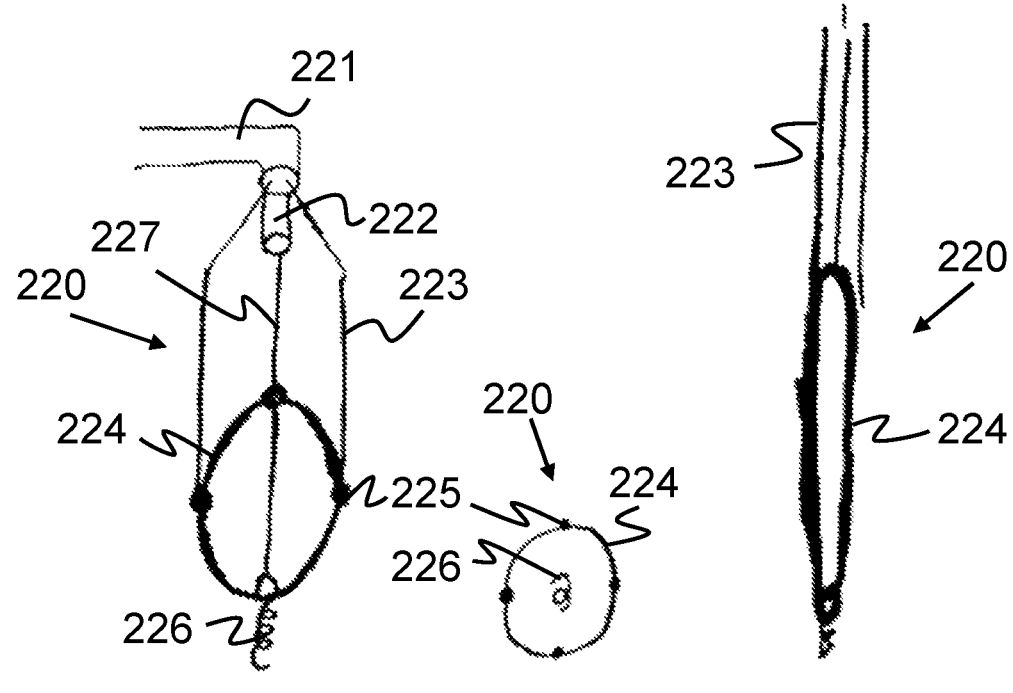
Figure 77     Figure 78     Figure 79
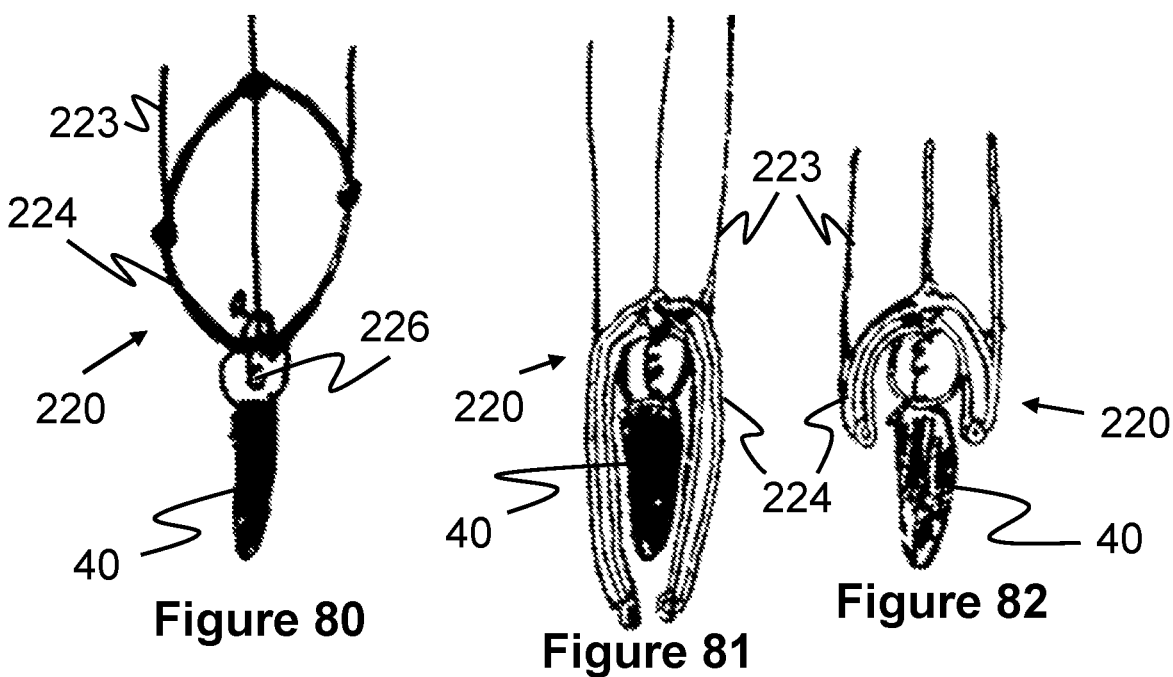
Figure 80     Figure 81     Figure 82

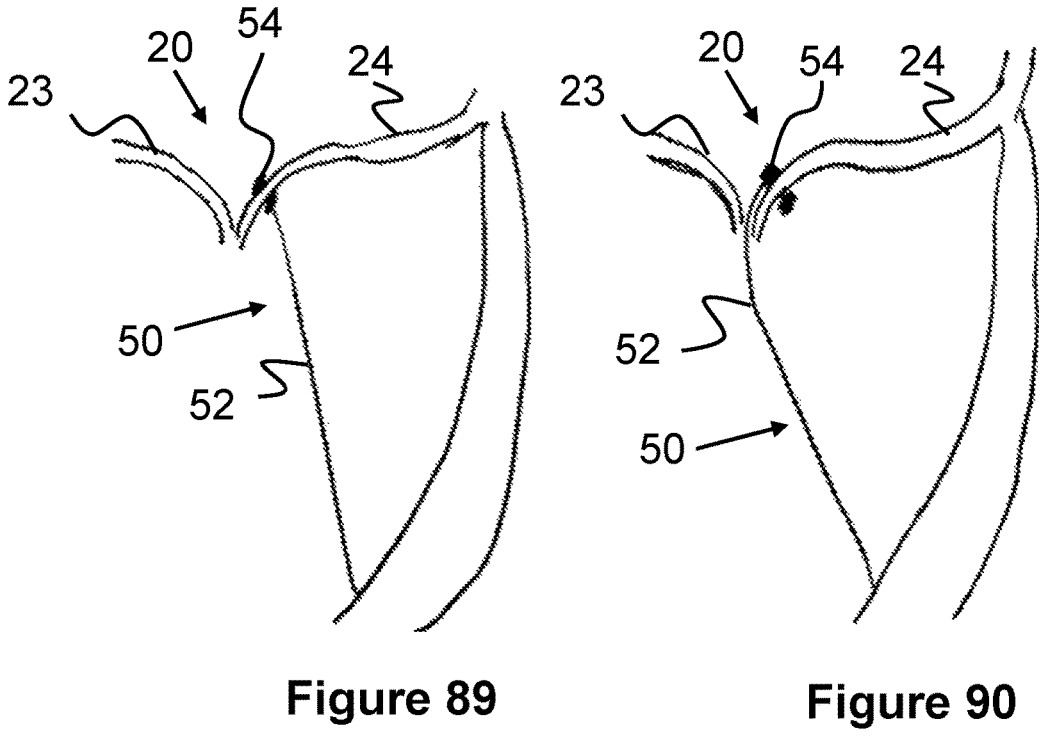
Figure 89          Figure 90
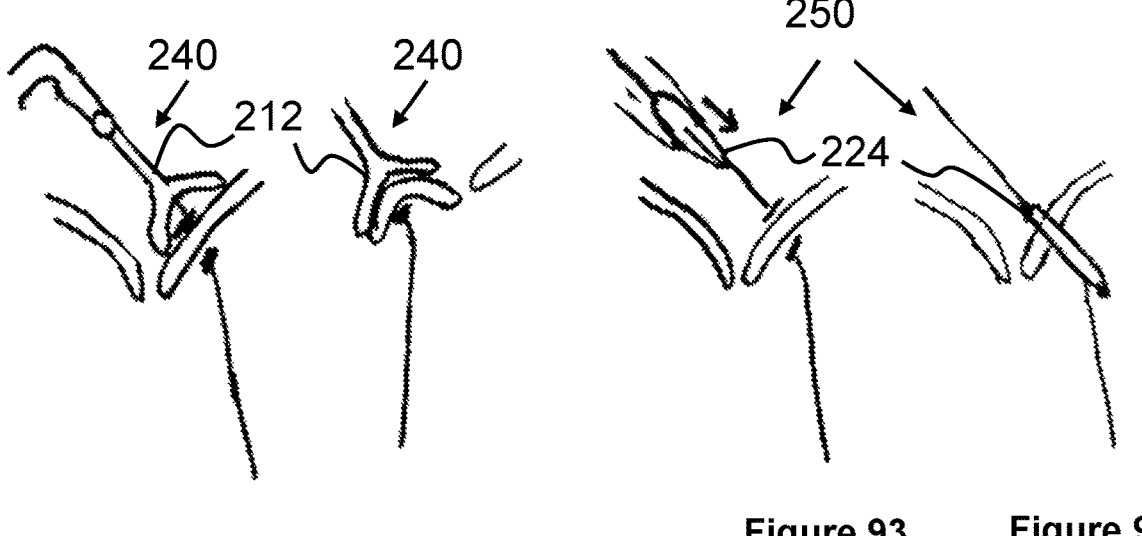
Figure 91    Figure 92          Figure 93    Figure 94

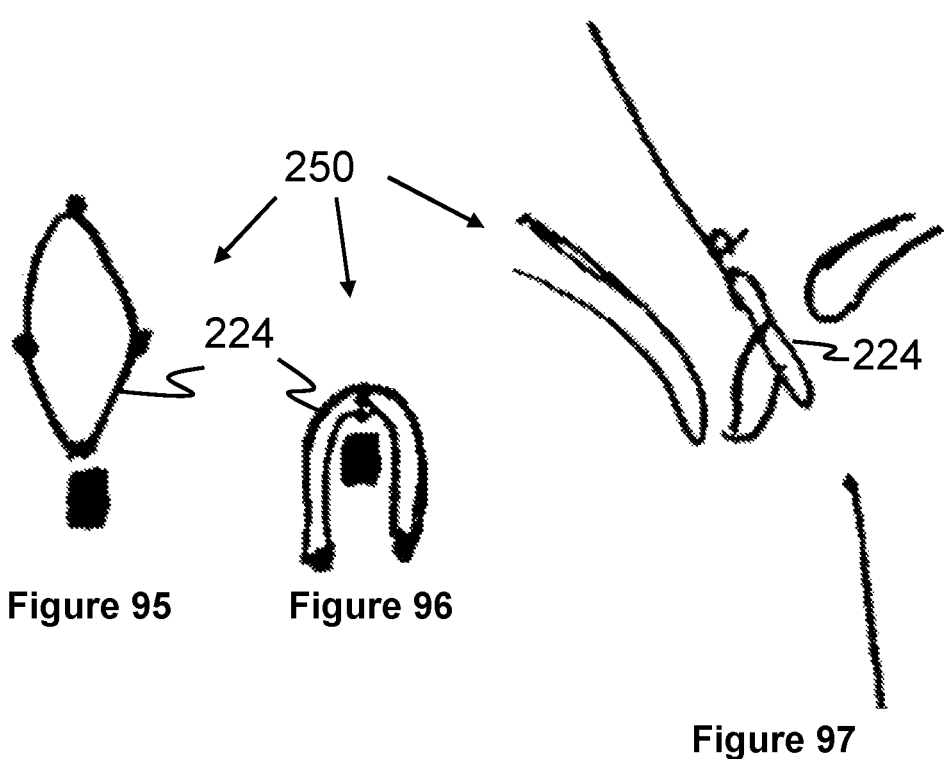
Figure 95      Figure 96
Figure 97
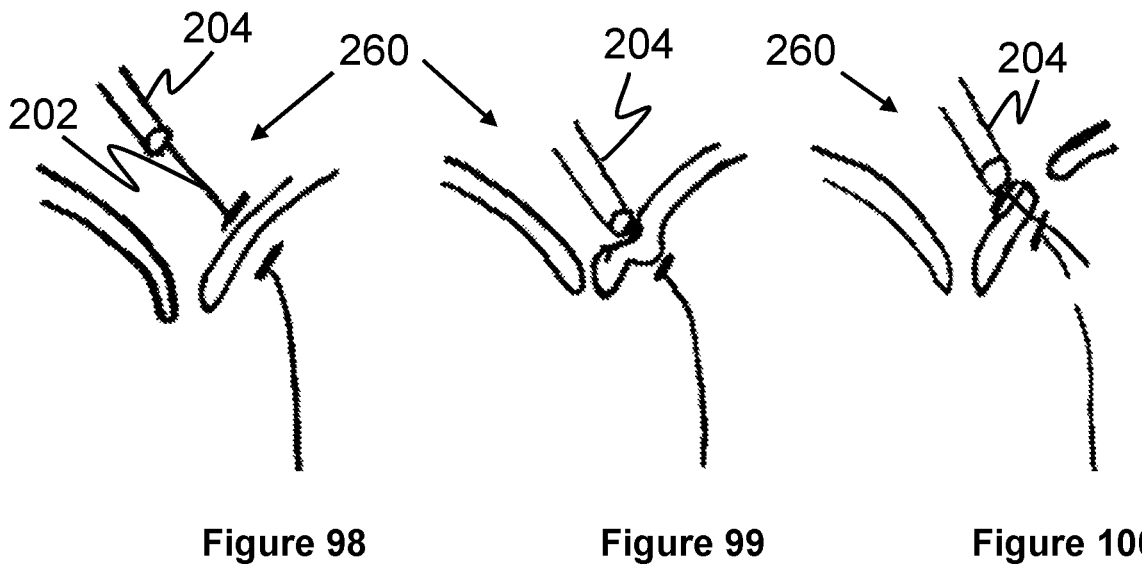
Figure 98      Figure 99      Figure 100

316

380

METHOD AND APPARATUS FOR REMOVING HEART VALVE THERAPY

RELATED APPLICATIONS

This application is the U.S. National Phase of and claims priority to International Patent Application No. PCT/US2020/041206, International Filing Date Jul. 8, 2020, entitled Method And Apparatus For Removing Heart Valve Therapy; which claims benefit of U.S. Patent Application Ser. No. 62/977,021 filed Feb. 14, 2020 entitled Method And Apparatus For Removing Heart Valve Therapy, and which claims benefit of U.S. Patent Application Ser. No. 62/872,139 filed Jul. 9, 2019 entitled Method And Apparatus For Removing Heart Valve Therapy, all of which are incorporated herein by reference in their entireties.

FIELD OF THE INVENTION

The present disclosure relates to novel and advantageous transcatheter devices and methods to facilitate valvular repair and/or replacement. More specifically, the devices and methods herein relate to the removal of therapies which interact with heart valve leaflets.

BACKGROUND OF THE INVENTION

Heart valve conditions can occur when the leaflets of a patient's valve are unable to fully close, which allows blood to regurgitate or abnormally flow backward. Referring to FIG. 1, regurgitation is especially common with the mitral valve 20 in which the mitral valve anterior leaflet 22 fails to properly coapt with the posterior leaflet 24. As the ventricles of the heart 10 contract, some blood moves from the left ventricle 14, back into the left atrium 12 instead of into the aorta 11. Similar regurgitation may also occur with the tricuspid valve 15, allowing blood to flow from the right ventricle 13 back into the right atrium 16.

A common treatment for valvular regurgitation is the use of treatment devices that appose or permanently connect the leaflets together. This heart valve therapy hardware may have been placed using surgical, transcatheter, or minimally-invasive means. For example, the hardware or therapy targeted for removal may be the MitraClip (Abbott Structural, Santa Clara, Calif.), the PASCAL device (Edwards Lifesciences, Irvine, Calif.), a suture placed surgically (e.g., Alfieri stitch), or similar heart valve therapy. Other heart valve therapy may be the result of techniques that have involved the leaflets as part of a therapeutic target, and the part or whole leaflet involvement requires removal. Other examples include chordal replacement technologies placed with either transcatheter methods or surgery to compensate for improper length, disruption, or mispositioning of existing chords. For purposes of the present application, the phrase "heart valve therapy" shall be defined as any devices and/or methods used for therapeutic treatment of a heart valve, such as leaflet clips, sutures, artificial chords, or any other devices or methods associated with the treatment of heart valves and associated leaflets.

FIG. 2 illustrates an example transcatheter delivery procedure for a valve clip 40 (e.g., a MitraClip) to treat a regurgitating mitral valve 20. A delivery catheter 41 is advanced through the right atrium 16, through the atrial septum 18, and into the left atrium 12. As seen best in FIG. 3, an inner portion of the catheter 41A including a valve clip 40, is advanced through the mitral valve 20 and into the left ventricle 14. In the present example, the leaflet clip 40 includes two outer arms 40A positioned underneath the leaflets 22, 24, and two inner arms 40B positioned vertically between the two leaflets 22, 24. As seen in FIG. 3, the catheter 41 includes control wires that can cause the outer arms 40A to close against the inner arms 40B to pinch or engage the tissue of the leaflets. Barbs or similar structures on the arms 40B help the leaflet clip 40 to anchor within the tissue of the leaflets 22, 24, as seen in FIG. 4. Finally, the catheter 41 is removed, as seen in FIG. 5. As seen in the top view of FIG. 6, the leaflet clip 40 is typically positioned near a center of the valve 20, preventing the center portion from opening and creating two smaller valve openings on either side of the clip 40. The smaller diameter of these openings typically allows the leaflets to better coapt and prevent regurgitation.

In some instances, these structures need to be removed in order to facilitate other valvular therapy, such as when there is recurrent or residual regurgitation that needs to be addressed. For example, the valve may require placement of other leaflet technologies, annuloplasty or rings, chordae or cords, positioning devices, or a replacement valve, many of which may not be usable with heart valve therapy previously performed.

In some instances, these therapies need to be removed from one or more attachment points on the leaflets, but not completely in order to facilitate other valvular therapy, leaving the structure in the heart but able to move it from the area of interest and apply desired therapy.

However, these heart valve therapies are typically removed via open heart surgery, which can be particularly traumatic for patients and presents a relatively high risk of complications. Therefore, what is needed is a less traumatic approach to removing heart valve therapy that presents a lower risk of complications.

SUMMARY OF THE INVENTION

The present disclosure relates to systems and methods for removing heart valve therapies that have been used to position valve leaflets. This removal may be necessary when additional therapies for the treatment of valve disease are needed (e.g., different repair method, valve replacement), when the heart valve therapies have caused harm or the potential for harm to a patient (e.g., stenosis, infection), when the heart valve therapies have been deemed to not be of clinical benefit, or when there is a general desire to not have the therapy in place.

The present disclosure relates to systems and methods for removing heart valve therapies used to position leaflets, and this heart valve therapy may have been placed using surgical, transcatheter, or minimally-invasive means. In at least one embodiment, the hardware or therapy targeted for removal may be the MitraClip (Abbott Structural, Santa Clara, Calif.), the PASCAL device (Edwards Lifesciences, Irvine, Calif.), a suture placed surgically (e.g., Alfieri stitch), or similar positioning devices and techniques. In at least one embodiment, such positioning devices that need to be removed may be the result of techniques that have involved the leaflets as part of a therapeutic target, and the part or whole leaflet involvement requires removal. Examples of such devices are chordal replacement technologies placed with either transcatheter methods or surgery. In some instances, the cord or chords are not effective due to improper length, disruption, mispositioning, or defective prosthetic material.

A present method comprises a tool for cutting native valve tissue that has been attached to heart valve therapy with or without a capturing tool to hold the hardware to be removed while it is exteriorized from the human body. In at least one embodiment, the cutting method consists of an adjustable snare that envelops the heart valve therapy and can either cut the native tissue from the heart valve therapy mechanically, or by using a RF electrosurgical device that will heat tissue such that the electrosurgical cutting device's intracellular temperature rapidly reaches 100 degrees C., the intracellular contents undergo a liquid to gas conversion, massive volumetric expansion, and resulting vaporization. In at least one embodiment, the capturing tool is an adjustable basket, bag, or bin. This capturing tool can be used to cut, release, compress, modify, or fully retrieve the heart valve therapy from the human body.

In some embodiments, a method for removing previously placed heart valve therapy consists of a steerable catheter, which has been inserted into the patient using a transseptal, transatrial, or transventricular approach. The steerable catheter contains a delivery catheter that enables placement of the tools for cutting and for capturing the heart valve therapy.

In some embodiments, capture of the heart valve therapy is performed by insertion and embedding of a tool directly into, onto, and/or around the heart valve therapy. In this approach, the native tissue is cut from the heart valve therapy by the use of an electrosurgical cutting device (RF electrical or a similar device) or similar energy or force delivered from within the embedded tool. A basket or bag to capture the heart valve therapy may not be necessary for removal of the targeted material. Thus, in at least one embodiment, a cutting tool is used alone without the need for a capturing basket.

In at least one embodiment, a loop structure is pushed onto the tissue bridge, chordal implants, or method of fixation created by the heart valve therapy. The loop structure can be used to cut with either electrification or mechanical means. The loop structure may be circular, oval, or multi-segmented, and may completely or incompletely encapsulate the area for cutting and removal. The loop structure can be used to encircle the heart valve therapy and tissue for removal, followed by exteriorization.

In at least one embodiment, a tool is used to expand the heart valve therapy for removal. This expansion can be mechanical, electrical, pneumatic, hydraulic, or similar means in order to unfold or change the shape of heart valve therapy for its removal.

Elements of the tool can be fixated to the heart valve therapy to reduce the risk of embolization. This fixation can be accomplished by anchors that are straight, helical, barbed, or a combination of these approaches.

In at least one embodiment, a catheter, spacer, balloon, or other device could be used in conjunction with the removal device to manage the blood flow or regurgitation of the valve post removal of the heart valve therapy. This could be performed quickly if the removed heart valve therapy and basket could be retracted through the steerable catheter—then this sealing device could be delivered through the same delivery catheter.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 70 illustrates a side view of a removal catheter procedure according to the present invention.

FIG. 71 illustrates a side view of a removal catheter procedure according to the present invention.

FIG. 72 illustrates a side view of a removal catheter procedure according to the present invention.

FIG. 73 illustrates a side view of a removal catheter procedure according to the present invention.

FIG. 74 illustrates a side view of a removal catheter procedure according to the present invention.

FIG. 75 illustrates a side view of a removal catheter procedure according to the present invention.

FIG. 76 illustrates a side view of a removal catheter procedure according to the present invention.

FIG. 77 illustrates a side view of a removal catheter procedure according to the present invention.

FIG. 78 illustrates a side view of a removal catheter procedure according to the present invention.

FIG. 79 illustrates a side view of a removal catheter procedure according to the present invention.

FIG. 80 illustrates a side view of a removal catheter procedure according to the present invention.

FIG. 81 illustrates a side view of a removal catheter procedure according to the present invention.

FIG. 82 illustrates a side view of a removal catheter procedure according to the present invention.

FIG. 84 illustrates a side view of a removal catheter procedure according to the present invention.

FIG. 85 illustrates a side view of a removal catheter procedure according to the present invention.

FIG. 86 illustrates a side view of a removal catheter procedure according to the present invention.

FIG. 87 illustrates a side view of a removal catheter procedure according to the present invention.

FIG. 89 illustrates a side view of a removal catheter procedure according to the present invention.

FIG. 90 illustrates a side view of a removal catheter procedure according to the present invention.

FIG. 91 illustrates a side view of a removal catheter procedure according to the present invention.

FIG. 92 illustrates a side view of a removal catheter procedure according to the present invention.

FIG. 93 illustrates a side view of a removal catheter procedure according to the present invention.

FIG. 94 illustrates a side view of a removal catheter procedure according to the present invention.

FIG. 95 illustrates a side view of a removal catheter procedure according to the present invention.

FIG. 96 illustrates a side view of a removal catheter procedure according to the present invention.

FIG. 97 illustrates a side view of a removal catheter procedure according to the present invention.

FIG. 98 illustrates a side view of a removal catheter procedure according to the present invention.

FIG. 99 illustrates a side view of a removal catheter procedure according to the present invention.

FIG. 100 illustrates a side view of a removal catheter procedure according to the present invention.

DESCRIPTION OF EMBODIMENTS

Figure 1:
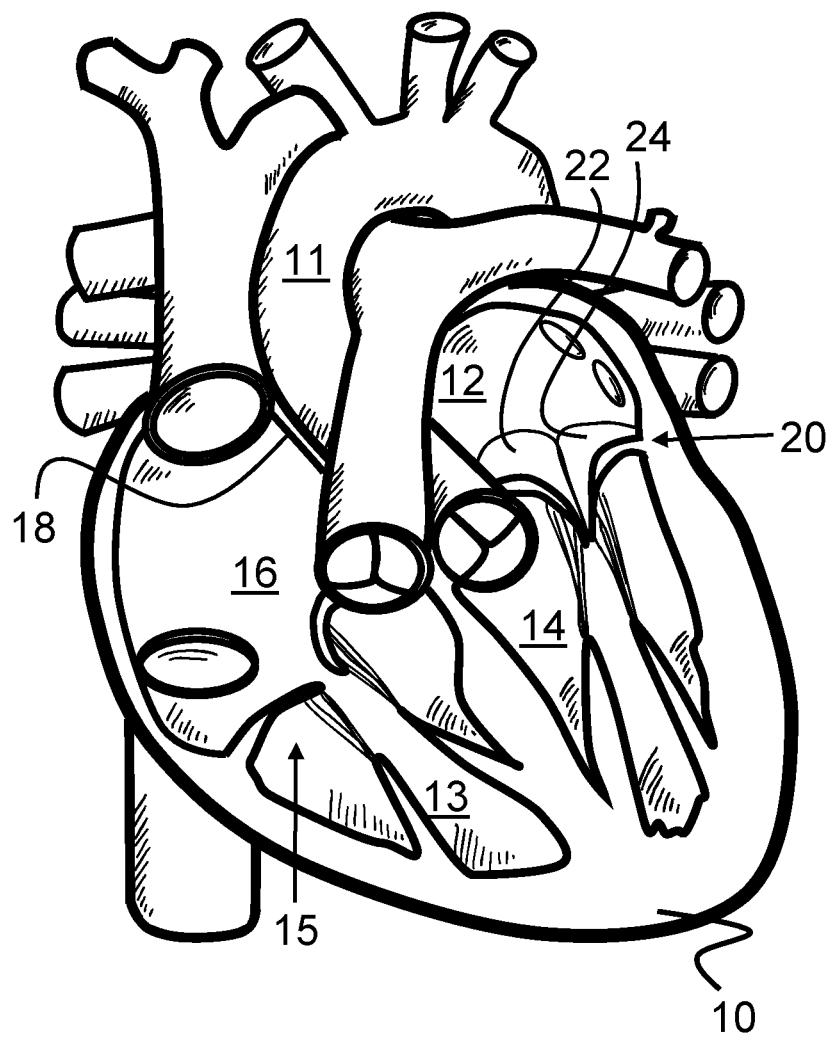
FIG. 1 illustrates the anatomy of a heart.
Figure 2:
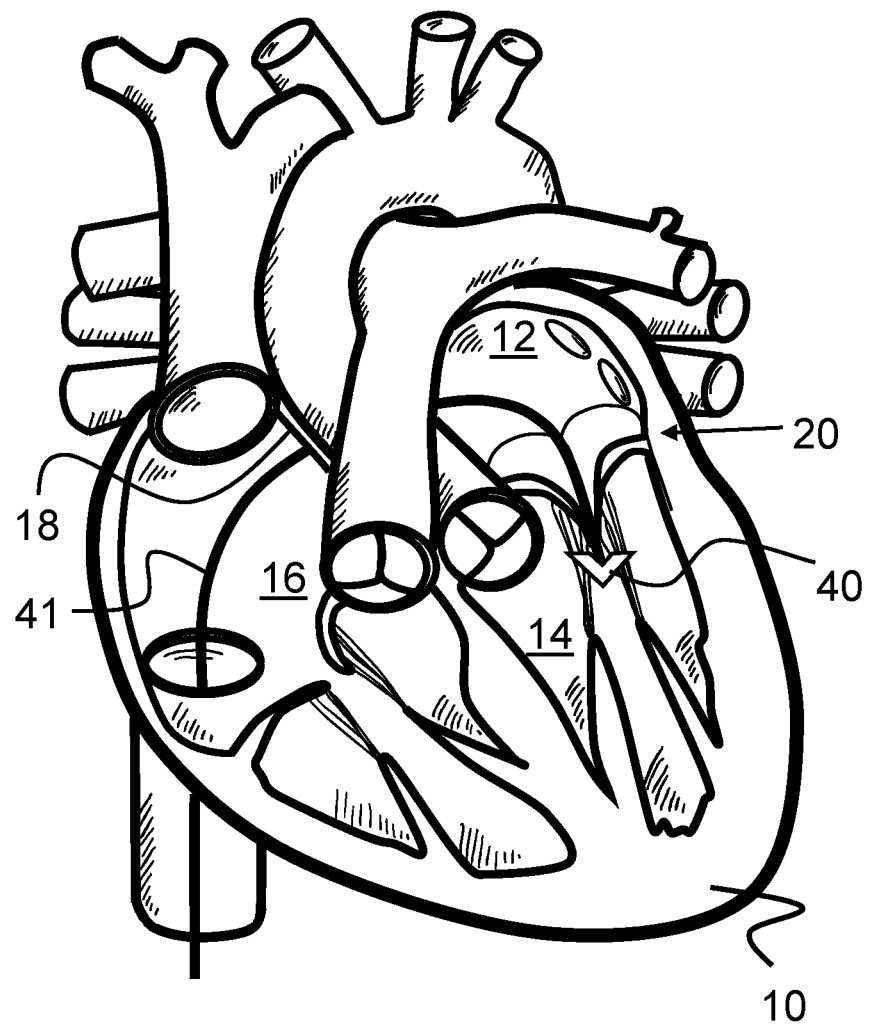
FIG. 2 illustrates a side view of a procedure to implant a leaflet heart valve therapy device.
Figure 3:
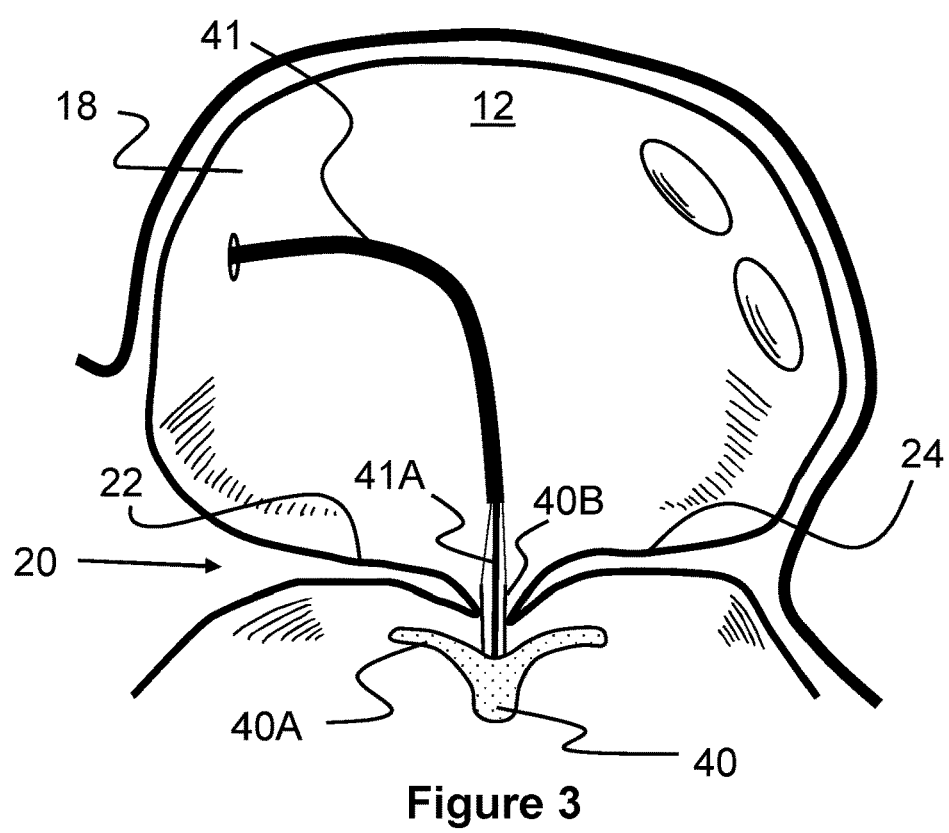
FIG. 3 illustrates a side view of a procedure to implant a leaflet heart valve therapy device.
Figure 4:
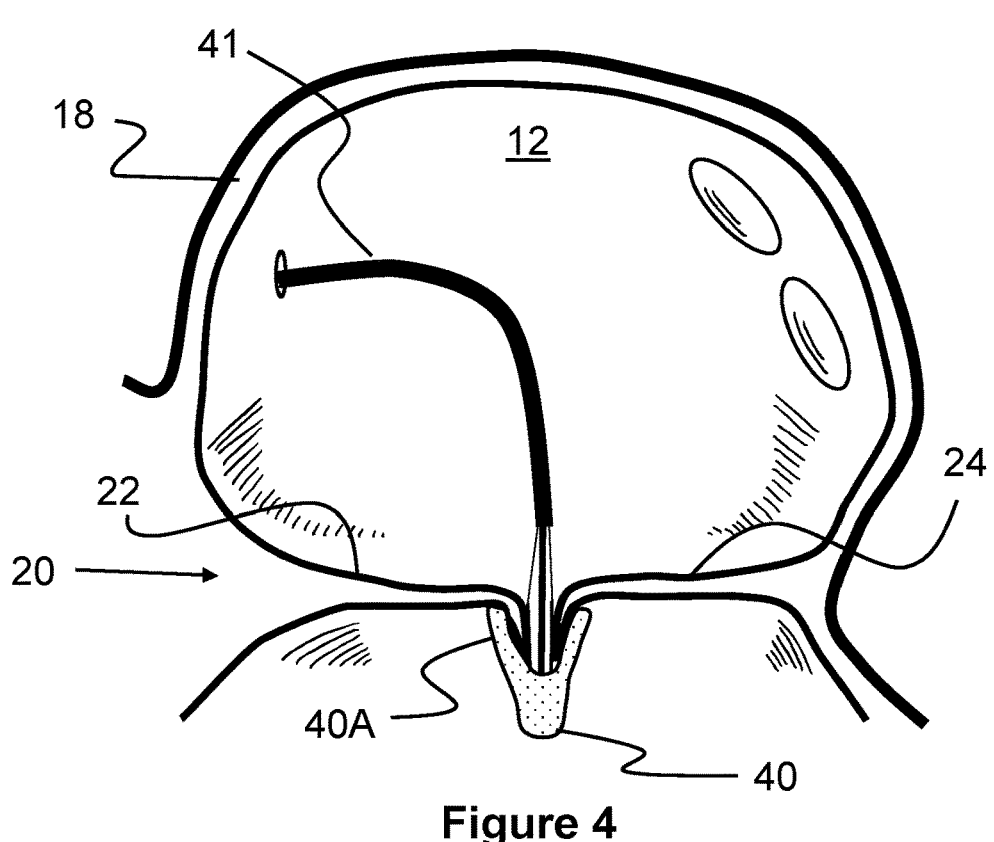
FIG. 4 illustrates a side view of a procedure to implant a leaflet heart valve therapy device.
Figure 5:
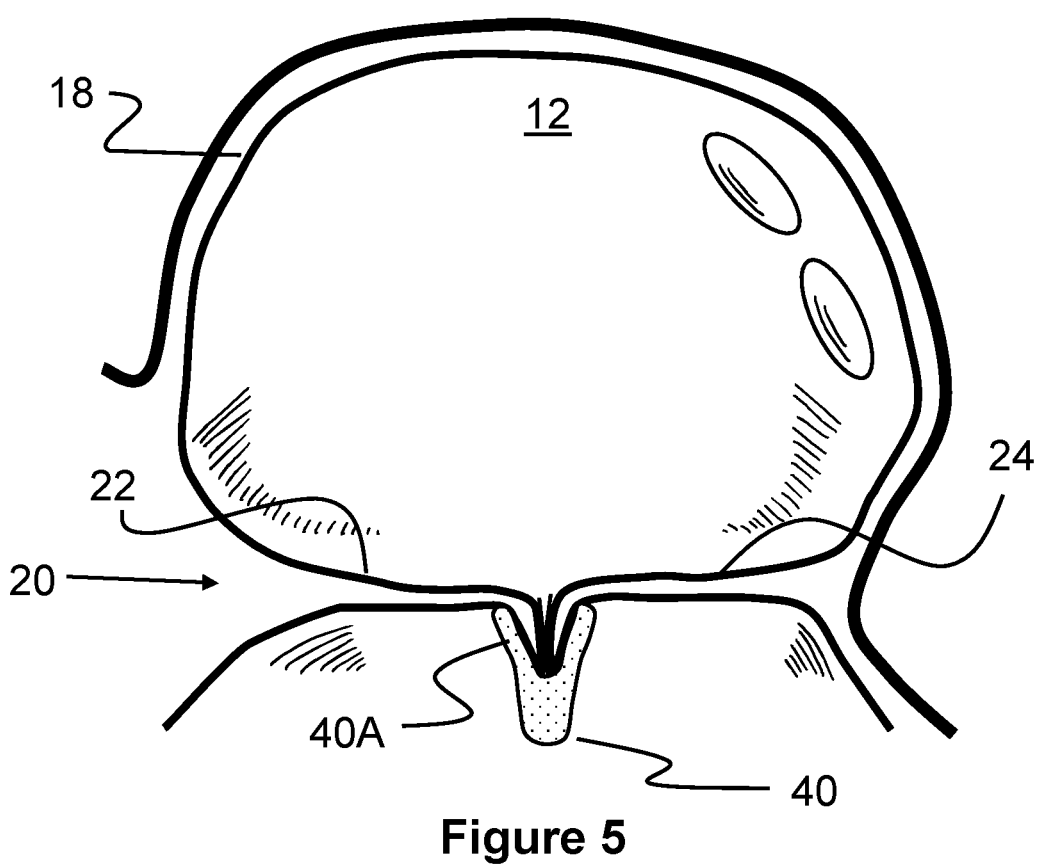
FIG. 5 illustrates a side view of a procedure to implant a leaflet heart valve therapy device.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is generally directed to devices and methods for removing heart valve therapy via a transcatheter procedure. While current methods for removal of heart valve therapy require open heart surgery, the techniques and devices of the present invention utilize transcatheter devices and procedures which are less invasive and can provide better patient outcomes.

FIGS. 1-13 illustrate various aspects of one embodiment of a removal catheter 100 for removing a leaflet heart valve therapy, such as a valve clip 40 or similar heart valve therapy device, according to the present invention. The removal catheter 100 generally includes an expandable capture basket 102 and a cutting loop 104 that is disposed near a top opening of the basket 102. As seen in FIGS. 7 and 8, the basket 102 is placed over an implanted valve clip 40 so that a top of the basket 102 and the cutting loop 104 are positioned between the clip 40 and the leaflets 22, 24 on the leaflets 22, 24 atrial side. Next, the top opening of the basket 102 is closed or decreased in diameter and the cutting loop 104 is activated to cut the leaflet tissue surrounding the valve clip 40 (e.g., supplying radio frequency energy), freeing the clip 40 from the valve 20. Finally, the capture basket 102 containing the valve clip 40 is retracted and removed from the patient. Further details and variations of the removal catheter 100 are discussed below, followed by example approaches and methods of removal for various heart valves (e.g., a mitral valve 20 or a tricuspid valve 15).

Figures 9, 10:
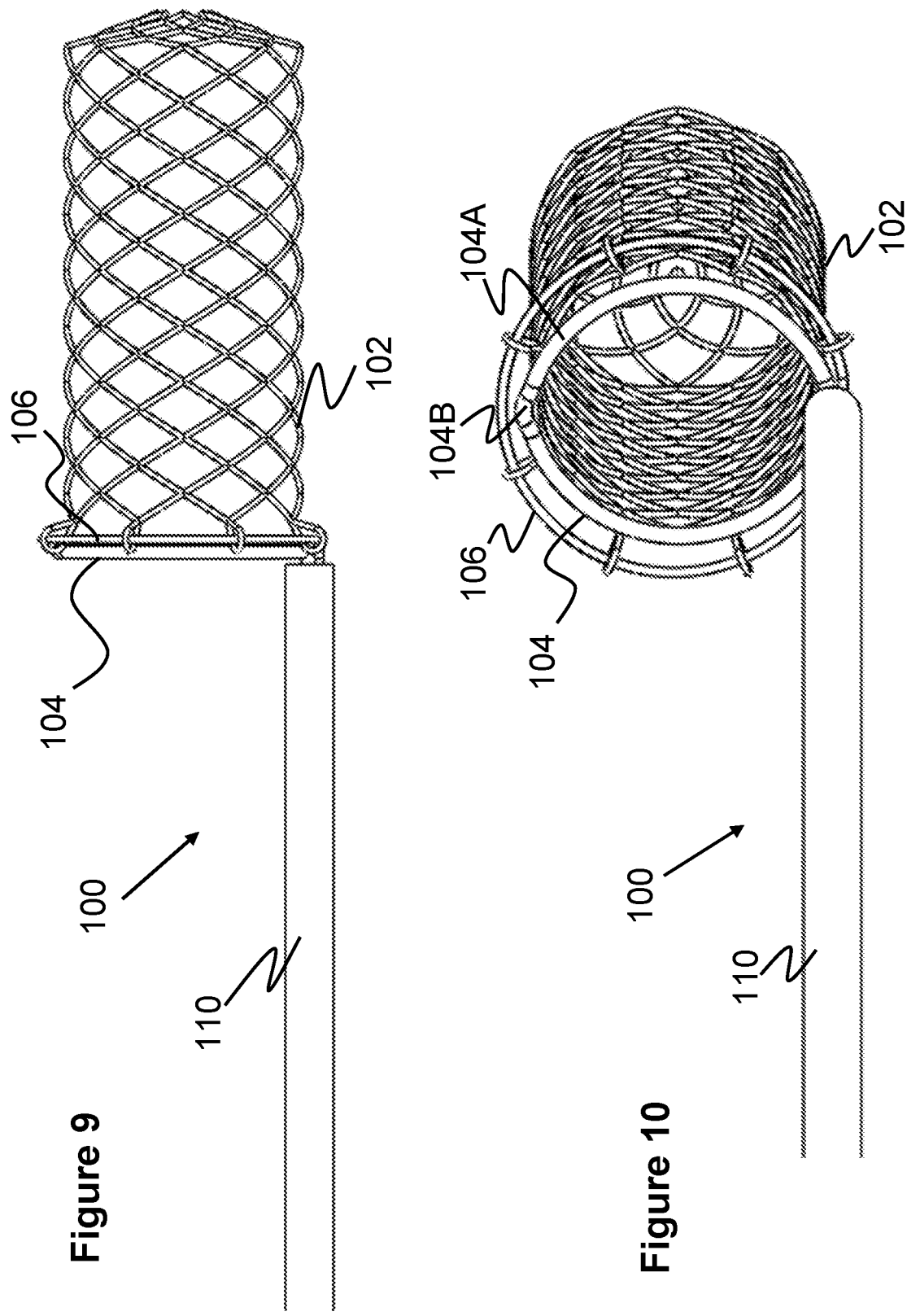
FIG. 9 illustrates a side view of a removal catheter according to the present invention.
FIG. 10 illustrates a side perspective view of a removal catheter according to the present invention.
Figure 11:
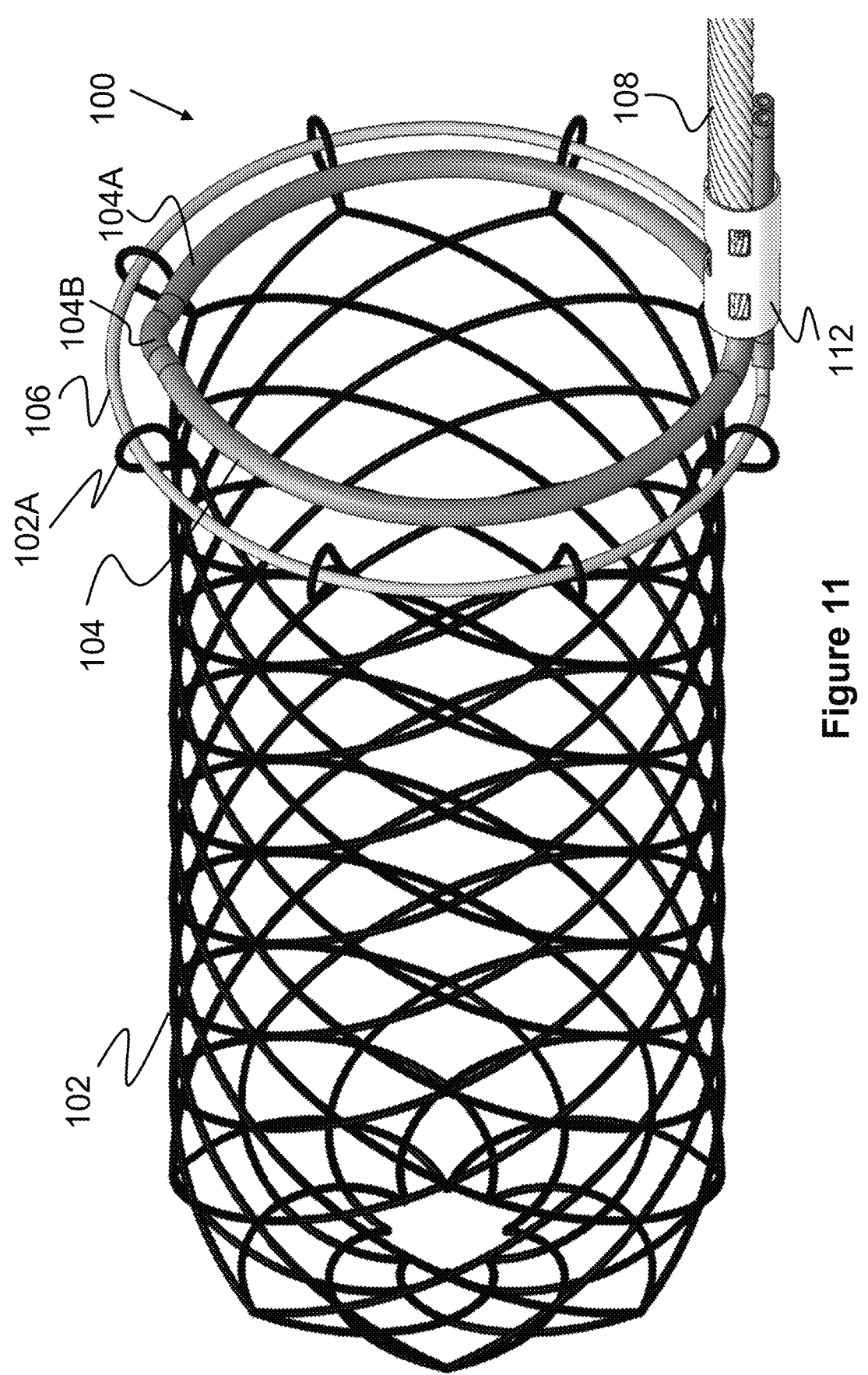
FIG. 11 illustrates a side view of a removal catheter according to the present invention.

As best seen in FIGS. 9-11, the removal catheter 100 includes an inner control member 108 (seen best in FIG. 11) that is positioned within an outer tubular sheath 110. The inner control member 108 can be a solid wire or tube that extends between a distal end and a proximal end of the sheath 110. The basket 102 and cutting loop 104 are connected to a distal end of the inner control member 108 such that when the inner control member 108 is longitudinally or rotationally moved relative to outer tubular sheath 110, the basket 102 and cutting loop 104 are similarly moved.

Figures 12, 13:
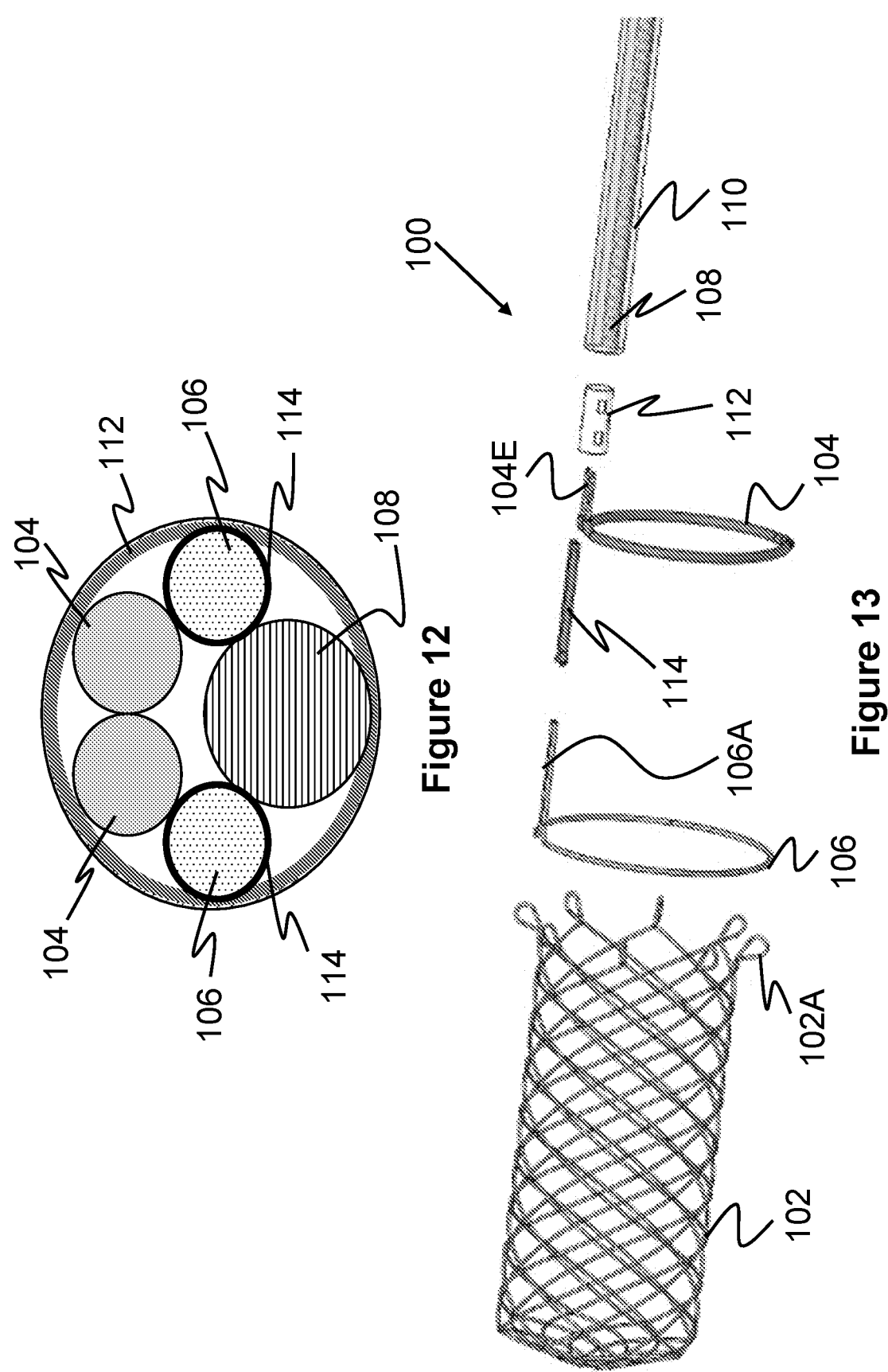
FIG. 12 illustrates a cross-sectional view of a removal catheter according to the present invention.
FIG. 13 illustrates an exploded view of a removal catheter according to the present invention.

Referring to FIG. 11, in one embodiment, a plurality of loops 102A are positioned around the circumference of the top opening of the basket 102 and a wire or cinching loop 106 is disposed through the loops 102A. As best seen in FIG. 13, the cinching loop 106 can be composed of a loop shaped wire (e.g., circular, oval, etc.) and an elongated straight portion 106A that that can be connected to the control member 108 via a connecting sleeve 112. The connecting sleeve 112 can be clamped, welded, applied with adhesive/epoxy, or any combination of the same to affix the sleeve 112 to the control member 108. Alternately, the cinching loop 106 can be connected to the control member 108 only via welding or adhesive.

The cutting loop 104 can similarly be formed in a general loop shape (e.g., circular, oval, saddle shape, etc.) and can include an elongated straight portion 104E that can also be connected to the control member 108 via the connecting sleeve 112. In this respect, both of the elongated straight portions 106A and 104E are located within the connective sleeve 112, as seen in the cross-sectional view of FIG. 12.

In one embodiment, the cutting loop 104 cuts tissue when radio frequency energy is supplied to it. In one example, the RF power source is connected to a proximal end of the control member 108 which is composed of a conductive metal and therefore communicates the RF energy to its distal end and then into the attached cutting loop 104. To complete the RF energy circuit with the cutting loop 104, a second RF electrode can be connected to the RF power source and can be attached elsewhere to the patient via an electrode pad (a monopolar RF system), a second electrode can be included elsewhere on the removal catheter 100 (a bipolar RF system), or a second insulated wire can be included on the control member 108 (a bipolar RF system).

It may be desirable to isolate the RF energy circuit of the cutting loop 104 from both the cinching loop 106 and the basket 102 to prevent other tissue in the heart from being damaged. This can be achieved with the use of electrical insulation as specific locations on the device. For example, electrical wire insulation 114 can be placed over the elongated straight portion 106A (or optionally the entire cinching loop 106) to electrically isolate the cinching loop 106 from the RF current of the control member 108, as seen in the cross sectional view of FIG. 12 and the exploded view of FIG. 13.

Figure 14:
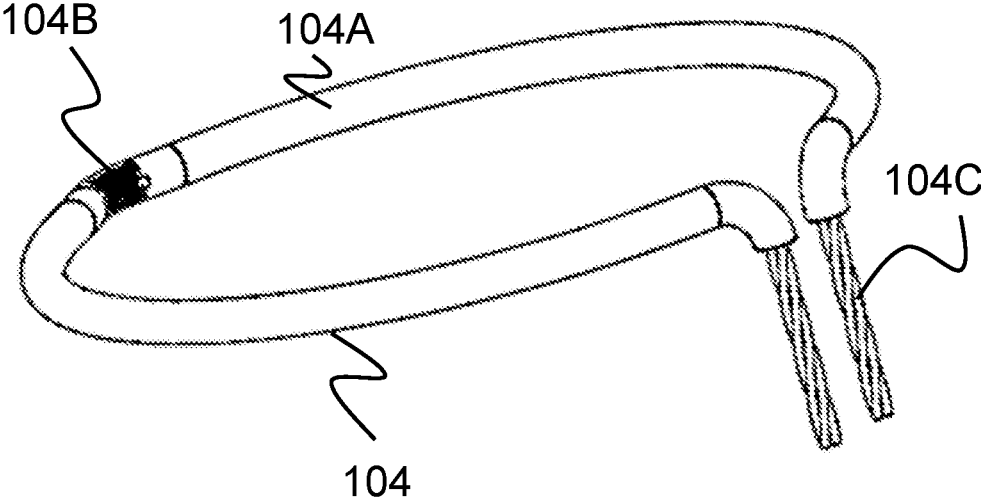
FIG. 14 illustrates a perspective view of a cutting loop according to the present invention.
Figure 15:
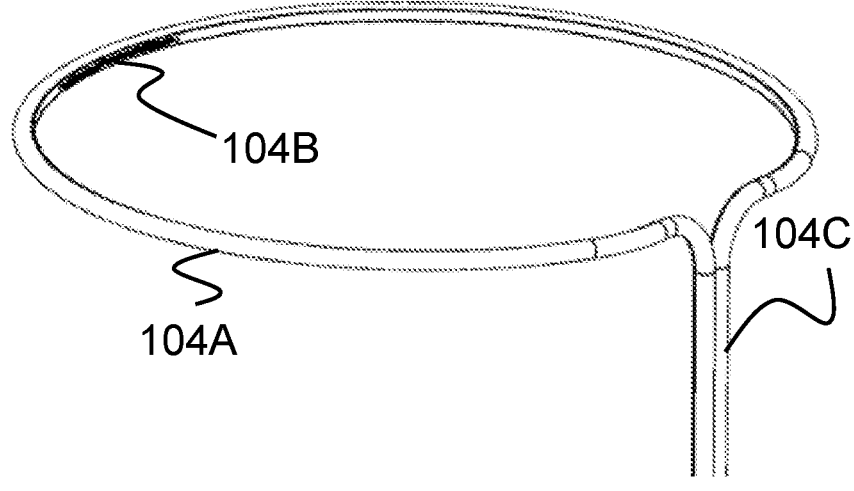
FIG. 15 illustrates a perspective view of a cutting loop according to the present invention.
Figure 16:
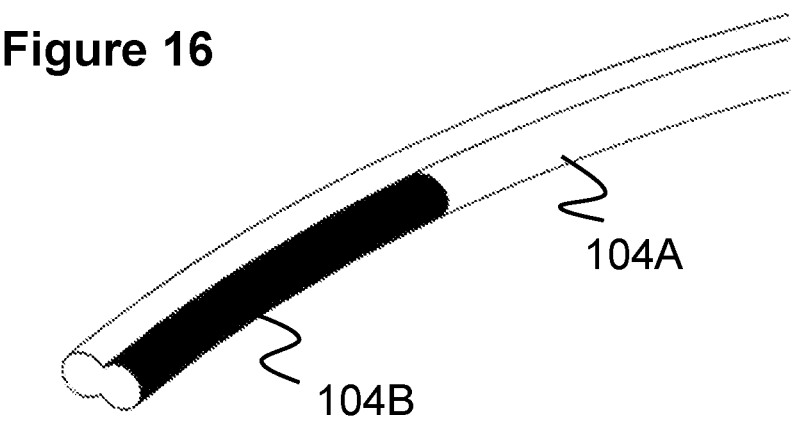
FIG. 16 illustrates a perspective view of a cutting loop according to the present invention.
Figure 17:
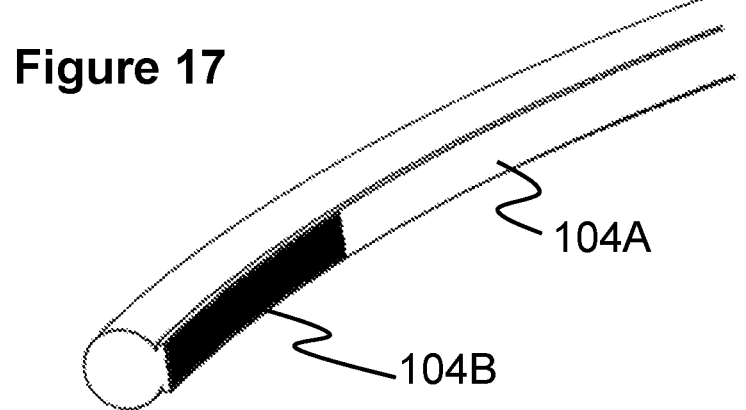
FIG. 17 illustrates a perspective view of a cutting loop according to the present invention.
Figure 18:
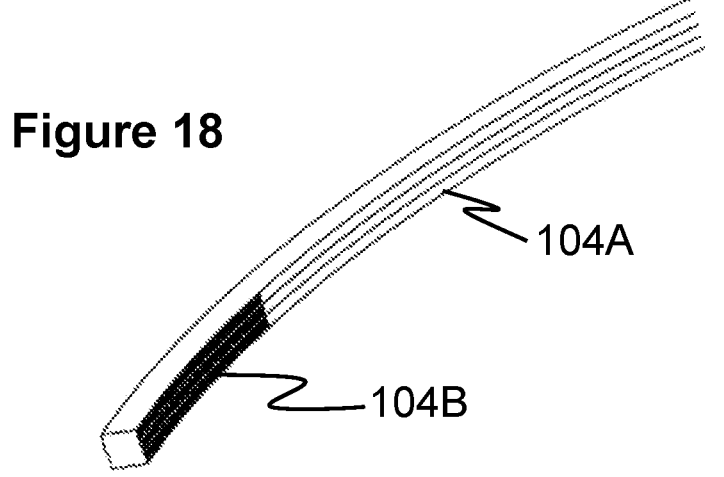
FIG. 18 illustrates a perspective view of a cutting loop according to the present invention.
Figure 19:
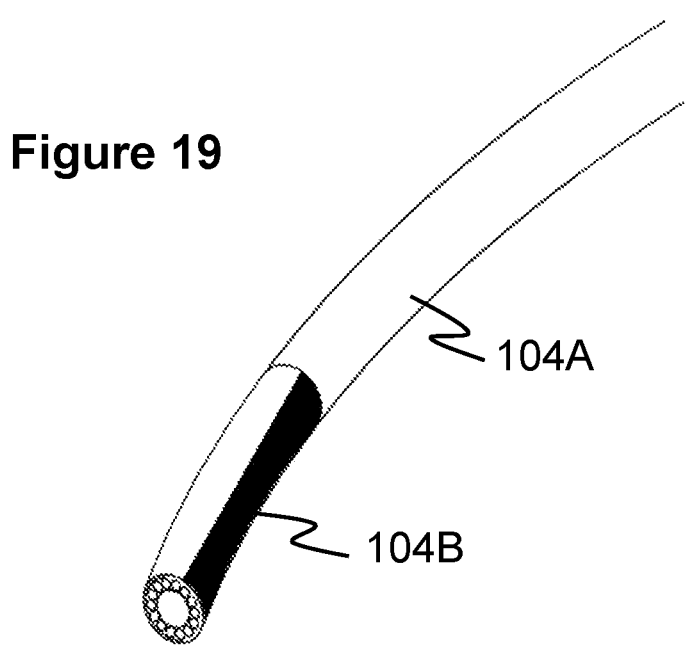
FIG. 19 illustrates a perspective view of a cutting loop according to the present invention.
Figure 20:
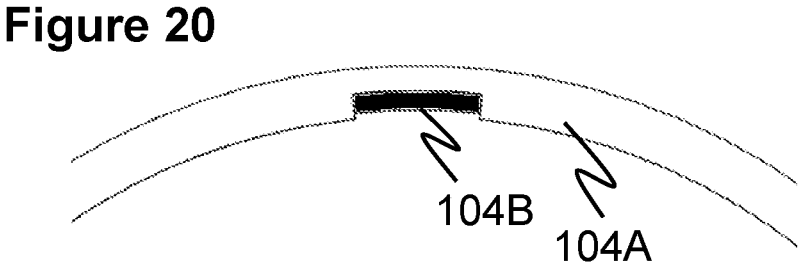
FIG. 20 illustrates a top view of a cutting loop according to the present invention.
Figure 21:
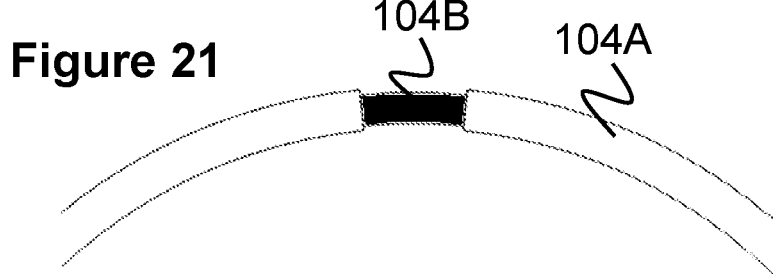
FIG. 21 illustrates a top view of a cutting loop according to the present invention.

In other examples seen in FIGS. 14-30, the cutting loop 104 can have different structures, shapes, and electrical insulation to help reduce the risk of an uninsulated portion 104B (i.e., the portion that cuts the leaflet tissue) from contacting any portion of the cinching wire 106 or basket 102. For example, FIG. 14 illustrates a cutting loop 104 in which the uninsulated portion 104B of the wire is located opposite of the elongated straight portion 104E, adjacent to insulated portions 104A on each side. In this example, the uninsulated portion 104B can extend entirely around the circumference of the wire as seen in FIG. 21 or can only be exposed along the interior side of the loop 104 as seen in FIG. 20.

Figures 22, 23, 24, 25, 26, 27, 28, 29, 30:
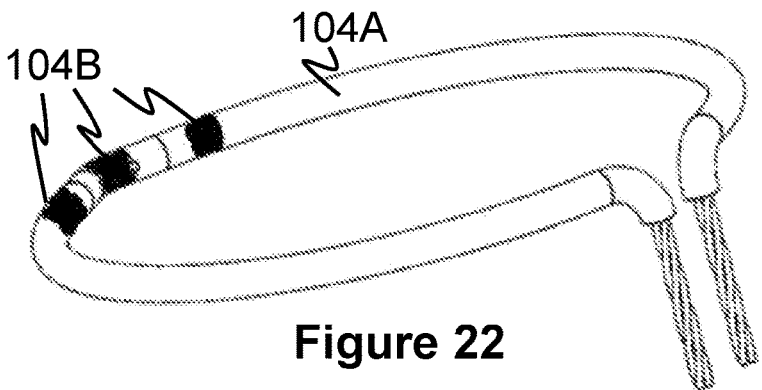
FIG. 22 illustrates a perspective view of a cutting loop according to the present invention.
FIG. 23 illustrates a cross-sectional view of a cutting loop according to the present invention.
FIG. 24 illustrates a cross-sectional view of a cutting loop according to the present invention.
FIG. 25 illustrates a cross-sectional view of a cutting loop according to the present invention.
FIG. 26 illustrates a cross-sectional view of a cutting loop according to the present invention.
FIG. 27 illustrates a cross-sectional view of a cutting loop according to the present invention.
FIG. 28 illustrates a cross-sectional view of a cutting loop according to the present invention.
FIG. 29 illustrates a cross-sectional view of a cutting loop according to the present invention.
FIG. 30 illustrates a cross-sectional view of a cutting loop according to the present invention.

The uninsulated portion 104B may include only a single area in which the underlying wire 104C is exposed (e.g., between about 1 and 5 mm) as seen in FIG. 14 or can include a plurality of discrete uninsulated portions 104B (e.g., 2-10 portions 1046) of a relatively smaller length (e.g. between about 1 and 5 mm) as seen in FIG. 22.

In all cutting loop embodiments, the majority of the surface of the cutting loop 104 is insulated. To create the uninsulated portion 104B, the cutting loop insulation 104A can be selectively removed (for wires with existing insulation) to expose the cutting loop conduction wire 104C in a manner that will allow it to contact and deliver the RF cutting energy to the leaflet tissue bridge when it is in contact with tissue in proximity to the heart valve therapy. Alternately, the insulation 104A can be added (e.g., by dipping, spraying, or similar techniques) and the uninsulated portions 104B can be created by masking the intended areas prior to insulation application.

It will be understood that the uninsulated portion 104B can be oriented any number of ways, e.g., on the inner/outer surface of the cutting loop 104 as well as on the bottom (i.e., atrial) side of the loop 104.

The underlying wire 104C of the cutting loop 104 may be composed of a shape memory metal (e.g., Nitinol) or a similar conductive metal (e.g., stainless steel or copper). As seen in the cross-sectional views of FIGS. 23, 24, and 25, the underlying wire 104C can have a rectangular cross section, a circular cross section, a triangular cross section, and a square cross section, respectively.

The cutting loop 104 may also be composed of one or more wires, such as a first wire 104C and a second wire 104D. Both wires can be composed of similar material (e.g., Nitinol, stainless steel, copper, silver, or similar materials), or each wire can be composed of a different material. For example, one wire 104C can be composed of a metal that better conducts current (e.g., stainless steel, silver, or copper) and the other wires 104D can be composed of a material that retains its shape between a compressed and expanded configuration (e.g., shape memory metal such as Nitinol). The multiple wires may be electrically isolated or insulated from each other or independently. Different cross sectional shapes can be further used with the same or different materials, as seen in FIGS. 16-18 and 26-28.

In another example, the cutting loop 104 may be composed of a single wire containing a plurality of strands of different wire materials. For example, FIGS. 19 and 29 illustrate a wire core 104D composed of a shape memory strand with a plurality of conductive strands 104C are located circumferentially around the core 104D. In another Example, FIG. 30 includes alternating shape memory strands 104D and conductive strands 104C. In this respect, the different strands may provide both desirable current conduction and the ability to expand to a predetermined loop shape from a compressed configuration. The multiple wires may be electrically isolated or insulated from each other or independently. Either of these two cable examples can have 2-49 or more strands within them.

Figure 101:
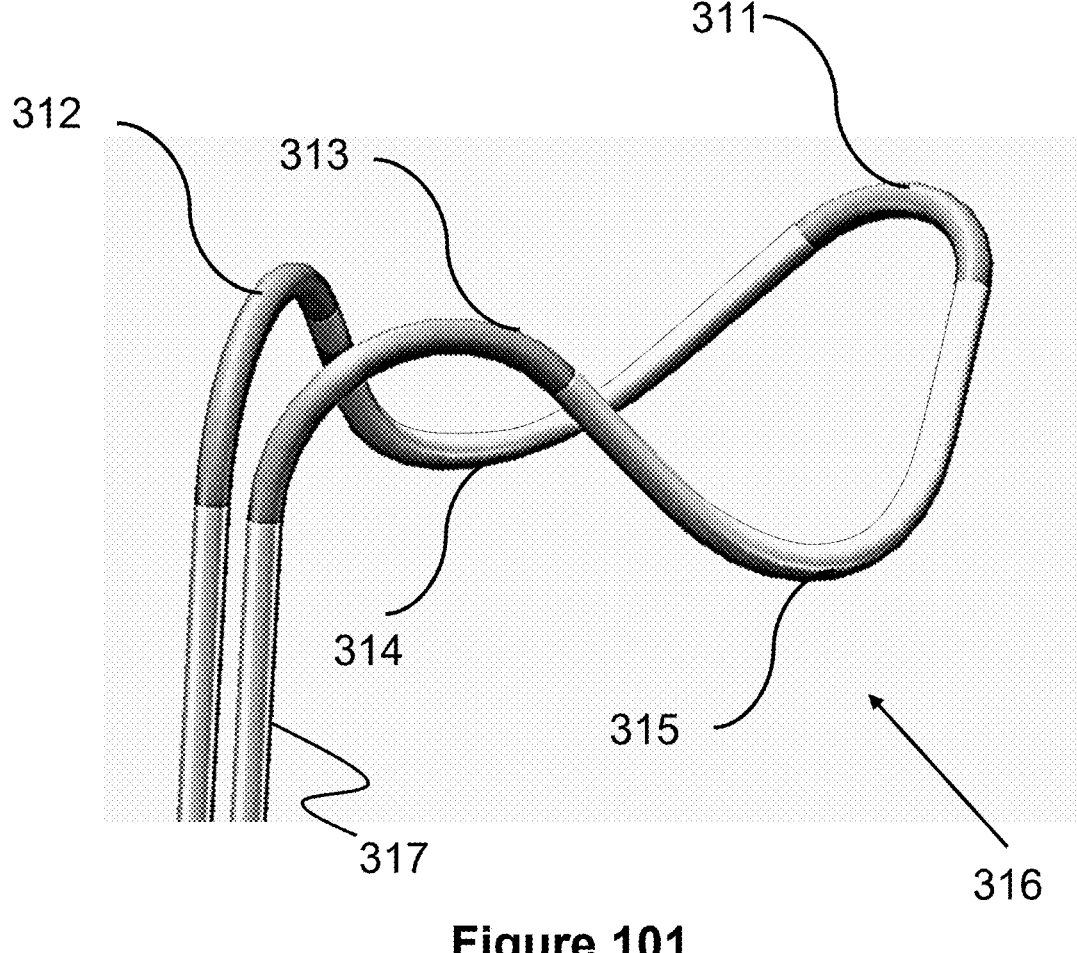
FIG. 101 illustrates a perspective view of a removal catheter apparatus according to the present invention.

The cutting loop may have a variety of different shapes, structures, and electrical insulation patterns to facilitate tissue removal around the clip 104 that can, for example, provide additional length and/or a predetermined path or geometry. FIG. 101 illustrates one alternate example of a cutting loop 316 having a "saddle" or wave shape in which each side portion 314, 315 of the loop dips downward (i.e., in a proximal direction toward the catheter 100) and its free end 311 bends upwards (i.e., in a distal direction away from the catheter 100). Side portions 314 and 315 can be insulated and middle portion 311 and end portions 312 and 313 can be insulated. The middle portion 311 contacts or engages the tissue on one side of the loop 316, while end portions 312 and 313 contact or engage the tissue on the other side. The side portions 315 and 316 can bend outwards to increase the width of the loop 316, inwards to decrease the width of the loop 316, or can be relatively straight to maintain a uniform width of the loop 316 (i.e., circular or elliptical in shape).

Many different tissue engagement methods can be facilitated by to the cutting loop 316, such as end portions 312 and 313 can be electrically activated first in unison while the cutting loop 316 applies axial tension onto the tissue structure, effectively cutting the tissue in contact with those portions 312, 313 and partially freeing the leaflet clip 40. Next, the free end portion 311 can be activated to excise the tissue adjunct to it and completing the excision of the leaflet clip 40 from the leaflets. Alternately, all three portions 311, 312, and 313 can be activated at the same time. Axial tension on the loop 316 can be applied before, during, or intermittently to control the engagement of the loop 316. This embodiment illustrates three uninsulated cutting areas or portions 311, 312, and 313, however there may be any number of cutting elements (e.g., from 1-100), including the entire loop 316 as being one continuous, uninsulated cutting member.

Including additional length along the side portions 314 and 315 can accommodate other tissue structures present around the leaflet clip 40. The extra length of the side portions 314 and 315 can also be deformable such that when tension is applied by the elongated straight portions 317, the side portions 314 and 315 will straighten and cause the loop 316 to elongated to an approximate axial configuration. During this tension and elongation, the axial distance between the free end portion 311 and the proximal end portions 312, 313 is increased, accommodating a greater variation in both diameter and approach angle to the clip. Any such nonlinear path could also accomplish this and are hence considered in this disclosure, but for sake of brevity are not shown herein.

Figure 102:
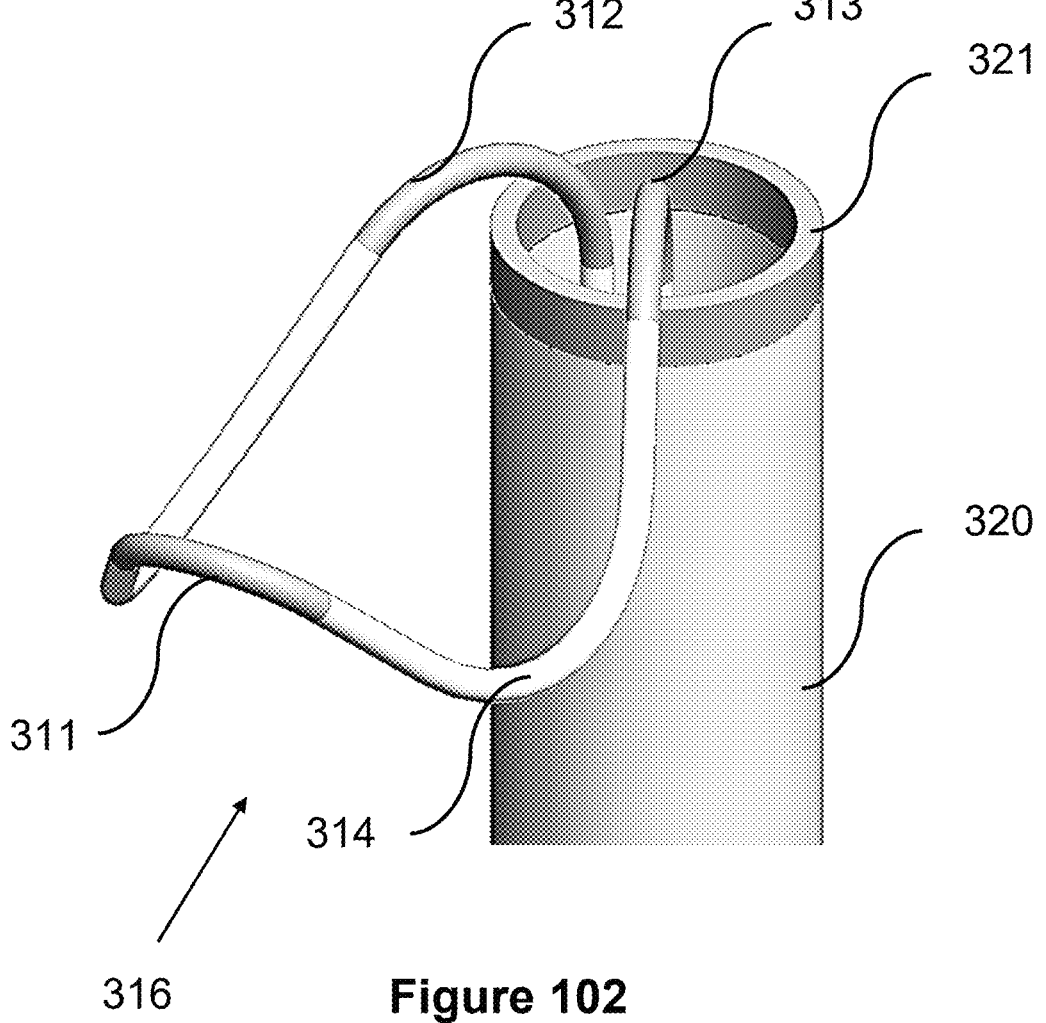
FIG. 102 illustrates a perspective view of a removal catheter apparatus according to the present invention.

FIG. 102 illustrates a delivery mechanism with a previously described cutting loop 316 and an outer tubular sheath 320 that is generally similar to that of previously described sheath 110. However, the outer tubular sheath 320 further includes a sheath cutting portion 321 that is disposed at and circumferentially around the distal end of the sheath 320. This sheath cutting portion 321 can be of similar construction and characteristics as previously described uninsulated portions of the prior cutting loops and can be similarly electrically activated to provide facilitate additional areas of tissue that can be cut. This outer tubular sheath 320 can be used in conjunction with any of the other apparatuses disclosed and in a method that best facilitates the leaflet clip removal procedure. Again, all of the uninsulated cutting portions 311, 312, 313, and 321 can be activated individually at different times or all together at the same time.

Figure 103:
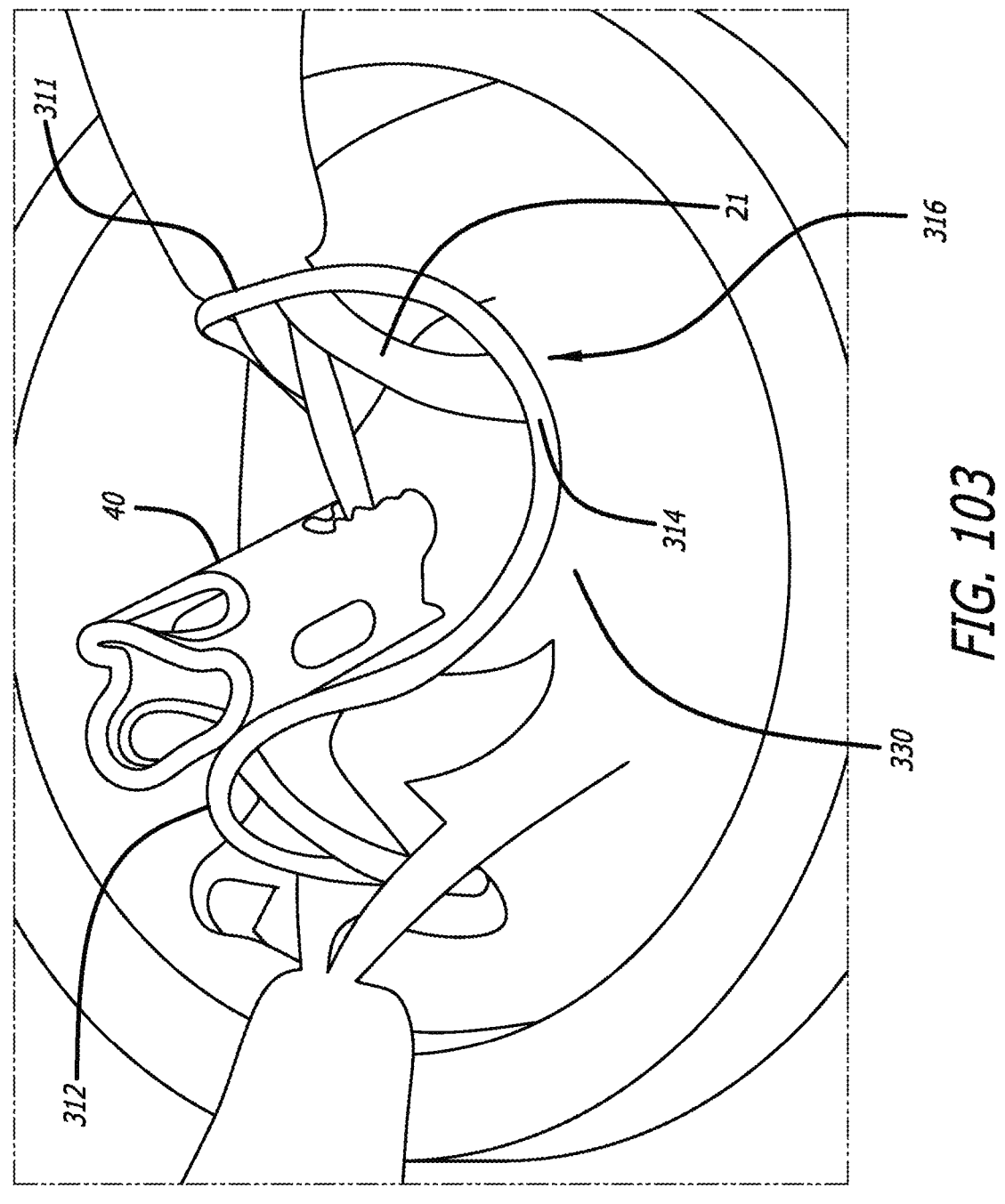
FIG. 103 illustrates a perspective view of a removal catheter apparatus according to the present invention.

FIG. 103 illustrates the embodiment of FIG. 102 within a heart valve tissue model 330, with chordae 13 and a leaflet positioning clip 40. This figure illustrates one example of how the apparatuses 320 and 316 engage tissue on all sides of the clip 40 in a manner that is positioned to sever the attaching tissue structures from the clip apparatus 40.

Figure 104:
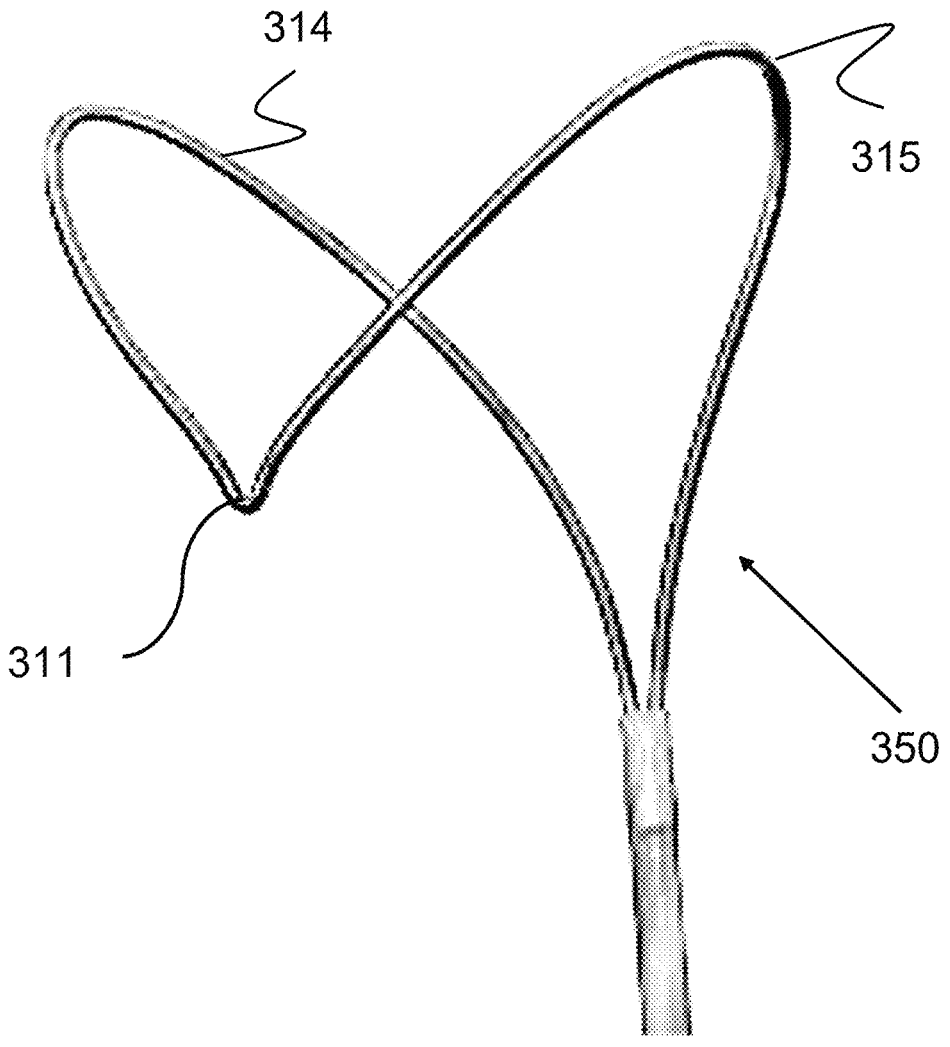
FIG. 104 illustrates a perspective view of a removal catheter apparatus according to the present invention.

Another example embodiment of a cutting loop 350 can be seen in FIG. 104, in which each side loop portion 314, 315 bends upward (i.e., in a distal direction) and its free end bends downward (i.e., in a proximal direction). Additionally, the side loop portions 314, 315 are shown bending laterally outward, increasing the width of the loop 350. The loop 350 can have a variety of different insulated and uninsulated portions, such as those described in FIGS. 101-103 (i.e., several discrete uninsulated portions or the entire loop being uninsulated).

Figure 105:
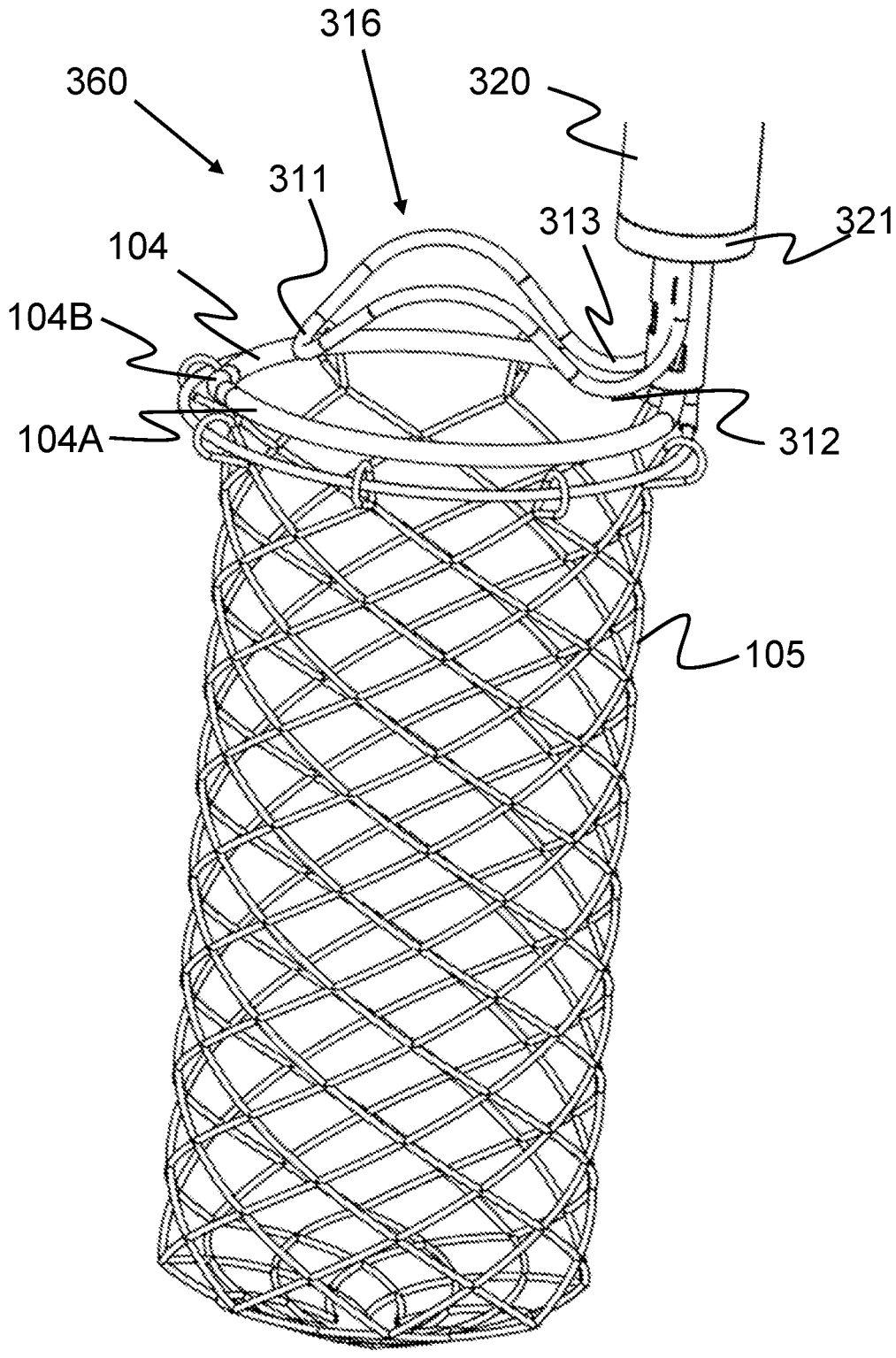
FIG. 105 illustrates a perspective view of a removal catheter apparatus according to the present invention.
Figure 106:
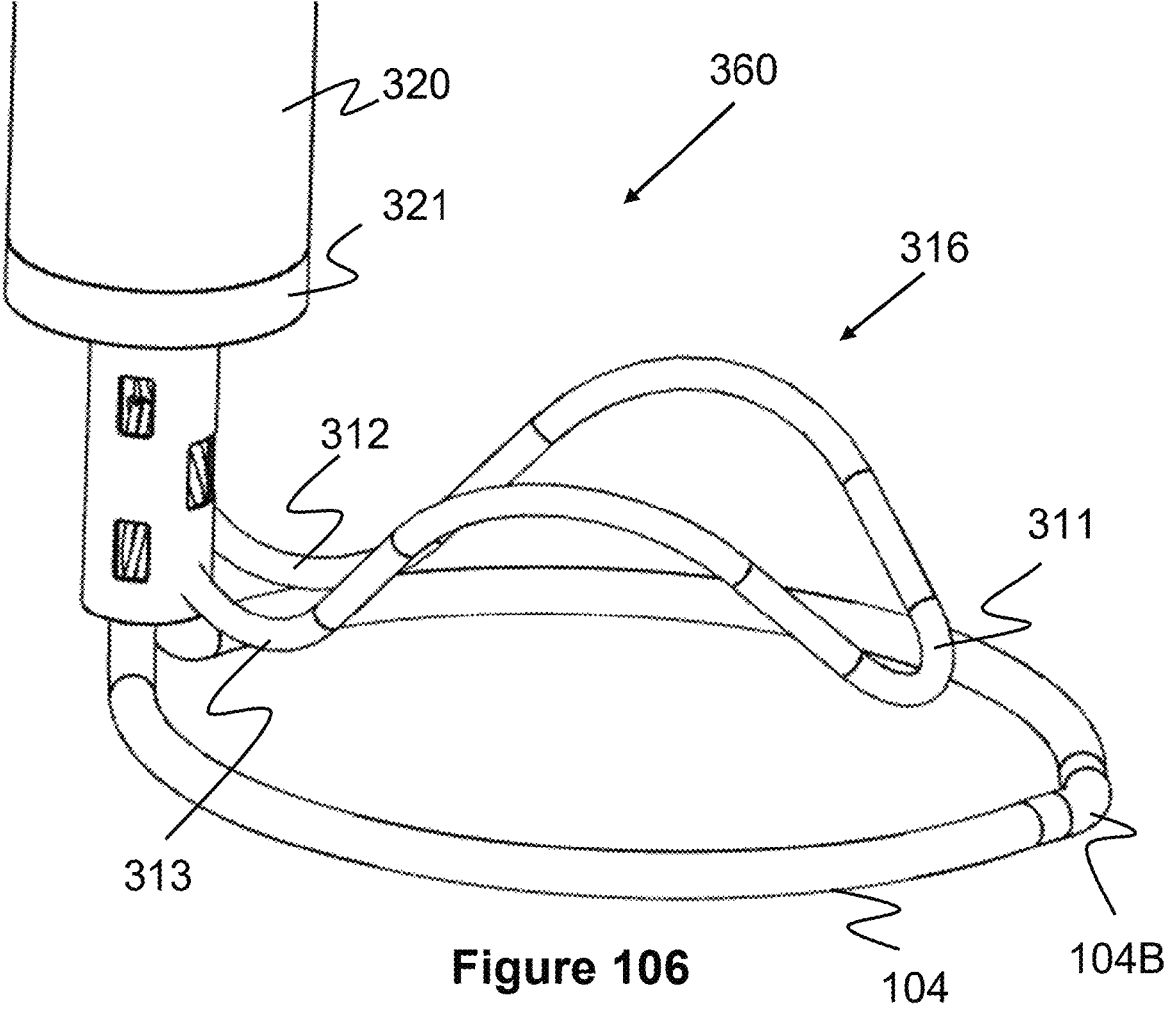
FIG. 106 illustrates a perspective view of a removal catheter apparatus according to the present invention.

FIGS. 105 and 106 illustrate another embodiment of a removal device 360 that is generally similar to the removal device 100 but further includes a first cutting loop 104 and a second cutting loop 316. In some instances, it may be difficult for the physician to visualize exactly what tissue should be cut to completely remove a heart therapy device. Two or more loops may allow for a first series of cuts to the valve tissue and then one or more second cuts (e.g., via cinching the first cutting loop) to completely remove the heart therapy without the need for dramatic repositioning of the loops. In contrast, a single cutting loop may need to be moved, longitudinally repositioned, and/or rotated to fully cut out the heart therapy.

Figure 107:
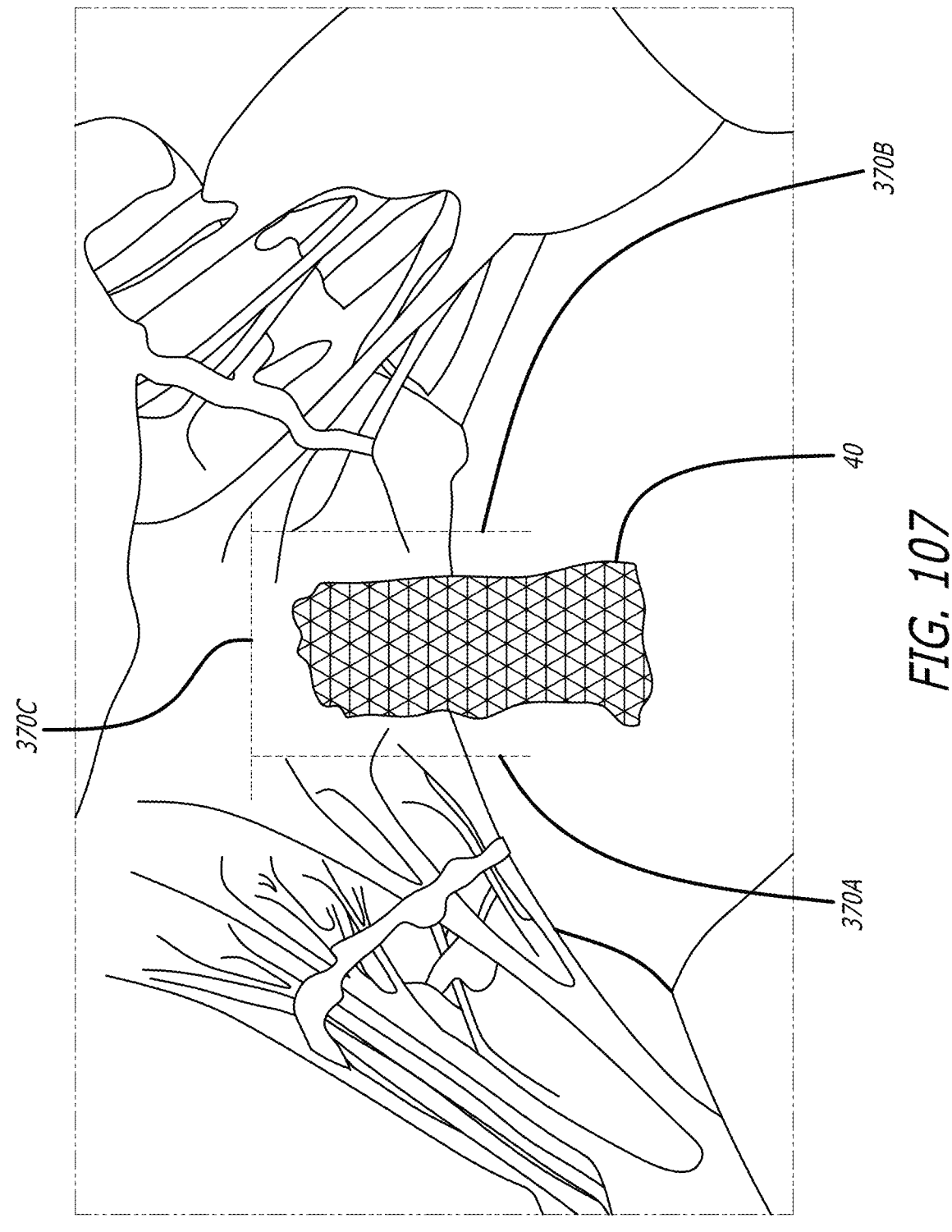
FIG. 107 illustrates a perspective view of example cuts to a valve.

In the present example, the first cutting loop 104 has a somewhat larger diameter (e.g., similar to the opening of the basket 104) and the second cutting loop 316 has a diameter that is smaller than the first cutting loop 104 and that is positioned further away from the basket 104. Hence, the second loop 316 may be placed against the valve leaflets and/or chords (e.g., cut 370A through the antero-lateral chords and cut 370B through the postero-medial chords in FIG. 107) and the cutting portions 311, 313, and 313 can be activated to perform the first series of cuts to the tissue. This first series of cuts may not cut all of the tissue, however the cutting portion 104B of first cutting loop 104 can cinched and then activated to perform one or more second cuts to completely remove any remaining tissue from the heart therapy device 40 (e.g., along cut 370C on the atrial side of the clip 40 in FIG. 107).

Figure 108:
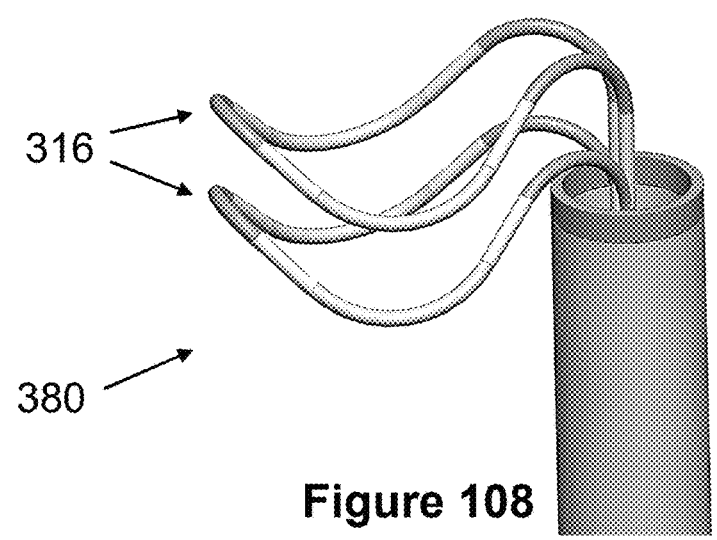
FIG. 108 illustrates a perspective view of a removal catheter apparatus according to the present invention.

While specific embodiments of the cutting loops 104 and 316 are shown in FIGS. 105 and 106, any combination of any of the loops described in this specification can be used in this manner. For example, FIG. 108 illustrates an embodiment 180 with two loops 316 of similar shape and configuration. Hence, either of the loops may have different numbers and patterns of cutting portions and may activate those cutting portions all simultaneously or at different times/patterns. In one example, both of the cutting loops 104 and 316 are connected to the same electrical circuit (e.g., the inner control member 108). Alternately, each loop 104, 316 (or alternately each set of cutting portions) may have its own electrical circuit (e.g., individual conducting wires) that allows for independent activation from the other cutting loop. Additionally, three or four cutting loops may alternately be used. The cutting loops may all be connected to the same removal catheter or one or more loops can be connected to a catheter separate from other cutting loops and/or the basket 104. In some embodiments one or more cutting loops may be located on the ventricular side of the valve while one or more cutting loops may be located on the atrial side of the valve.

If the cinching loop 106 has an insulation coating entirely along its length, the cutting loop 104 may be located directly on top of the cinching loop 106, contacting the loop. The cutting loop 104 may also be longitudinally spaced apart from the cinching loop 106, such as between about 0 mm and about 15 mm.

Preferably, the inner control member 108 (seen best in FIGS. 11-13) is flexible enough to navigate through the vasculature while having enough column strength to push the basket 102 and cutting loop 104 out of the outer tubular sheath 110, be capable of efficiently delivering RF energy from the proximal handle to the cutting loop, be insulated to prevent current leakage to the bloodstream, and have good torque response so the user can rotate the basket and loop when it is deployed in and around the valve.

In a preferred embodiment the inner control member 108 consists of an inner control stylet that is joined or welded to a more flexible inner control cable, which is then joined to the cutting loop conduction wire tails using a distal coupler. in a preferred embodiment the inner control stylet, inner control cable, cutting loop conduction wire, and distal coupler are the same material (e.g., steel alloy) to enable a strong weld joint and efficient current delivery throughout. The inner control cable could be a laser cut tube, a stranded cable, a stranded cable tube, a coil, or a combination of these. In another embodiment, the inner control cable may extend from the proximal handle to the cutting loop 104, and eliminate the need for the inner control stylet.

In an alternate embodiment, the inner control member 108 can be two separate wires; one of which connects to the cinching loop 106 and the other that connects to the cutting loop 104. In the case of both inner control members being disposed in the same single lumen of the outer tubular sheath 110, the basket 102 may be deployed first by advancing the inner basket control member distally until the basket cinching loop 106 is fully exposed. Then, the inner cutting loop control member can be advanced distally to deploy the cutting loop 104. Each of the loops can be rotated, advanced, or retracted by their respective control members. This provides the operator with more degrees of freedom. The heart valve therapy may be first captured or encircled by the cutting loop 104, and then the basket cinching loop 106 and basket 102 can follow. The cutting loop 104 can then be closed onto the leaflet tissue bridge by retracting the inner cutting loop control member. Once the cutting loop is closed on the tissue bridge, one of two steps can be taken: 1) the basket cinching wire 104 and basket 102 can then be closed by retracting the inner basket control member proximally or 2) if the cutting loop 104 is unable to get to the base of the heart valve therapy, RF cutting energy can be applied to cut down one side of the device to get to the base of the clip 40; then the basket 102 can be closed. Once both loops are properly closed on the tissue on the atrial side of the heart valve therapy, the inner cutting loop control member is energized with RF power as it is retracted proximally into the outer delivery sheath 110. The inner cutting loop control member delivers the cutting energy to only the cutting element through the cutting loop 104.

The aforementioned inner control members can alternately be disposed in separate outer tubular sheaths or separate lumens in the same sheath 110. It is possible for this system to be designed such that each sheath can be placed in separate orifices (i.e., on opposite sides of the heart valve therapy). Once both loops have captured the heart valve therapy, the same steps as described above would follow.

The control member insulation that covers the outer surface of the inner control stylet and inner control member is preferred to be flexible enough to not impact the navigation of the delivery catheter through a valve orifice. It is also desirable be as lubricious as possible, such that the friction between the inner control member and the delivery catheter is minimized as the inner control member is pushed distally to deploy the basket and cutting loop in the left ventricle. For example, this insulation may include a hydrophilic coating, a silicone coating, a Teflon like coating, a polyolefin coating, a thermoform or thermoset coating, or fluoropolymers.

Returning to the basket 102, the length and diameter of the basket 102 may depend on the size of the heart valve therapy device or clip 40. For example, the basket 102 may have a length within a range of about 20 mm to about 50 mm, and a diameter within a range of about 10 mm and 20 mm. Depending on the size of the leaflet clip 40 and the angle that the basket 102 is expected to capture the clip 40, the diameter of the basket 102 can be adjusted accordingly. For example, the greater the angle of interception relative to a top plane across the opening of the basket 102, the larger the diameter of the basket 102 should be. Put another way, unless it is expected that the basket 102 is to be substantially directly underneath the clip 40, the basket 102 should expand to a diameter much greater than that of the clip 40.

Figures 31, 32, 33, 34:
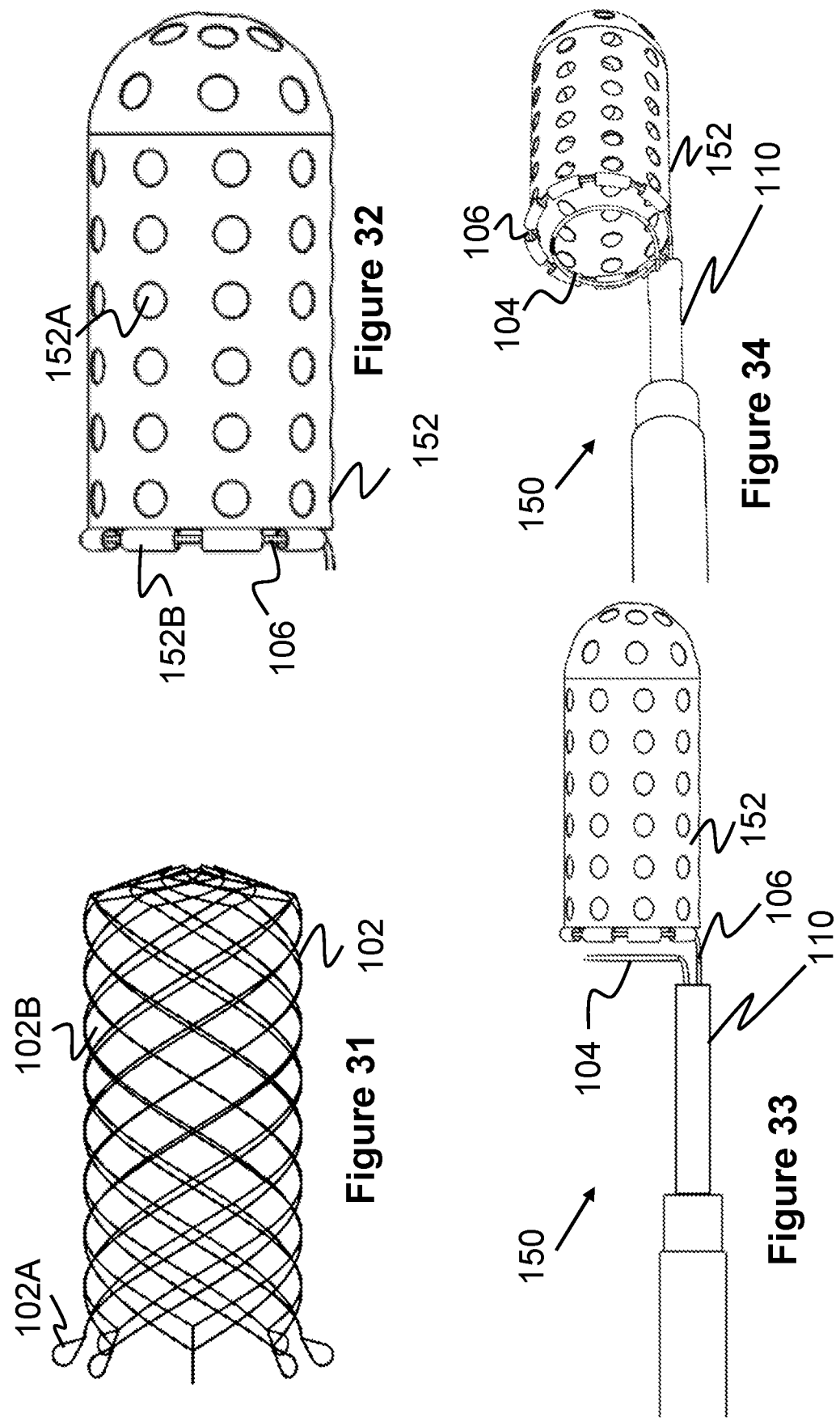
FIG. 31 illustrates a side view of a basket according to the present invention.
FIG. 32 illustrates a side view of a basket according to the present invention.
FIG. 33 illustrates a side view of a removal catheter according to the present invention.
FIG. 34 illustrates a side perspective view of a removal catheter according to the present invention.

In one embodiment seen in FIG. 31, the basket 102 can be composed of a plurality of braided wires. The wires can be composed of a shape memory material and can be braided on a mandrel of a desired basket size, then heat set so that the braided shape returns to the expanded basket configuration after being compressed. The wires can be composed of a shape memory material such as Nitinol or a non-shape memory material such as stainless steel. The wires may also have an insulating coating such as ETFE, polyimide, parylene, silicone, or similar materials. The benefits of a woven basket are that its behavior/performance can be altered by changing the basket wire diameter, basket wire material, and/or weave density (i.e., basket pore size) while keeping the diameter and length of the basket fixed. The basket diameter and length design are primarily driven by the size of the intended heart valve therapy to be removed. The size, spacing, and number of woven basket eyelets could also be adjusted and optimized. In one example, the pores 102B of the basket 102 when expanded are within a range of about 100 microns to about 4 mm in diameter.

The wire size is preferably small enough to allow for it to be easily collapsed into and deployed from the delivery catheter during the procedure, but large enough to give the basket some rigidity such that it can adequately open in the presence of valve chordae or other structures. The basket pore size can vary on a woven basket, depending on the design intent. In general, the pore size should be smaller than either the length, width, or height of the heart valve therapy to avoid it embolizing through the basket after it has been cut free. Weaving a basket with very small pores could help with filtering and capturing any debris generated during the tissue cutting process.

One benefit of coating a metal basket is to ensure the electrical energy is concentrated in the cutting element and not being distributed across the entire metal structure of the basket and into the blood pool. The second benefit of coating is that it can also reduce friction and therefore can facilitate easier capture of the heart valve therapy inside the basket. If the basket is too rough or there are too many edges inside the basket, the heart valve therapy may not want to fully seat within the basket. Adding a lubricious coating or a smooth layer to the inner surface of the capture basket may enable easier capture of the heart valve therapy.

In an alternate embodiment seen in FIGS. 32, 33, and 34, a removal catheter 150 includes a basket 152 composed of a polymer such as silicone, PET, polyester, nylon, polypropylene, Kevlar, or a similar material that can fold or pleat to a radially compressed configuration. The basket 152 may be formed with a plurality of apertures that are sized to prevent passage of both the leaflet clip 40 and other biological material that may break off from the procedure (e.g., about 100 microns to about 4 mm in diameter). The basket 152 can be of similar size to the previously discussed basket 102. The top opening of the basket 152 may also include a plurality of loops or passages 152B sized to allow passage of the cinching loop 106 so that the basket 152 can be closed during a procedure.

Construction of the polymer basket 152 can be completed using a braid, mesh, weave, knit, or via injection molding. Potential basket shape and material combinations are infinite, and only a few are described here. Choosing a polymer material that has high heat resistance, low moisture absorption, and is durable enough to be collapsed into the outer sheath multiple times is important. Silicone tends to meet all of these performance requirements the best. In the event the basket is made of a silicone, it could be molded into the basket shape as a standalone component, or molded directly onto a loop structure. If creating the basket from a flat sheet of silicone, it could be cut to a designed pattern, and stitched onto a loop, into the desired shape.

The size and spacing of the pores 152A can be adjusted, depending on the material selected. In general, the pore size may be smaller than either the length, width, or height of the heart valve therapy to avoid it embolizing through the basket after it has been cut free. Using a basket with very small pores may help with filtering and capturing any debris generated during the tissue cutting process. Designing a basket with pores also allows some blood to flow through it; this helps improve the operators control of the basket by minimizing the force applied to it from pumping blood (i.e., it minimizes the 'parachute effect'). A polymer basket could be constructed with eyelets or not; if there are eyelets as shown, it will be slidably mounted to the basket cinching loop. If there are no eyelets, it will be securely affixed to the basket cinching loop.

Figures 35, 36:
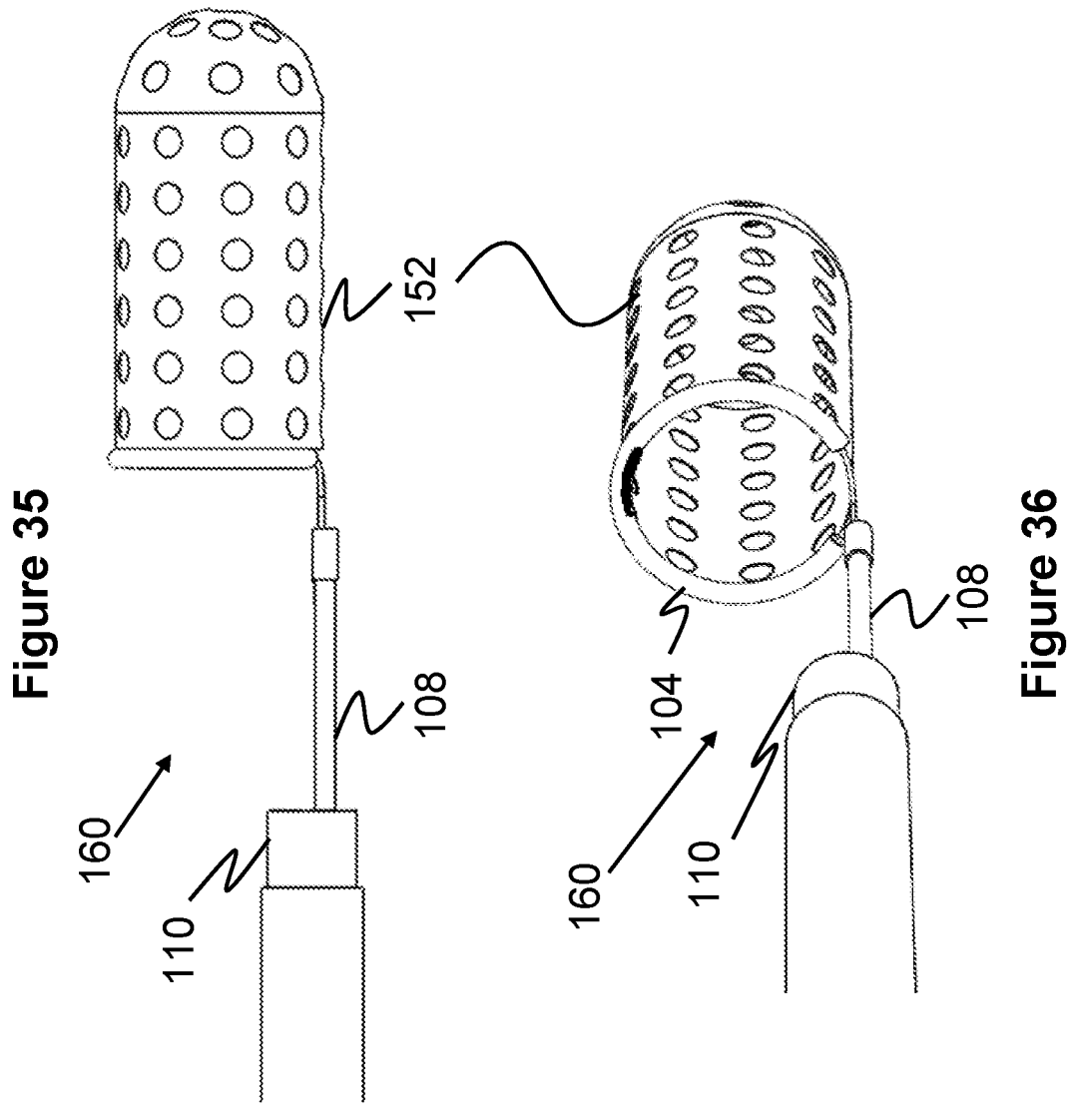
FIG. 35 illustrates a side perspective view of a removal catheter according to the present invention.
FIG. 36 illustrates a side perspective view of a removal catheter according to the present invention.

Since the polymer basket 152 does not conduct current, other embodiments are possible in which the cutting loop 104 of a removal catheter 160 also acts as a cinching loop, as seen in FIGS. 35 and 36. The basket 152 may be directly attached to the insulation portions 104A of the cutting loop 104 (or alternately may directly form the insulation portions around the uninsulated wire), leaving open the exposed, uninsulated portion 1046 that performs the leaflet cutting.

Figures 37, 38, 39:
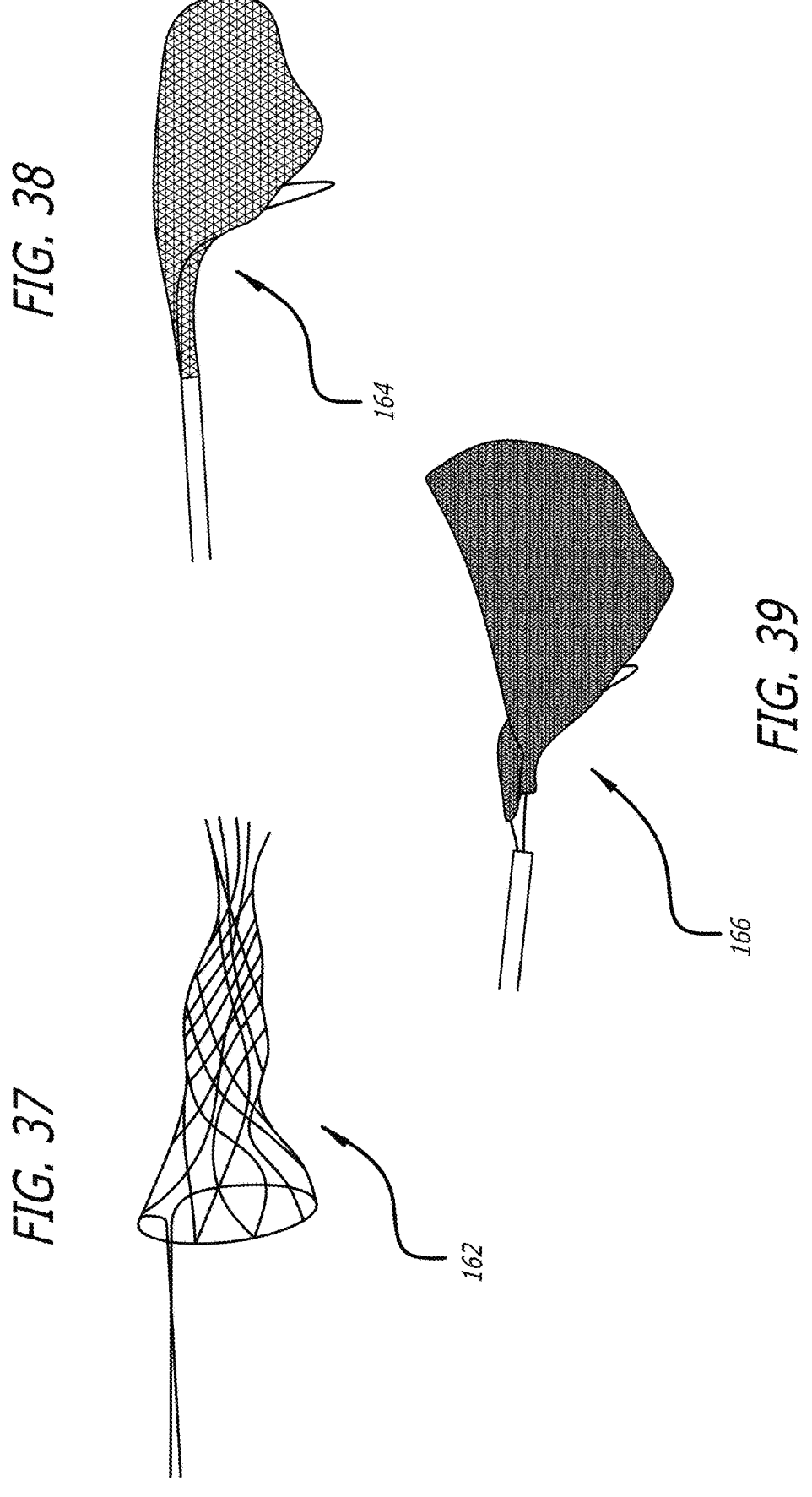
FIG. 37 illustrates a side view of a removal catheter according to the present invention.
FIG. 38 illustrates a side view of a removal catheter according to the present invention.
FIG. 39 illustrates a side view of a removal catheter according to the present invention.

Similar "single loop" embodiments are also possible with other shapes and materials. For example, FIG. 37 illustrates a plurality of polymer or fabric filaments braided together to form a flexible basket shape and relatively large apertures (e.g., about 0.5 mm to about 4 mm). FIG. 38 illustrates a plurality of polymer or fabric fibers woven into a fabric basket 164 with relatively smaller apertures (e.g., about 0.5 mm to about 4 mm). FIG. 39 illustrates a polymer sheet that is stitched to form a basket 166. In any of these embodiments, the cutting loop 104 can be exposed so that the uninsulated portion 1046 can cut through the valve leaflets after being cinched.

Figures 40, 41, 42, 43:
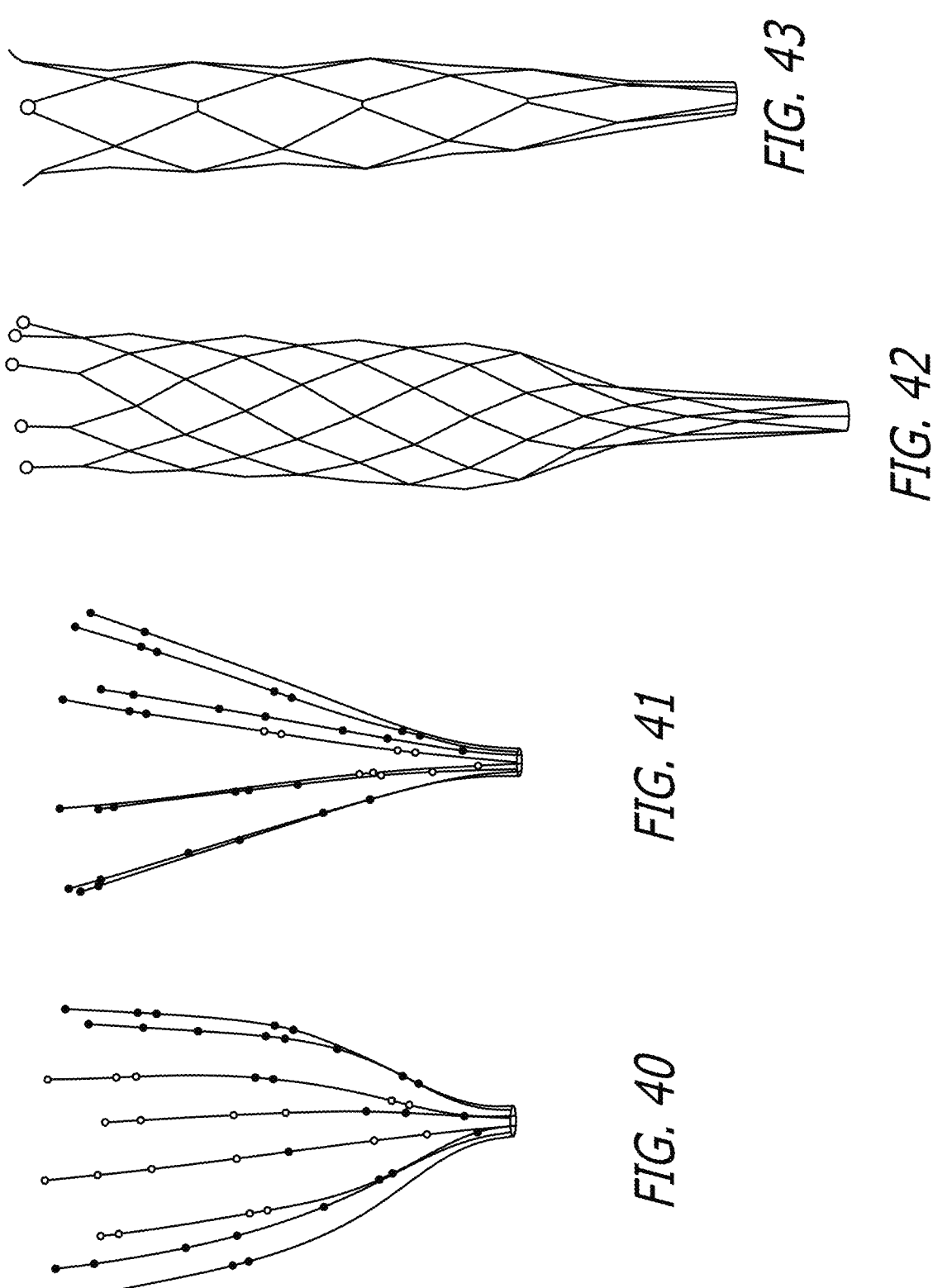
FIG. 40 illustrates a side view of a basket according to the present invention.
FIG. 41 illustrates a side view of a basket according to the present invention.
FIG. 42 illustrates a side view of a basket according to the present invention.
FIG. 43 illustrates a side view of a basket according to the present invention.

In other embodiments, the basket can be partially or fully composed of a laser cut basket. For example, FIGS. 40 and 41 illustrate a plurality of vertical, laser cut ribs with eyelet disposed along their length to allow for a plurality of wires or polymer filaments to be braided or woven through. FIGS. 42 and 43 illustrates laser cut basket shape that are entirely composed of a laser cut shape memory metal (e.g., a tube or sheet of shape memory metal).

The benefits of a laser cut basket are that its behavior/performance can be altered by changing the tube dimensions and/or cut pattern/density (i.e., basket pore size) while keeping the diameter and length of the basket fixed. The basket diameter and length design are primarily driven by the size of the intended heart valve therapy to be removed. The size, spacing, and number of laser-cut eyelets could also be adjusted and optimized. The material used preferably has shape memory properties, like Nitinol, to allow for the laser cut portion of the tube to be expanded and shaped. Using a material with shape memory is what enables the basket to collapse and open back up to the same shape, repeatedly. The wire size is preferably small enough to allow for it to be easily collapsed into and deployed from the delivery catheter during the procedure, but large enough to give the basket some rigidity such that it can adequately open in the presence of valve chordae or other structures.

Basket pore size can be varied in a laser cut design by changing the cut pattern to achieve the desired result. For example, pore sizes may vary within a range of about 100 microns to about 4 mm. In general, the pore size should be smaller than either the length, width, or height of the heart valve therapy to avoid it embolizing through the basket after it has been cut free. One unique benefit of a laser cut basket is that the pore size and spacing could vary throughout the basket length. For example, the proximal opening side of the basket could have large pores with a certain pattern density. The pore size and pattern density could get smaller and denser towards the distal end of the basket.

Any of the basket embodiments described in this specification can further include an outer covering to help collect any debris or embolic material freed during the procedure. Such an outer covering may include a solid or perforated polymer sheet, a woven fabric, a tubular shape formed from relatively small, finely braided metal wires, or similar materials. In one specific embodiment, the interior of the basket can have a nonconductive liner, film, or coating (e.g., silicone) on its inner surface to help prevent conduction with the cutting element 104.

Figure 44:
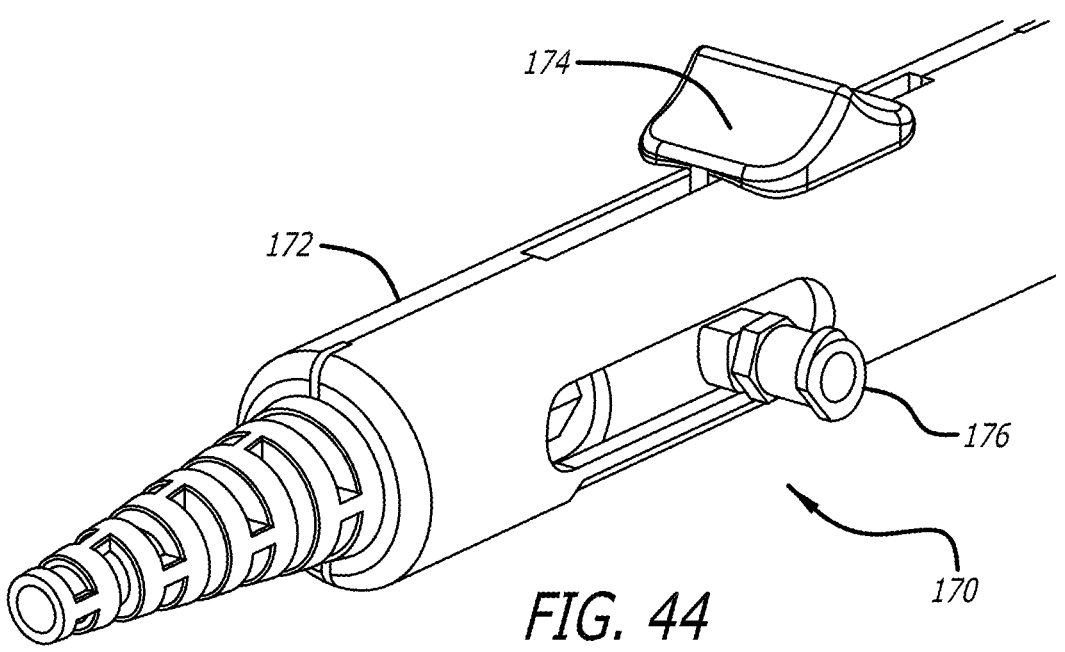
FIG. 44 illustrates a side view of a handle according to the present invention.
Figure 45:
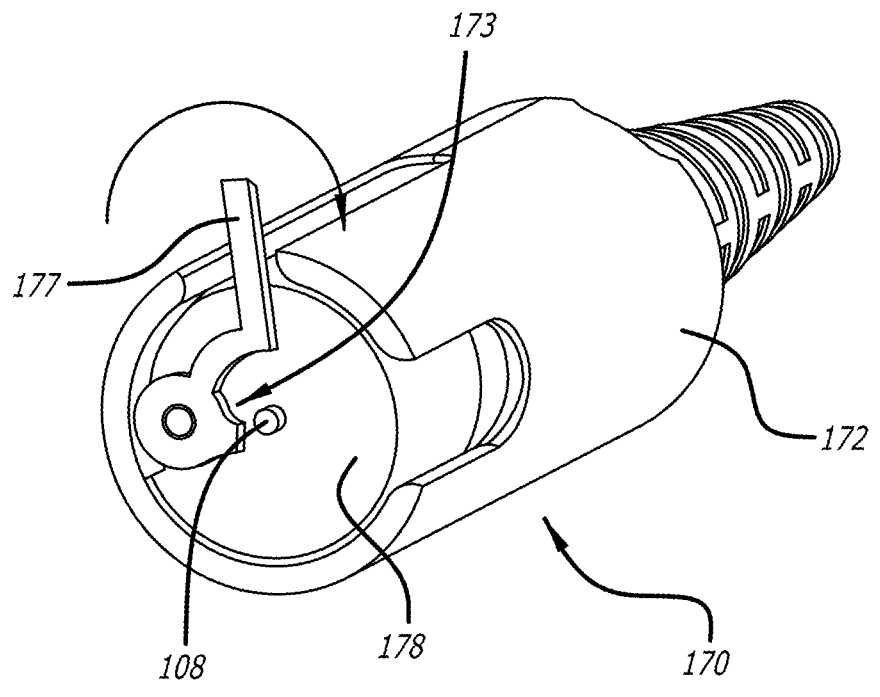
FIG. 45 illustrates a side view of a handle according to the present invention.

In one embodiment, the removal catheter 100 can include a proximal handle portion 170, as seen in FIGS. 44 and 45. The handle 170 includes an outer housing 172 and a sliding member 174 that is configured to slide within a longitudinal slot within the housing 172. The housing 172 can be connected to the outer tubular sheath 110 while the sliding member 174 is connected to the inner control member 108, thereby allowing the user to adjust the position of the sliding member 174 with their thumb to make a corresponding longitudinal move of the inner control member 108, basket 102, and cutting loop 106.

Optionally, the handle 170 may also include a fluid connection port 176 (e.g., a luer port) that is in communication with an interior of the interior passage of the outer tubular sheath 110 so that an electrically neutral solution (e.g., a dextrose solution) can be delivered to the area near the cutting loop, amplifying the tissue cutting effects and minimizing energy loss around the area to the blood pool. The amount and timing of this fluid can be determined by a physician (e.g., via a syringe) or via an electrically actuated pump mechanism based on a position of the cutting loop 106 (i.e., when the cutting loop is outside of the outer tubular sheath and in good contact with desired tissue 110).

As seen in FIG. 45, the handle 170 may also include a locking mechanism 173 near a distal end of the housing 172 which locks the inner control member 108 in place relative to the outer tubular sheath 110. For example, the locking mechanism 173 can include a handle 177 that is configured to rotate a cam member 178 that surrounds a proximal end of the inner control member 108. When the handle 177 rotates the member 178, the cam member 178 creates an interference fit with the inside of the housing 172, locking the control member 108 in its longitudinal position. When the handle 177 rotates the cam member 178 in the opposite direction, it releases the interference fit between the cam member 178 and the housing 172 to release the inner control member 108 so that it can longitudinally slide within the handle 170.

Figures 46, 47:
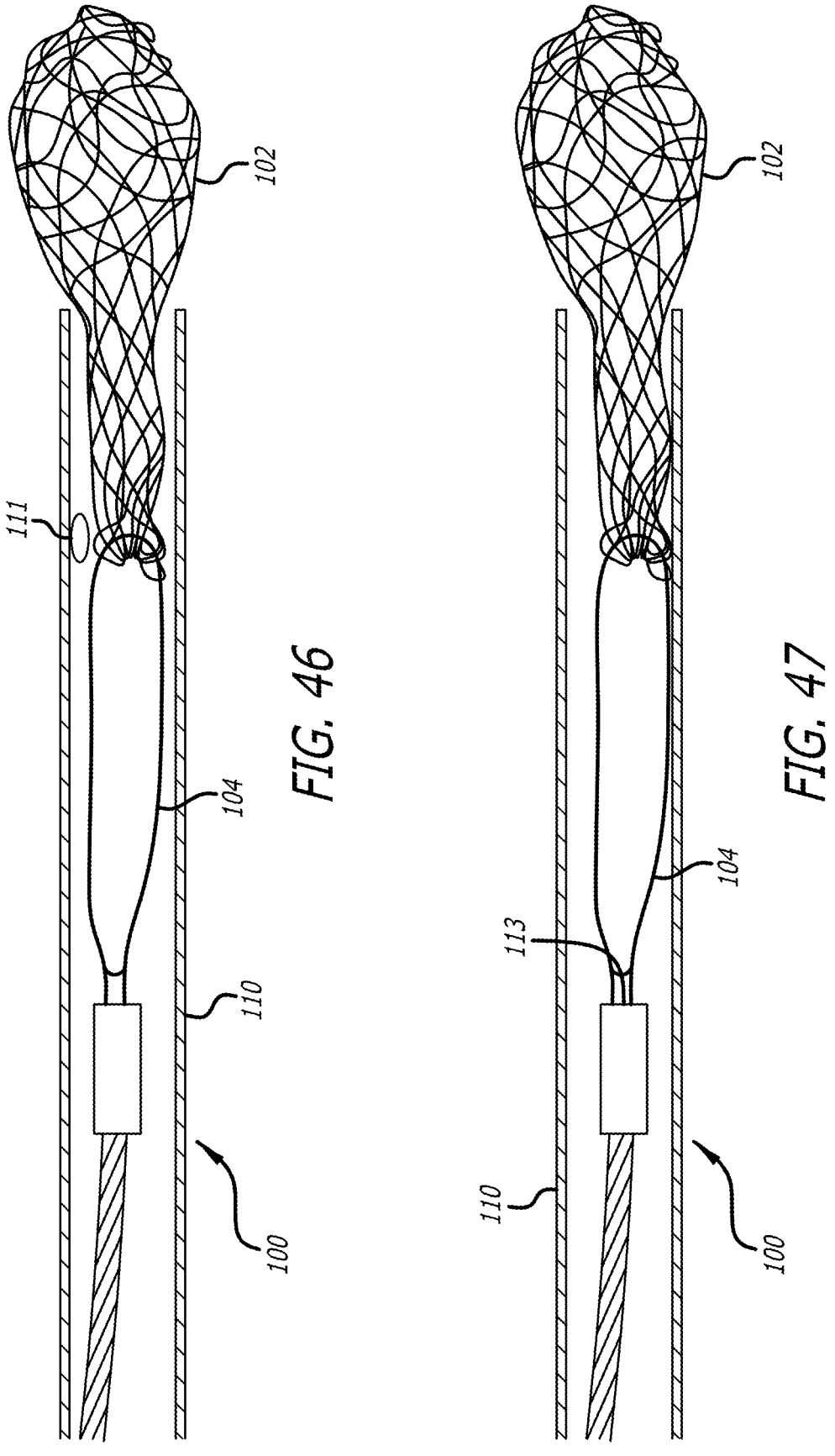
FIG. 46 illustrates a side view of a removal catheter according to the present invention.
FIG. 47 illustrates a side view of a removal catheter according to the present invention.

FIG. 46 illustrates an embodiment of the removal catheter 100 with a current over-flow hole 111 in the outer tubular sheath 110. This embodiment is most beneficial for an embodiment with a single cinch and cutting loop and either a polymer or minimally conductive basket 102. As the cutting element 104 and affixed basket 102 are retracted inside the outer tubular sheath 110 to begin cutting the leaflet tissue, the distal end of the outer tubular sheath 110 can become closed off from the blood pool. If this happens after the tissue has been cut, the current being delivered to the cutting element 104 is no longer being transferred to tissue or blood, and instead transfers the heat and/or electricity through the basket 102 and can damage it. The current overflow hole 111 in the outer tubular sheath 110 can ensure the cutting element 104 is always in communication with the blood pool, even after the cut has been completed. In this way, the current will choose to flow through the blood to the opposite RF electrode attached elsewhere on the patient, as opposed to the basket.

Alternately, a wire 113 can be attached to the inner control member 108 to ensure the current pathway always involves the blood pool, even after the cut has been completed. The wire 113 is preferably designed to be long enough to always protrude from the distal end of the outer tubular sheath 110, even with the basket 102 fully collapsed inside the outer tubular sheath 110. It would also preferably have a very small region of exposed metal at the very distal tip, and the rest would be insulated. In this way, when the cut is completed the current will choose to flow through the lower resistance wire and to the blood as opposed through the higher resistance basket 102 (e.g., silicone).

Figures 48, 49, 50:
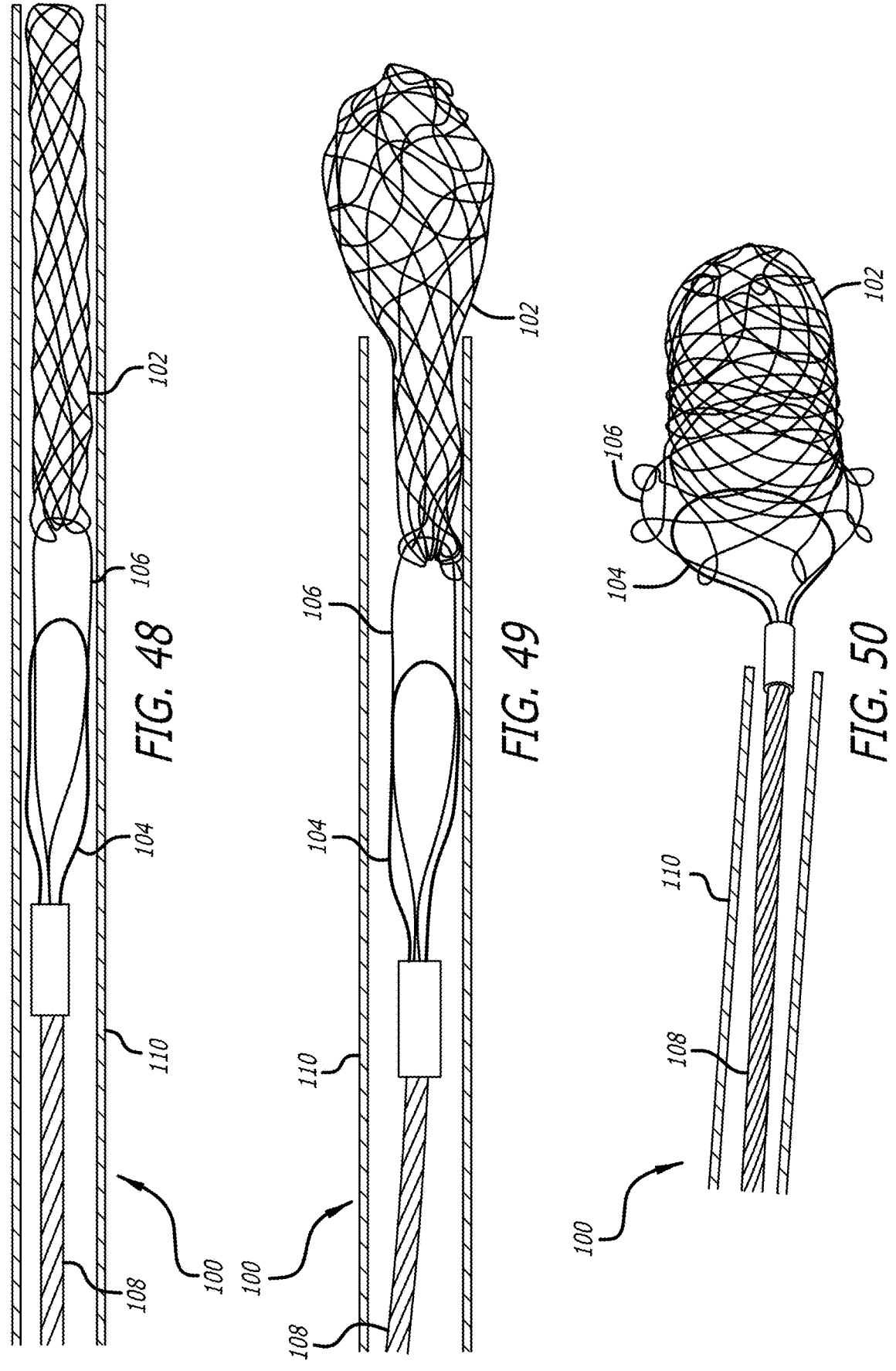
FIG. 48 illustrates a side view of a removal catheter according to the present invention.
FIG. 49 illustrates a side view of a removal catheter according to the present invention.
FIG. 50 illustrates a side view of a removal catheter according to the present invention.

FIGS. 48-53 illustrate side views of the removal catheter 100 deploying and cinching its basket 102. In FIG. 48, the basket 102, cinching loop 106, and cutting loop 104 are all located within the outer tubular sheath 110. As can be seen in this Figure, these components are radially compressed to a relatively smaller diameter to allow passage through the vessels of a patient (keeping them compressed in outer tubular sheath enables passage through smaller orifices and between multiple clips as well).

In FIG. 49, the inner control member 108 is distally advanced (e.g., via sliding member 174) so that the basket 102 begins to exit the outer tubular sheath 110 and radially expand. This distal movement continues until both the basket 102 and the cutting loop 104 have deployed and fully expanded outside the sheath 110, as seen in FIG. 50.

Figures 51, 52, 53:
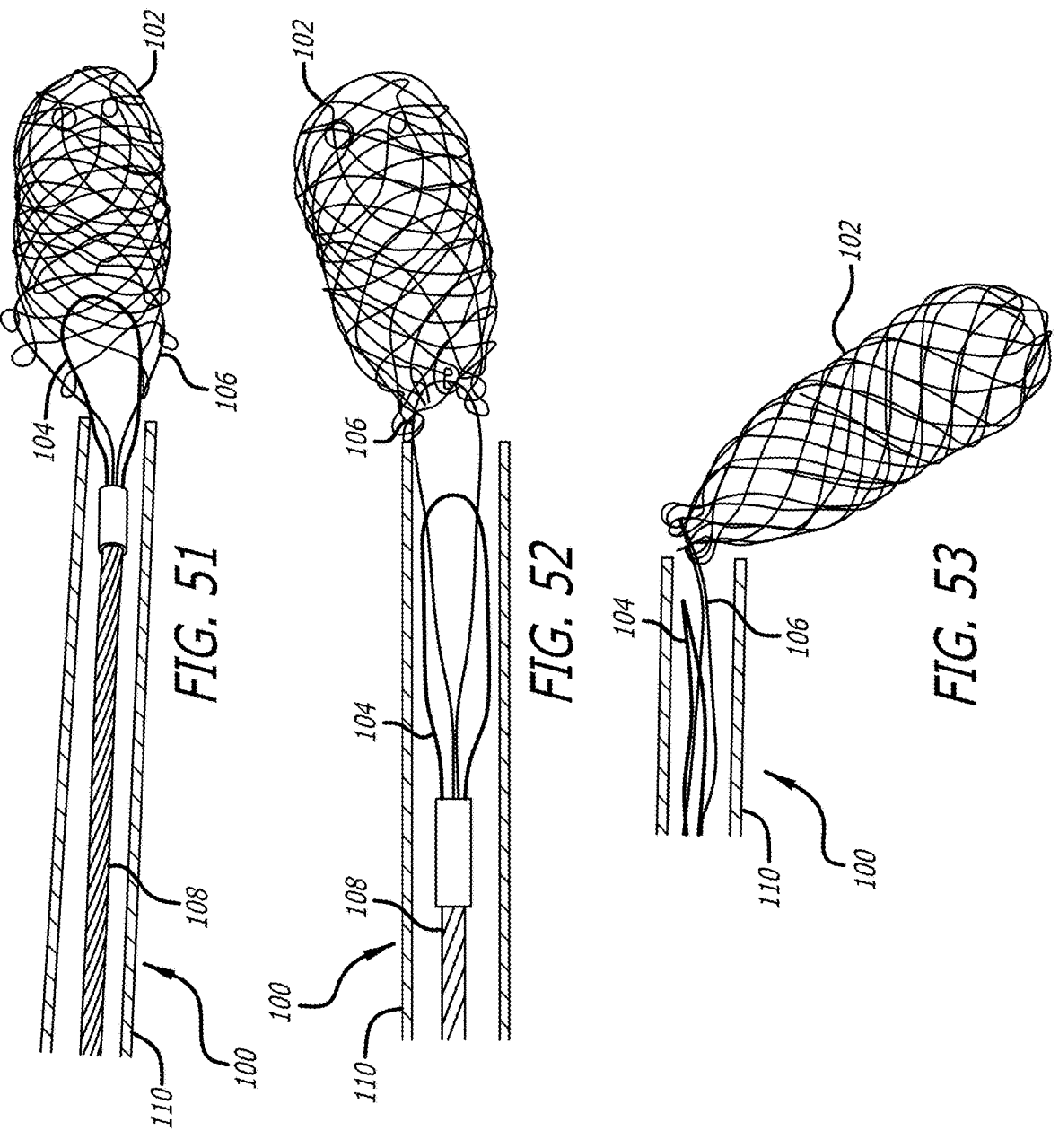
FIG. 51 illustrates a side view of a removal catheter according to the present invention.
FIG. 52 illustrates a side view of a removal catheter according to the present invention.
FIG. 53 illustrates a side view of a removal catheter according to the present invention.

FIGS. 51 and 52 illustrate the inner control wire 108 being retracted, causing both the cinching loop 106 and the cutting wire 104 to retract and radially close in diameter. Typically, RF energy will be activated during this time so that as the cutting wire 104 closes, it cuts the tissue of the leaflets. As the cutting loop 104 is fully pulled inside the outer tubular sheath 110, the RF current is deactivated. This can be achieved in a plurality of different ways. For example, the previously described sliding member 174 of the handle 170 may include a position switch that turns the RF energy on/off at a predetermined longitudinal position. Alternately, a manual on/off switch can be included on the handle 170 or RF power supply.

To assist in determining when to manually turn off the RF energy, a radiopaque marker can be placed at the distal end of the outer tubular sheath 110. As the physician performs the tissue bridge cut, they will have their eyes on the fluoroscopy screen. Since tissue is typically not visible on fluoroscopy, providing the operator with a visual indicator on the catheter 100 indicating that the tissue bridge has been cut may be useful. The inner control member 108 and cutting loop 104 are retracted into the sheath 110 during the cutting process and the radiopaque marker is located such that when the operator sees on fluoroscopy the entire cutting loop 104 on the proximal side of the radiopaque marker, the tissue bridge has been cut. Not only is this a useful visual indicator for the operator, but it also makes the procedure safer. Once the cutting loop 104 has passed the radiopaque marker, the RF cutting energy can be terminated immediately by the operator to prevent any unintended heating by applying power longer than necessary.

Finally, the opening of the basket 102 is nearly completely cinched closed and the positioned of the inner control member 108 may optionally be locked in place (e.g., with locking mechanism 173 on the handle 170). The basket 102 may be maintained outside of the outer tubular sheath 110 and pulled into a larger guide catheter used during the procedure.

The present invention includes different methods or approaches of removing a heart valve therapy such as a valve clip 40. For example, FIGS. 56-61 illustrate a removal procedure in which the atrial septum 18 is crossed to access the mitral valve 20. While example access methods and procedures are described, it should be understood that variations are possible based on known catheter access techniques. Additionally, these access techniques can be used with any of the embodiments of this specification.

Figures 54, 55:
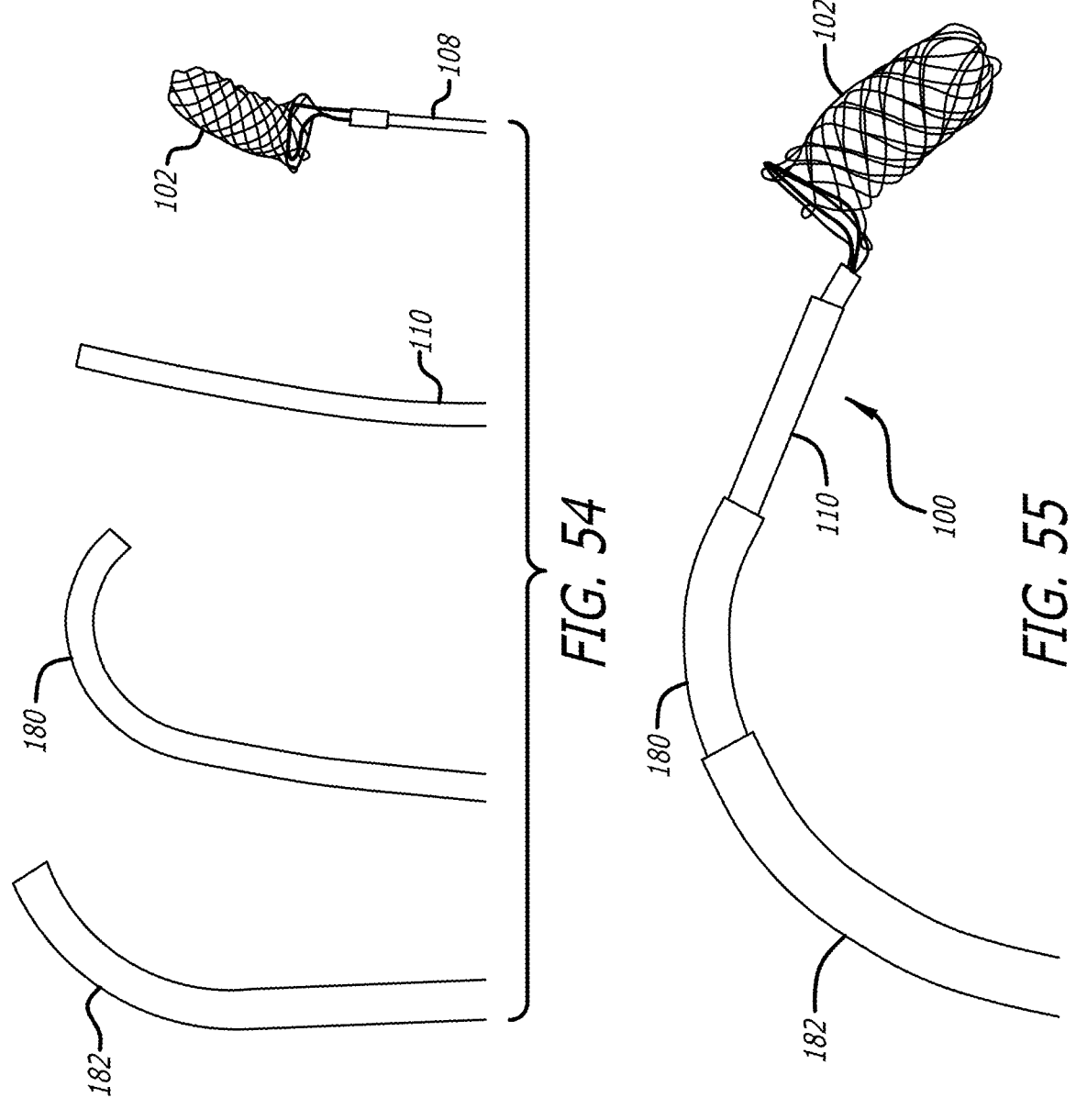
FIG. 54 illustrates a side view of a removal catheter and guide catheters according to the present invention.
FIG. 55 illustrates a side view of a removal catheter and guide catheters according to the present invention.

The mitral valve access procedure of FIGS. 56-61 may, in one embodiment, include an inner control member 108, an outer tubular sheath 110, an inner steerable catheter 180, and an outer transseptal guide catheter 182, which can be seen separately in FIG. 54 and together in FIG. 55 and are discussed further below. The three nested but independent curving and axially articulating catheters make it possible to position the removal device anywhere in the heart regardless of size or procedural positioning. However, other tools, sheaths, catheters, and similar devices may alternately be used to directed the removal catheter 100 as described below.

Figure 56:
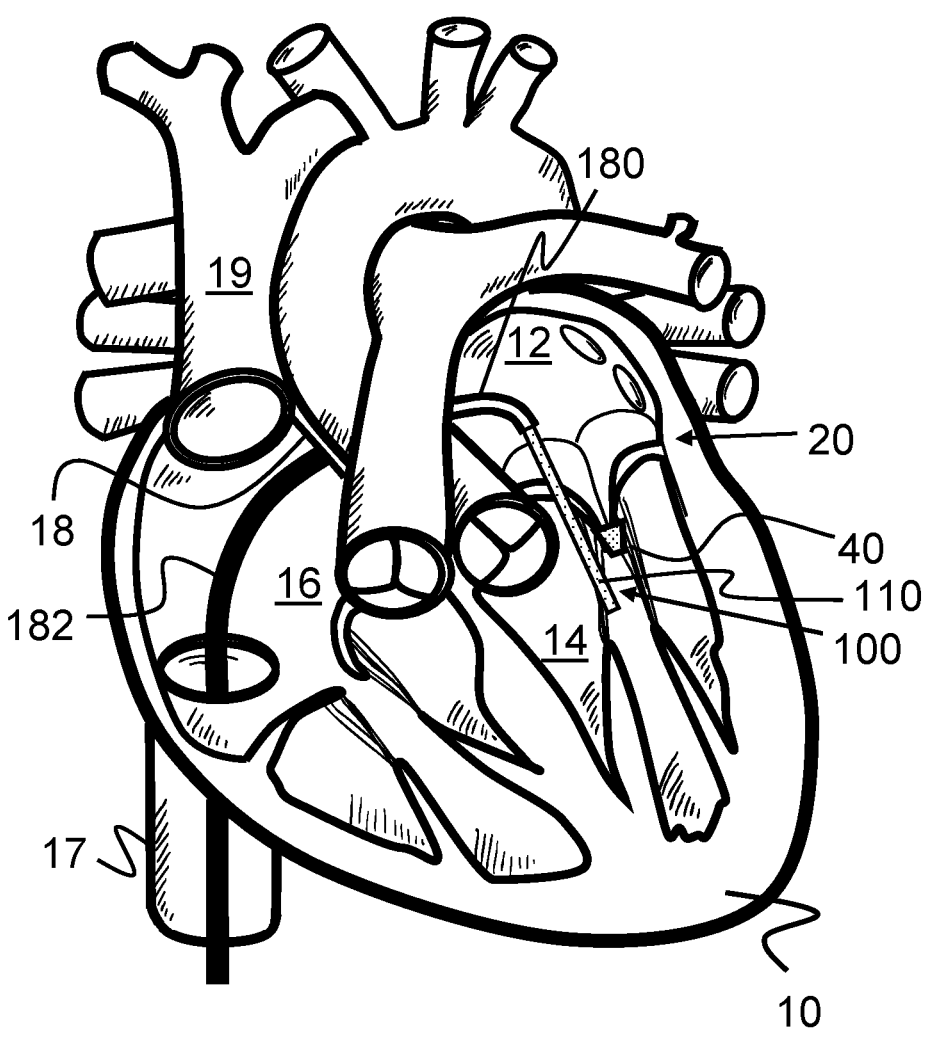
FIG. 56 illustrates a side view of a removal catheter procedure according to the present invention.

Turning first to FIG. 56, the left atrium 12 can be accessed by advancing a transseptal guidewire or needle to the atrial septum 18 (e.g., via the inferior vena cava 17 or the superior vena cava 19), using the guidewire to cross the atrial septum 18, and finally moving the guidewire into the left atrium. Next, a relatively larger diameter outer transseptal guide catheter 182 can be advanced over the guidewire and through the atrial septum 18 so the its distal end is located in the left atrium 12. Alternately, the transseptal guide catheter 182 can be advanced through the atrial septum 18 without the use of any transseptal guidewire. The outer transseptal guide catheter 182 may optionally have a predetermined curve or bend that may help angle it from the inferior vena cava 17 towards the atrial septum 18.

The guidewire can be removed and the inner steerable guide catheter 180 can then be advanced through the outer transseptal guide catheter 182 so that its distal end is located within the left atrium 12. The distal end of the inner steerable guide catheter 180 can be "steered" or deflected so that its distal opening is directed toward a desired location of the mitral valve 20. Since the guide catheter is independent of the outer transseptal guide catheter 182, the physician has the ability to direct the inner steerable guide catheter 180 to any location along the mitral valve 20, such that it can be rotated, advanced/retracted, or have the degrees of deflection altered while keeping the outer transseptal guide catheter 182 in the same location.

Figure 6:
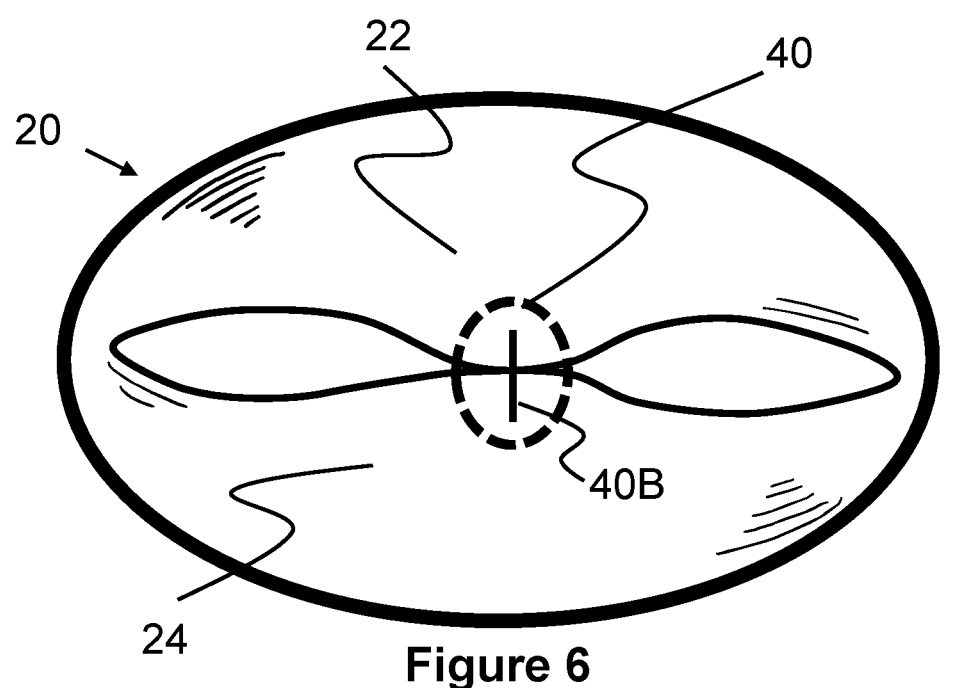
FIG. 6 illustrates a top view of a procedure to implant a leaflet heart valve therapy device.
Figures 7, 8:
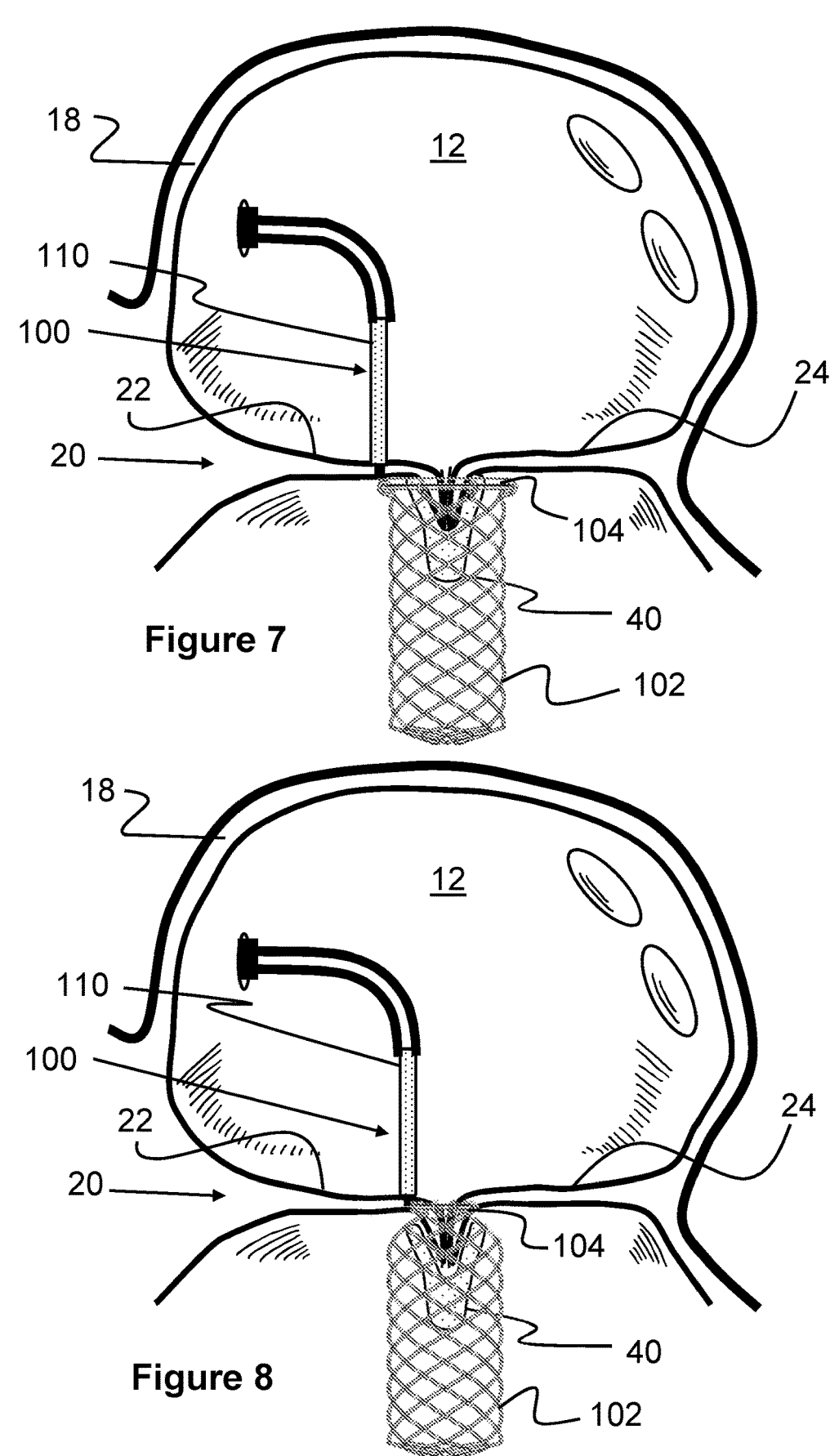
FIG. 7 illustrates a side view of a removal catheter according to the present invention.
FIG. 8 illustrates a side view of a removal catheter according to the present invention.

In the example of a mitral valve 20 having a leaflet clip 40, the inner steerable guide catheter 180 is preferably pointed towards either of the two valve openings on each side of the center clip 40 (see top view of FIG. 6). Once pointed at the desired target location, the removal catheter 100 is advanced through the inner steerable guide catheter 180 and out its distal end, into the left atrium 12, through one of the side openings of the mitral valve 20, and into the left ventricle 14, as seen in FIG. 56.

Figure 57:
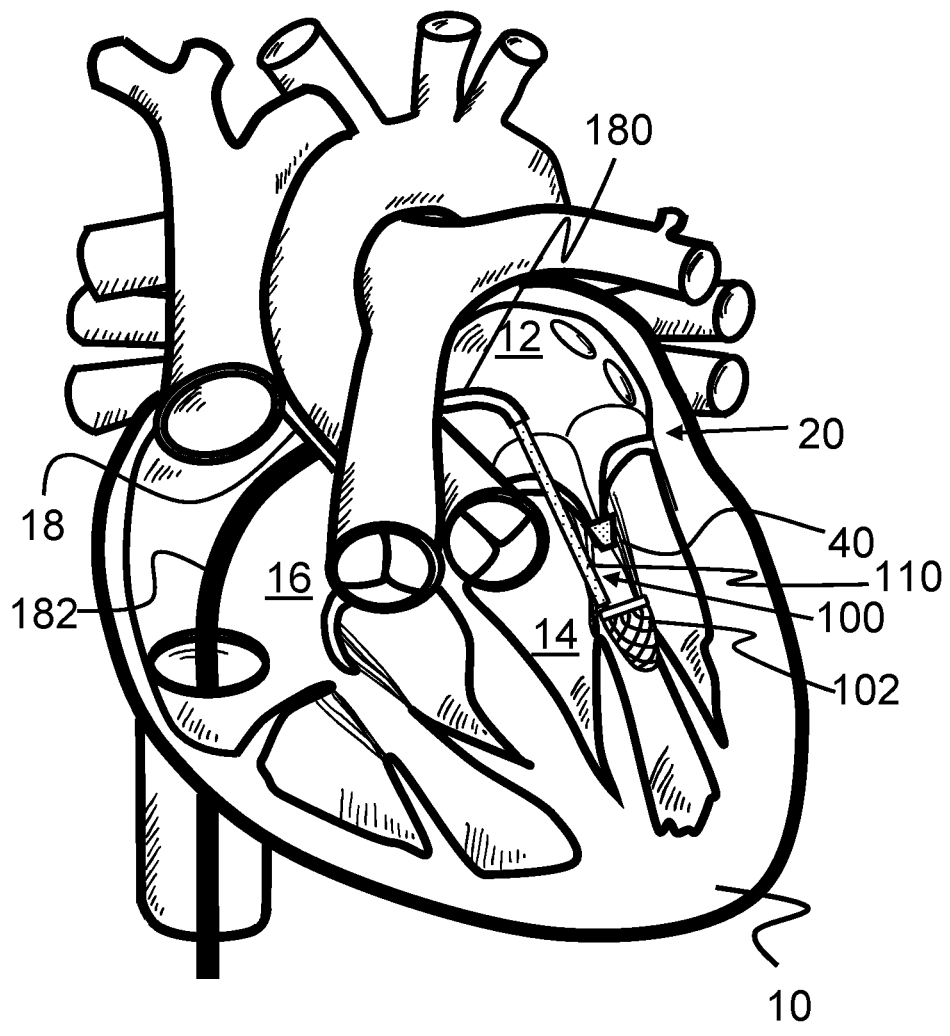
FIG. 57 illustrates a side view of a removal catheter procedure according to the present invention.
Figure 58:
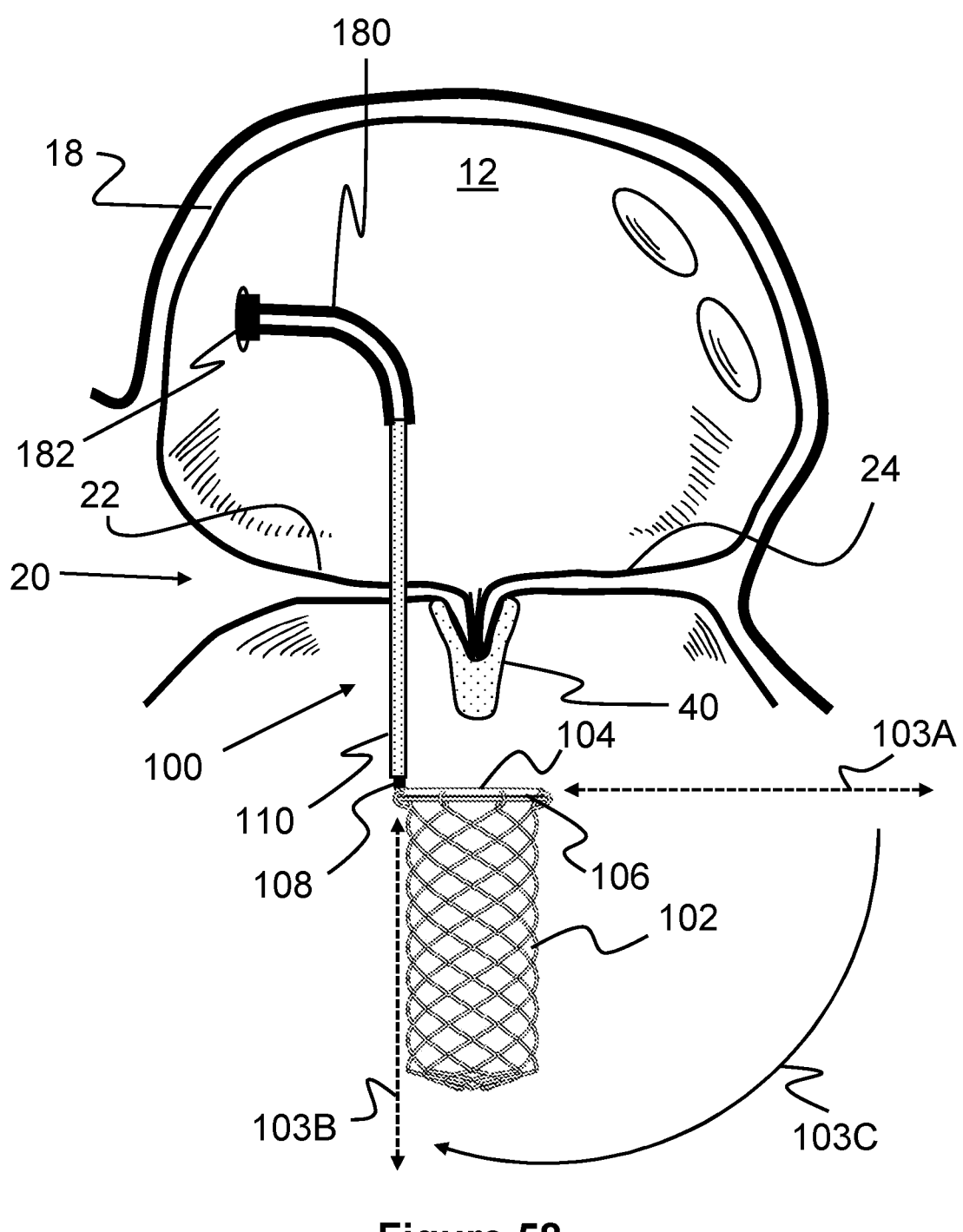
FIG. 58 illustrates a side view of a removal catheter procedure according to the present invention.

As seen in FIGS. 57 and 58, the inner control member 108 is distally advanced through the outer tubular sheath 110 of the removal catheter 100, causing the capture basket 102, cinching loop 106, and the cutting loop 104 to be advanced out of the outer tubular sheath 110. Preferably the capture basket 102, cinching loop 106, and the cutting loop 104 are connected to the inner control member 108 so that they expand to an orientation in which the opening of the basket 102 and the opening of the cutting loop 104 are directed or point towards the leaflet clip 40. For example, the plane 103A of the opening of the basket 102 and the opening of the cutting loop 104 may be an angle 103C between 45 degrees and 135 degrees relative to an axis 103B of the inner control member 108 (e.g., 90 degrees). The inner control member 108 can be rotated relative to the outer tubular sheath 110 (or alternately the entire removal catheter 100 can be rotated) to cause the capture basket 102, cinching loop 106, and the cutting loop 104 to also rotate within the left ventricle 14. In this manner, the physician can align or orient the basket 102 to a desired location directly beneath the leaflet clip 40.

Figure 59:
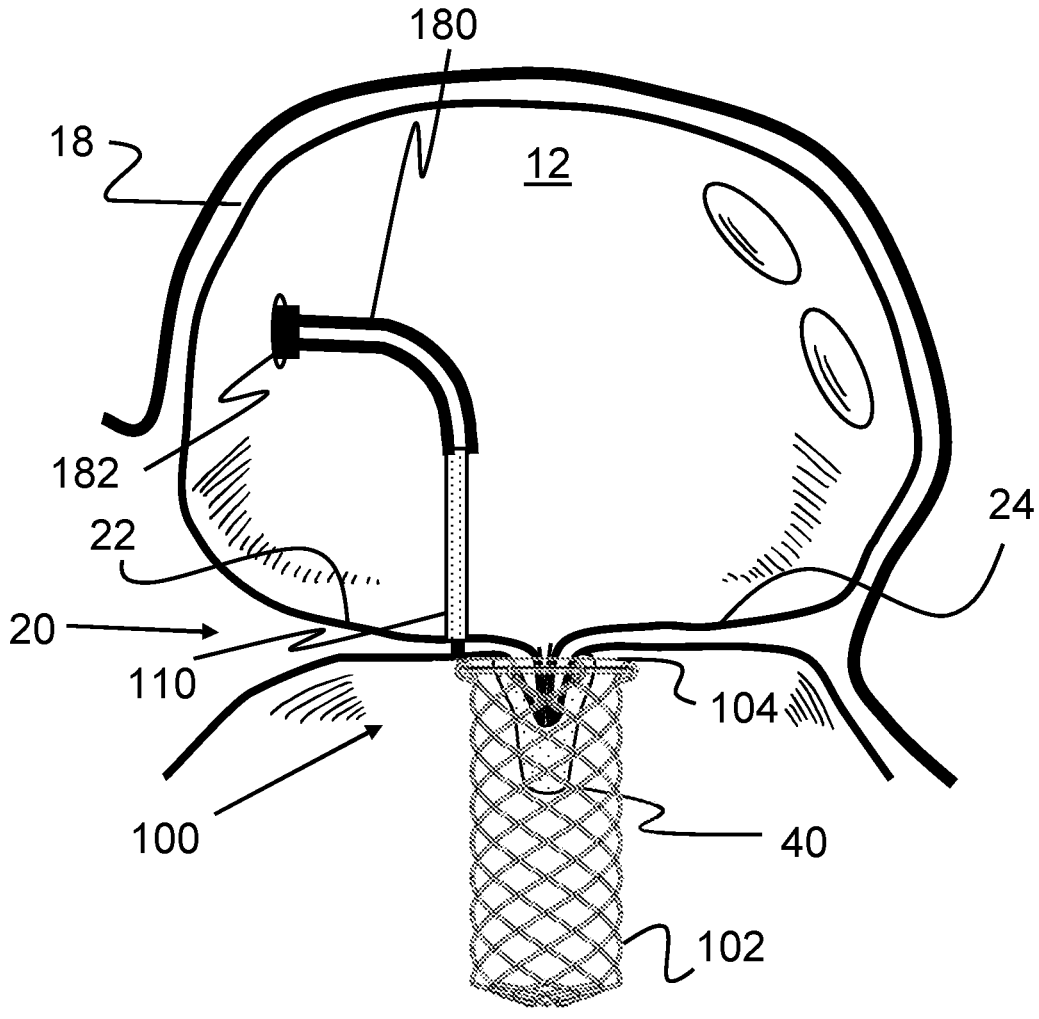
FIG. 59 illustrates a side view of a removal catheter procedure according to the present invention.

Once the capture basket 102, cinching loop 106, and the cutting loop 104 are deployed, the inner control member 108 (or alternately the outer tubular sheath 110) can be proximally withdrawn so that the leaflet clip 40 is positioned inside of the basket 102, as seen in FIG. 59. Preferably, both the cutting loop 104 and the cinching loop 106 are positioned above the leaflet clip 40; that is between the leaflet clip 40 and the bottom adjacent surfaces of the leaflets 22 and 24.

Figure 60:
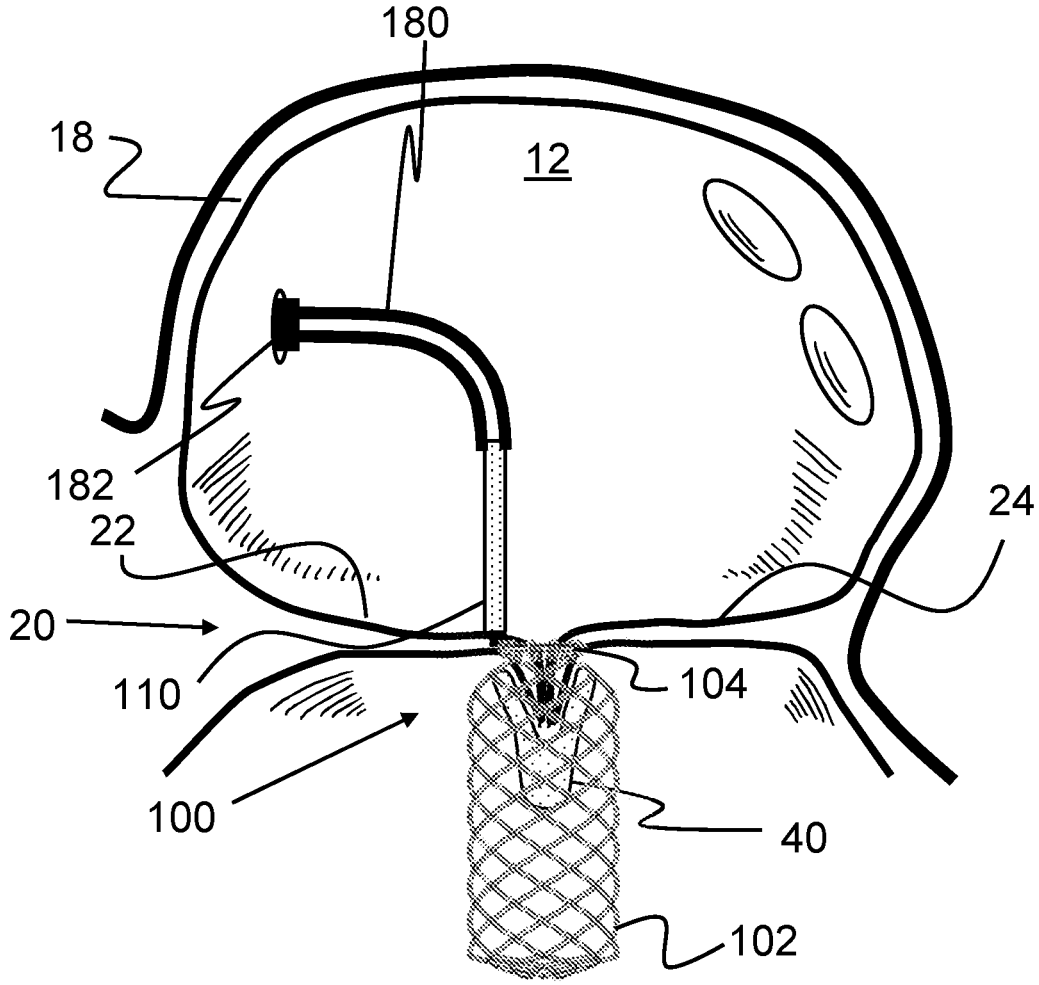
FIG. 60 illustrates a side view of a removal catheter procedure according to the present invention.

Turning to FIG. 60, the inner control member 108 is proximally retracted so as to partially retract the cinching loop 106 and the cutting loop 104. This causes the top opening of the basket 102 to close in diameter above the leaflet clip 40 and also causes the cutting loop 104 to reduce diameter and engage between an atrial side portion of the leaflets 22, 24 and the leaflet clip 40.

Figure 61:
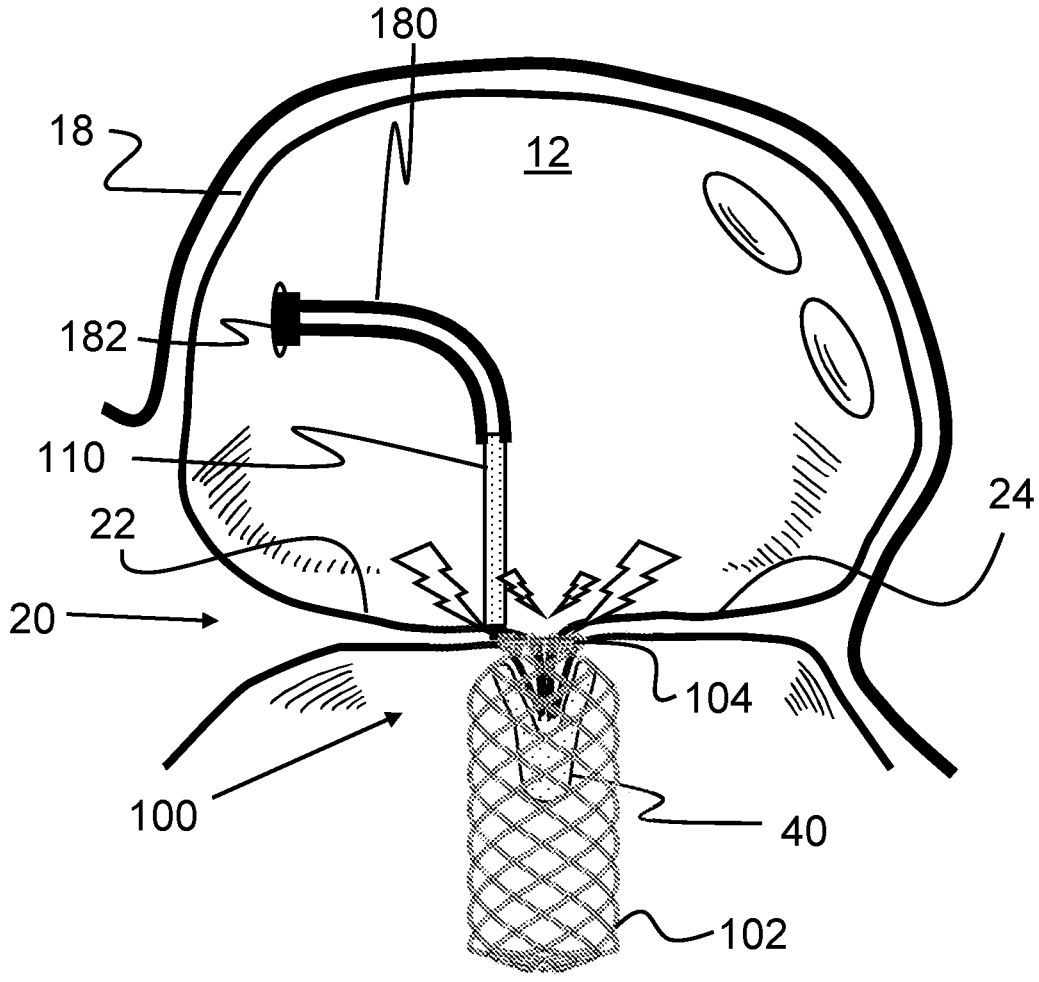
FIG. 61 illustrates a side view of a removal catheter procedure according to the present invention.

As seen in FIG. 61, as the cutting loop 104 is proximally withdrawn and decreased in diameter, RF energy is applied to the cutting loop 104. The uninsulated portion 104B presses against portions of the leaflets 22 and 24 nearest to the leaflet clip 40, thereby cutting this tissue and freeing the leaflet clip 40 from the mitral valve 20. The RF energy is turned off to the cutting loop 104. Preferably, the outer transseptal guide catheter 182 has a large enough diameter to allow the basket 102 containing the leaflet clip 40 within it. However, the removal catheter 100, inner steerable catheter 180, and outer transseptal guide catheter 182 can all be withdrawn from the patient as a single unit, if necessary.

It is further contemplated that, after removal of the leaflet clip 40, an artificial valve may be installed at the location of the mitral valve 20. If a guidewire is used during the removal procedure, it can also be used to advance and orient a valve delivery catheter to delivery and implant the artificial valve. One example of such an artificial valve replacement can be found in U.S. Pat. No. 8,579,964, entitled Transcatheter Mitral Valve Prosthesis, the content of which is hereby incorporated by reference.

It is further contemplated that, after removal of the leaflet clip a blood flow management apparatus such as a spacer, catheter, balloon, or other device is in and could be expanded in the location of the valve to manage the flow across the valve until such time as additional therapy could be delivered such as a replacement valve.

Figure 62:
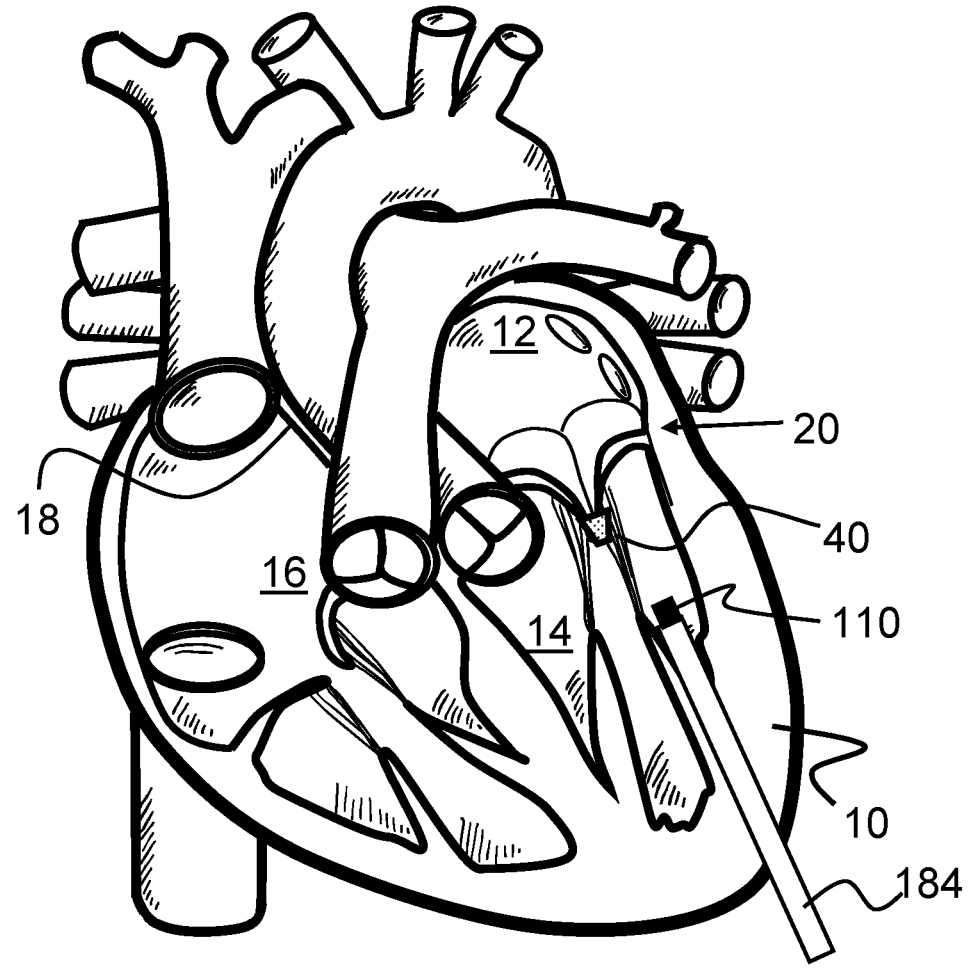
FIG. 62 illustrates a side view of a removal catheter procedure according to the present invention.

FIGS. 62-65 illustrate another method of removing a leaflet positioning device such as a leaflet clip 40 via a transapical approach. First, an incision is made in the sternum (e.g., between the manubrium and the sternum) and a transapical sheath 184 is advanced through the incision, through the apex of the heart 10, and into the left ventricle 14, as seen in FIG. 62. The removal catheter 100 is then advanced through the transapical sheath 184 so that a distal end of the outer tubular sheath 110 extends out into the left ventricle 14.

Figure 63:
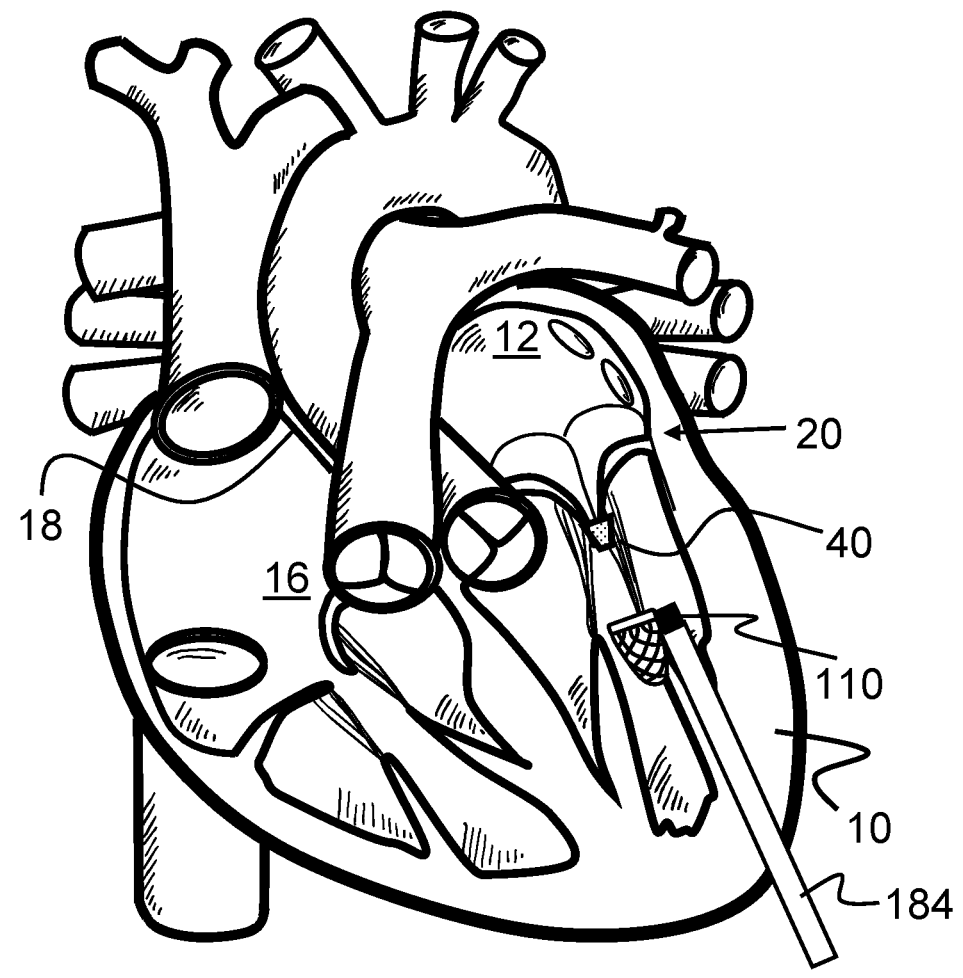
FIG. 63 illustrates a side view of a removal catheter procedure according to the present invention.

Turning to FIG. 63, the inner control member 108 is distally advanced within the outer tubular sheath 110 so as to release and expand the basket 102 and cutting loop 104 into the left ventricle 14. The cinching loop 106 and the cutting loop 104 preferably have a predetermined bend (e.g., a heat set bend/curve) that orients the top opening of the basket 102 and the opening of the cutting loops 104 towards the leaflet clip 40. For example, the plane of the top opening of the basket 102 and the opening of the cutting loops 104 can be within a range of 135 degrees to 225 degrees (e.g., about 180 degrees) relative to an axis of the inner control member 108. The inner control member 108 can be further rotated (or the entire removal catheter 100 can be rotated) by the physician so as to best align the cutting loop 104 and basket 102 with the leaflet clip 40.

Figure 64:
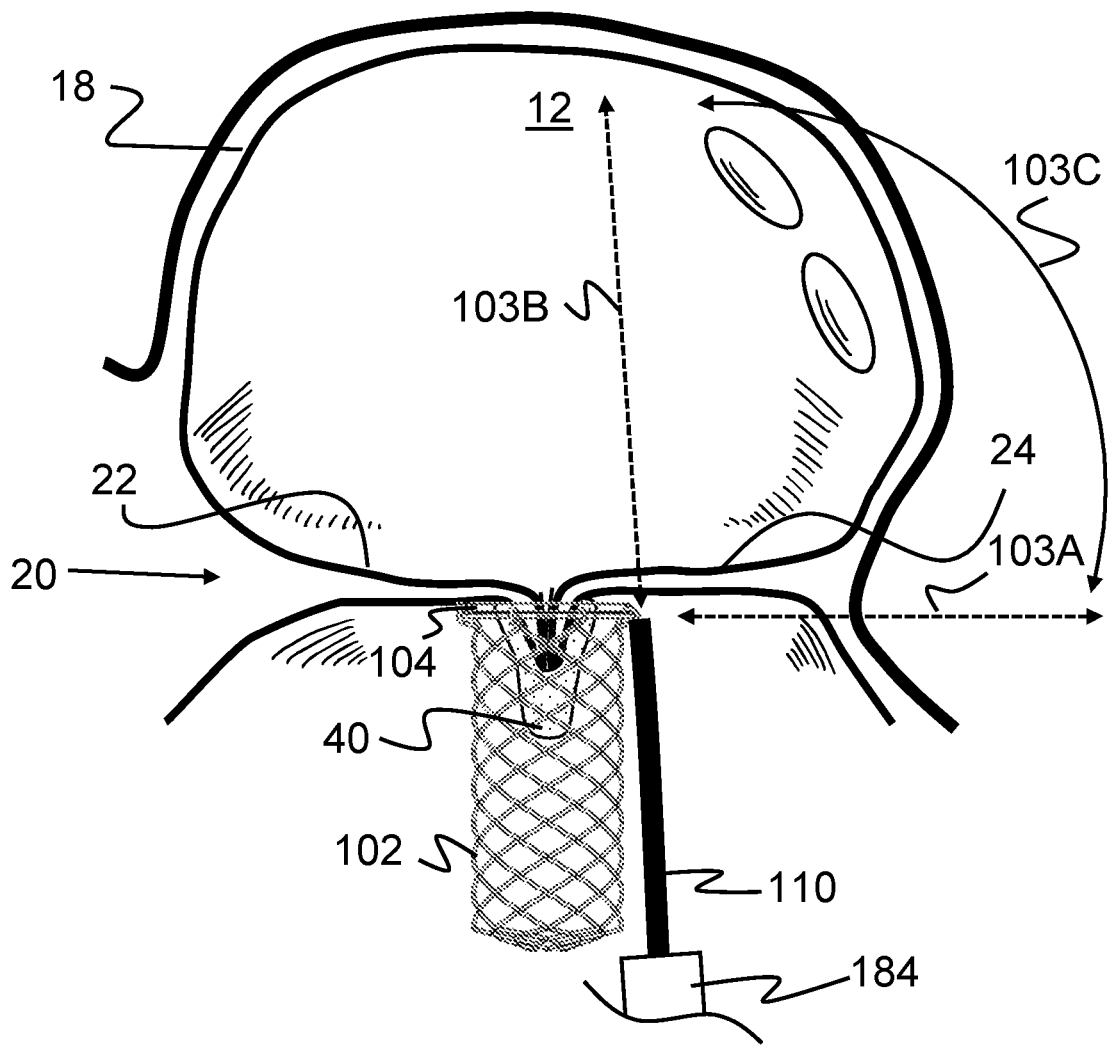
FIG. 64 illustrates a side view of a removal catheter procedure according to the present invention.
Figure 65:
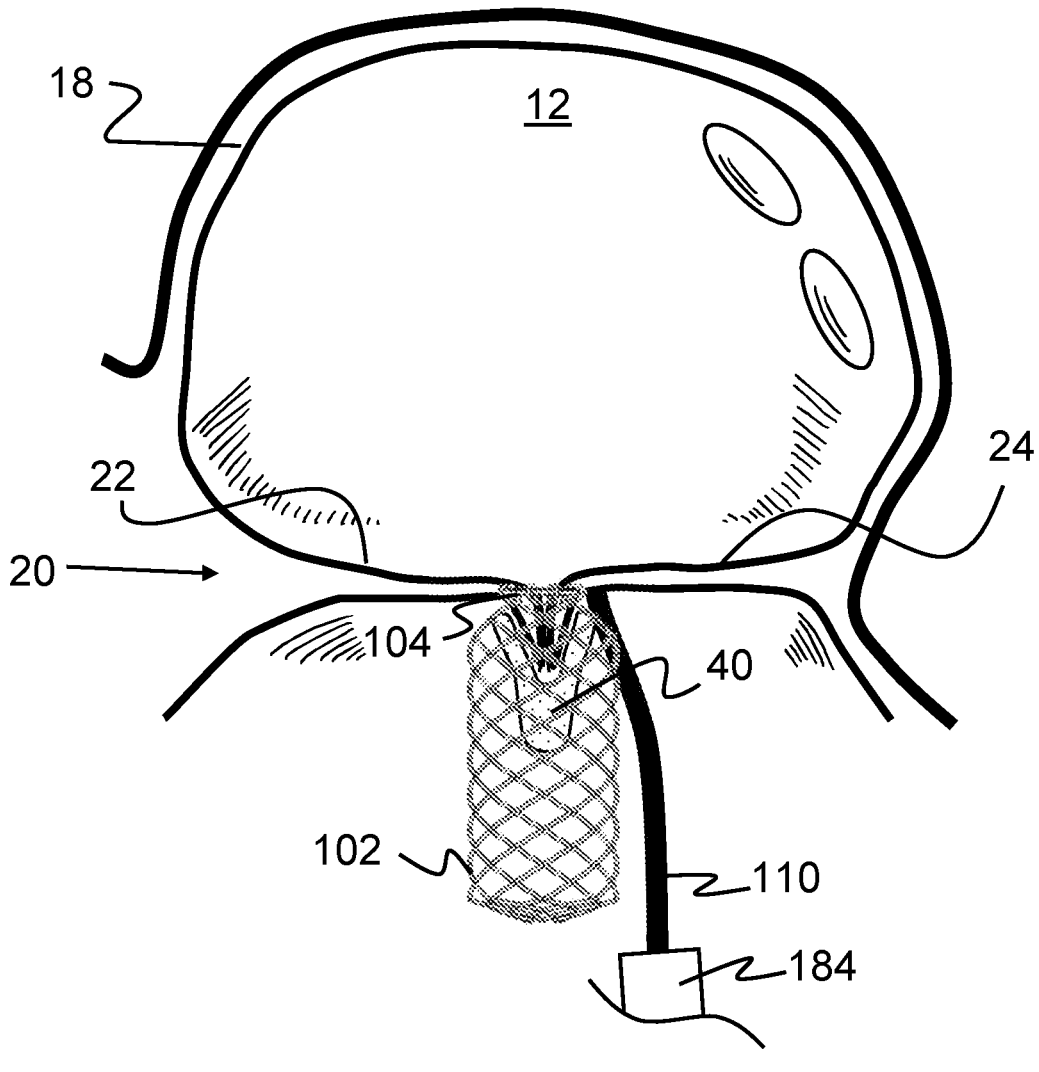
FIG. 65 illustrates a side view of a removal catheter procedure according to the present invention.

As seen in FIG. 64, the outer tubular sheath 110 is further advanced out of the transapical sheath 184 so that the leaflet clip 40 is positioned completely within the basket 102. As seen in FIG. 65, the inner control member 108 is proximally retracted to cause the cinching loop 106 and the cutting loop 104 to decrease in diameter. As the loops 104 and 106 decrease in diameter, the top opening of the basket 102 decreases, trapping the leaflet clip 40 within it. Additionally, as the cutting loop 104 decreases, RF energy is activated and delivered to the loop 104, allowing the uninsulated portion 104B to cut through the leaflet tissue immediately above the leaflet clip 40.

Preferably the capture basket 102, cinching loop 106, and the cutting loop 104 are connected to the inner control member 108 so that they expand to an orientation in which the opening of the basket 102 and the opening of the cutting loop 104 are directed or point towards the leaflet clip 40. For example, the plane 103A of the opening of the basket 102 and the opening of the cutting loop 104 may be an angle 103C between 25 degrees and 135 degrees relative to an axis 103B of the inner control member 108 (e.g., 90 degrees).

If the transapical sheath 184 has a large enough diameter, the outer tubular sheath 110 can be proximally retracted and the basket 102 containing the leaflet clip 40 is withdrawn into the passage of the transapical sheath 184 for removal. If the basket 102 and leaflet clip 40 are too large for the transapical sheath 184, both the sheath 184 and the removal catheter 100 can be pulled out together simultaneously.

Figure 66:
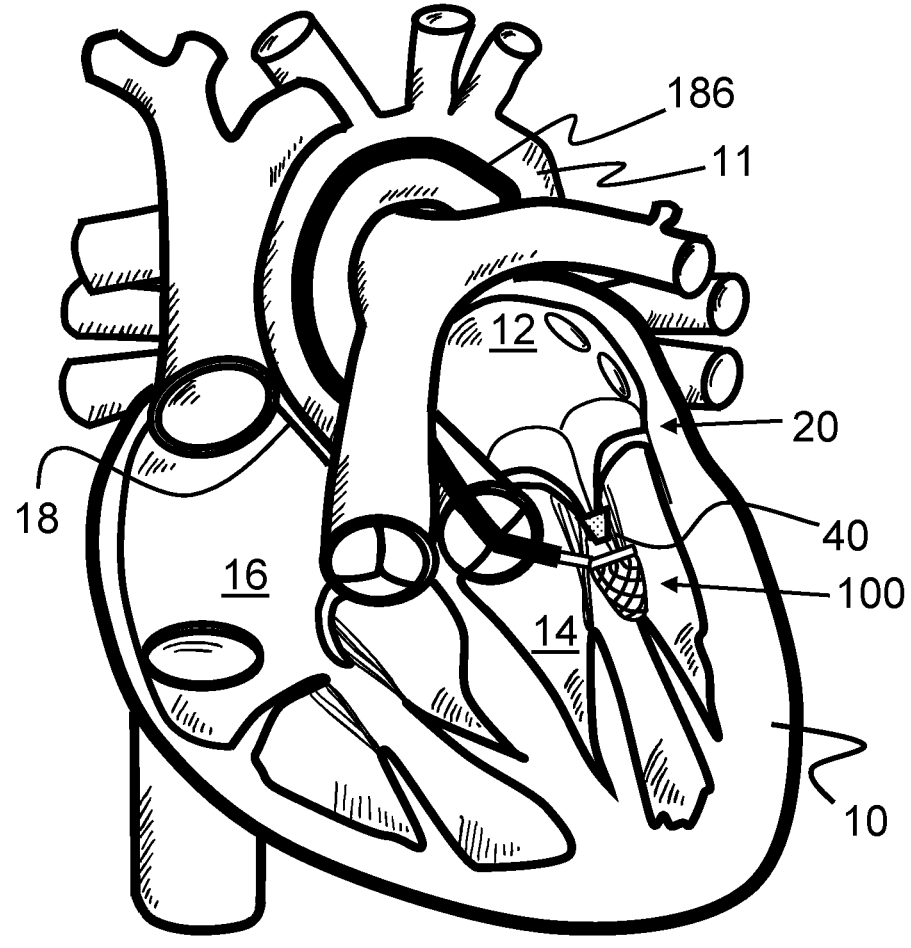
FIG. 66 illustrates a side view of a removal catheter procedure according to the present invention.
Figure 67:
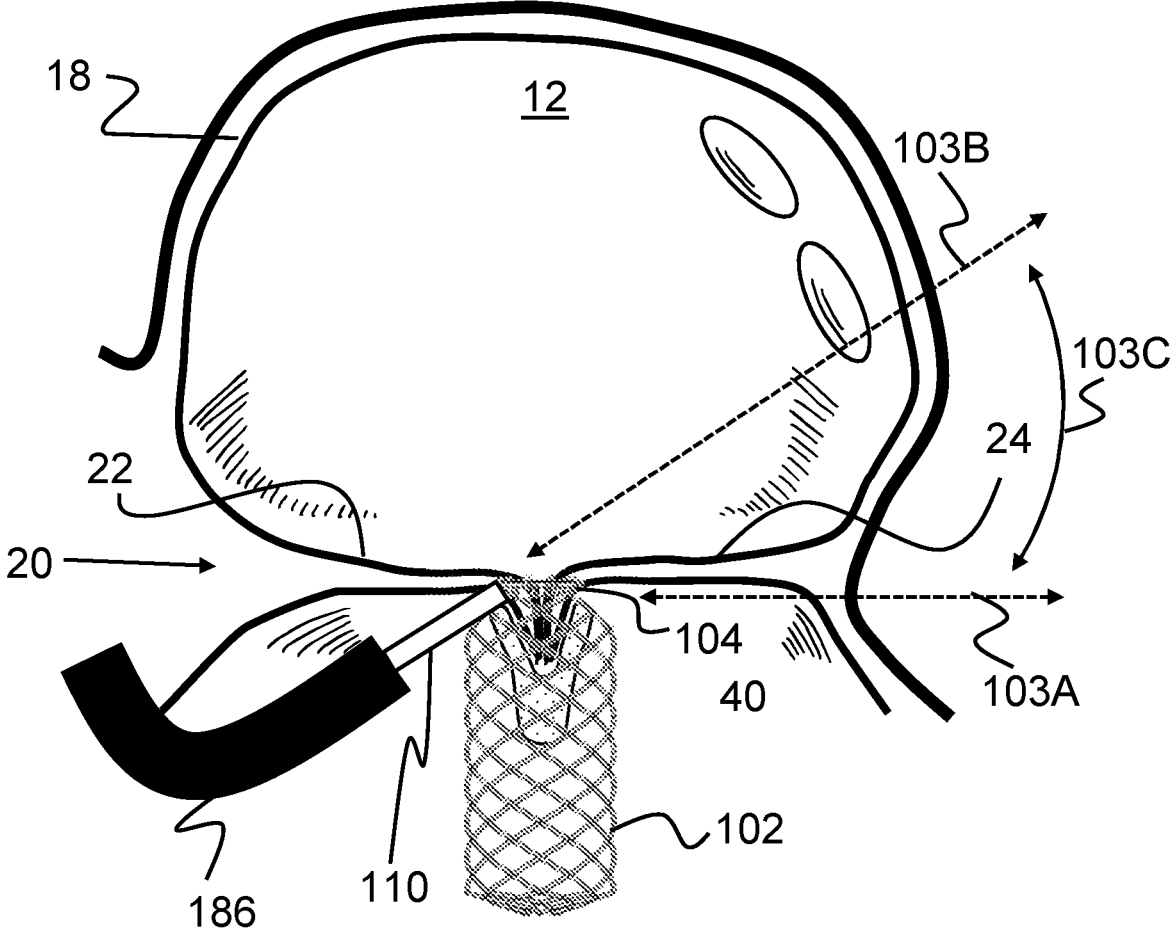
FIG. 67 illustrates a side view of a removal catheter procedure according to the present invention.

FIGS. 66 and 67 illustrate another method of removing a heart valve therapy such as a leaflet clip 40 via a transaortic approach. Referring to FIG. 66, an aortic guide catheter 186 is first positioned into the aorta 11 and advanced into the left ventricle 14. The aortic guide catheter 186 may have a fixed curve/shape that helps the physician direct the distal end of the catheter 186 beneath the leaflet clip 40. Alternately or additionally, the aortic guide catheter 186 may include steerable mechanisms to allow deflection in different directions.

Next, the removal catheter 100 is advanced through the aortic guide catheter 186 so that a distal end of the outer tubular sheath 110 extends from the distal end of the catheter 186 and into the left ventricle 14. The inner control member 108 is further distally advanced relative to the outer tubular sheath 110 so that the basket 102 and cutting loop 104 are deployed, expanded, and positioned in the left ventricle 14. The opening of the basket 102 and the opening of the cutting loop 104 are both or oriented so that they face the leaflet clip 40. For example, the face of the opening of the basket 102 and the opening of the cutting loop 104 may be within a range of about 300 degrees and 45 degrees relative to an axis of the inner control member 108 (e.g., about 320 degrees).

Referring to FIG. 67, the aortic guide catheter 186 is either moved or deflected (in the case of a steerable catheter) so that the cutting loop 104 and basket 102 are positioned over the leaflet clip 40. The inner control member 108 is proximally retracted inside 110, causing the cinching loop 106 and the cutting loop 104 to decrease in diameter, closing the top opening of the basket 102. As the cutting loop 104 decreases in diameter, RF energy is delivered to the loop 104, allowing the uninsulated portion 104 to cut areas of the leaflet tissue adjacent to the leaflet clip 40 and thereby freeing the leaflet clip 40 from the mitral valve 20. The basket 102 and leaflet clip 40 can either be retracted through the aortic guide catheter 186 or all of the catheters can be removed together as a single unit simultaneously.

Figure 68:
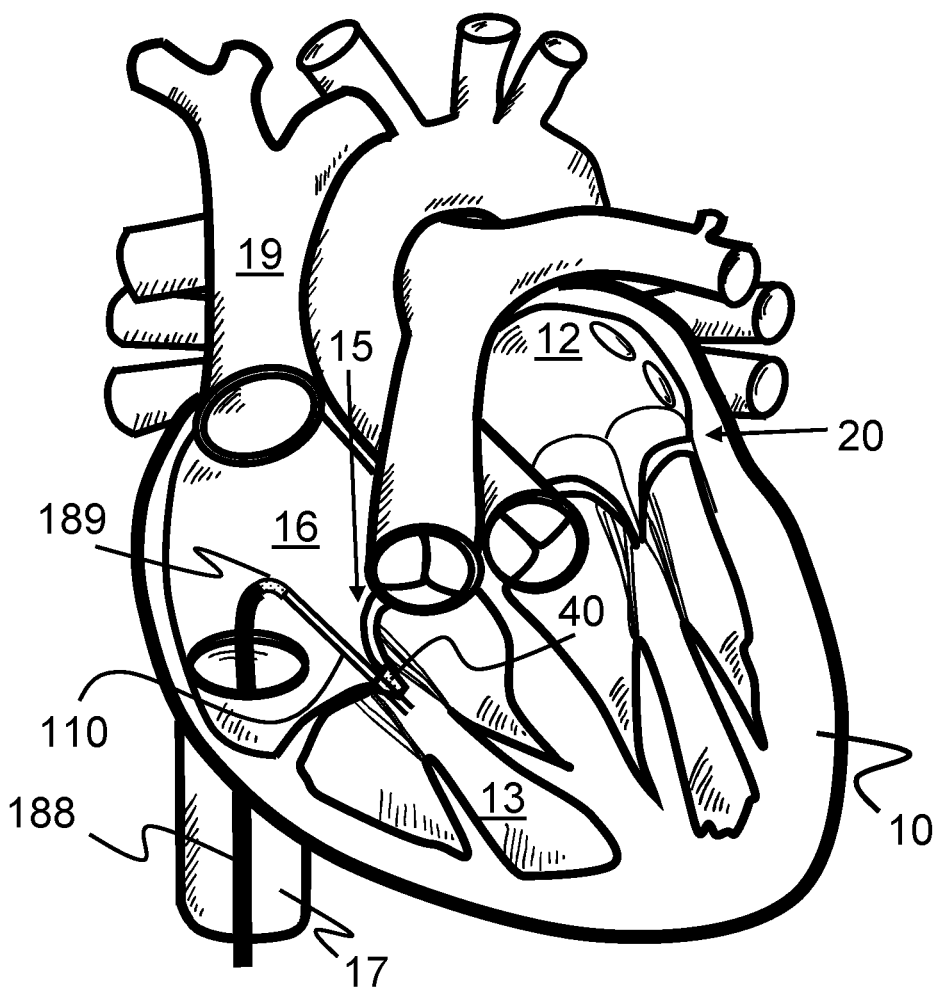
FIG. 68 illustrates a side view of a removal catheter procedure according to the present invention.
Figure 69:
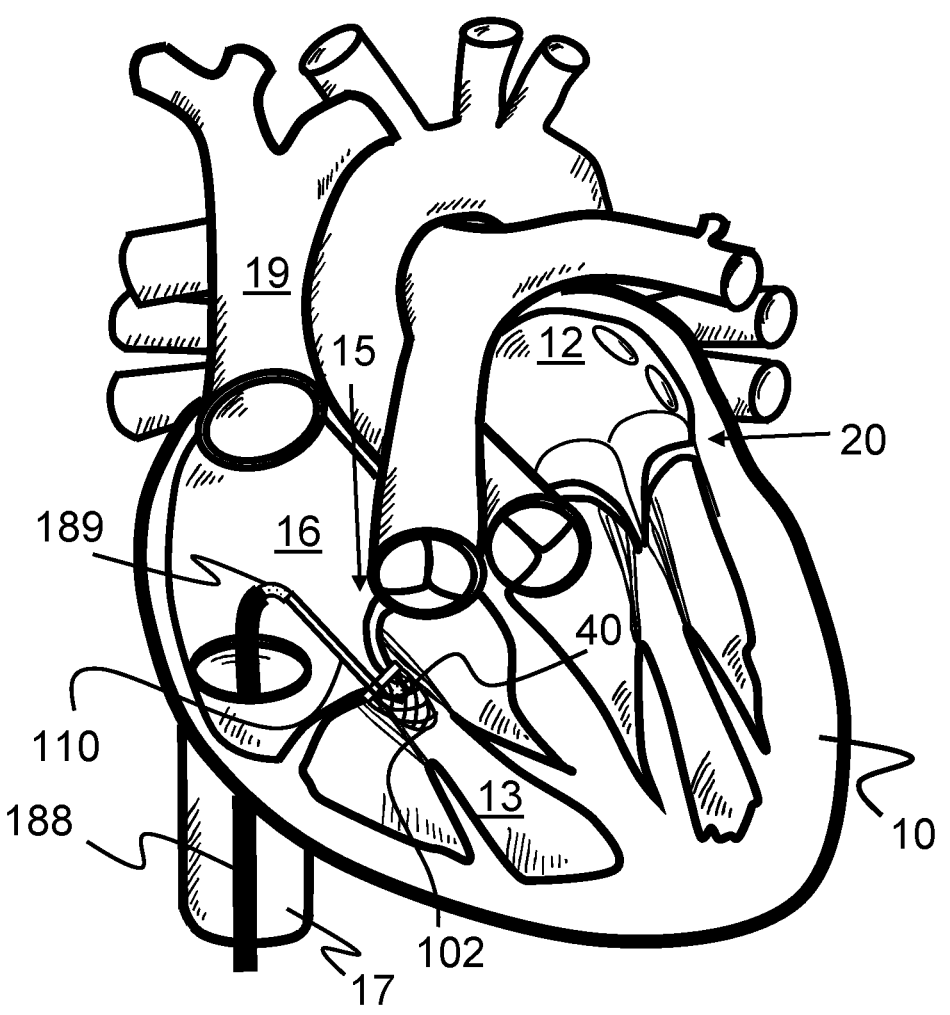
FIG. 69 illustrates a side view of a removal catheter procedure according to the present invention.

The present invention also contemplates using the removal catheter 100 (or any of the variations described in this specification) on the tricuspid valve 15, as seen in FIGS. 68 and 69. Referring first to FIG. 68, an outer tricuspid guide catheter 188 is first delivered to the right atrium 16 by either an approach through the inferior vena cava 17 or the superior vena cava 19. The tricuspid guide catheter 188 may include a fixed curve at its distal end to help its distal opening towards the tricuspid valve 15 or can include steering mechanisms to perform the same. An inner intermediate catheter 189 can then be advanced through the outer tricuspid guide catheter 188 to provide a better angle towards the tricuspid valve 15. For example, the inner intermediate catheter 189 may have a fixed curve towards the tricuspid valve 15 or may include steerable catheter mechanisms to allow the physician to deflect the distal end of the catheter 189 towards the tricuspid valve 15.

Next, the removal catheter 100 is advanced through the inner intermediate catheter 189 so that it passes out of the distal end of the inner intermediate catheter 189, into the right atrium 16, through the tricuspid valve 15, and into the right ventricle 13. Since the leaflet clip 40 is typically positioned in the middle of the valve 15 (e.g., similar to the top view of the mitral valve in FIG. 6), creating to side valve openings, the removal catheter 100 is preferably positioned on either side of the leaflet clip 40.

The inner control member 108 is further distally advanced relative to the outer tubular sheath 110 so that the basket 102 and cutting loop 104 are deployed, expanded, and positioned in the right ventricle 13. The opening of the basket 102 and the opening of the cutting loop 104 are both or oriented so that they face the leaflet clip 40. For example, a plane 103A of the face of the opening of the basket 102 and the opening of the cutting loop 104 may be an angle 103C within a range of about 0 degrees and 90 degrees relative to an axis 103B of the inner control member 108 (e.g., about 45 degrees). The removal catheter 100 is proximally retracted relative to the inner intermediate catheter 189, so that the cutting loop 104 and basket 102 are positioned over and beyond the leaflet clip 40.

The inner control member 108 is proximally retracted, causing the cinching loop 106 and the cutting loop 104 to decrease in diameter, closing the top opening of the basket 102. As the cutting loop 104 decreases in diameter, RF energy is delivered to the loop 104, allowing the uninsulated portion 104 to cut areas of the leaflet tissue adjacent to the leaflet clip 40 and thereby freeing the leaflet clip 40 from the tricuspid valve 15. The basket 102 and leaflet clip 40 can either be retracted through the inner intermediate catheter 189 or all of the catheters can be removed together as a single unit simultaneously.

It should be understood that any of the embodiments of the present specification can be used according to the access and delivery methods described in this application. Additionally, further methods can be used with these access and delivery methods, such as delivery and implantation of an artificial valve (either mitral or tricuspid valve).

While the previously described removal catheter embodiments have included a basket or similar device to capture the heart valve therapy, such as a leaflet clip 40, different capture approaches and devices are also contemplated.

FIGS. 70-72 illustrates a removal catheter 200 for removing a heart valve therapy leaflet clip 40. The removal catheter 200 includes an elongated piercing member 202 that pierces into the device, and an outer cutting catheter 204 that is disposed over the piercing member 202. The elongated piercing member 202 can be a wire, catheter or similar elongated device having a distal end that is sharpened, helically shaped, an expandable barb, or rotational elements, such that the elongated piercing member 202 can be pressed into a top of the leaflet clip 40 (and optionally rotated or expanded) to initially engage or capture the leaflet clip 40, as seen in FIG. 70.

As seen in FIG. 71, the outer cutting catheter 204 is distally advanced over the elongated piercing member 202 until its distal end contacts the top surface of the valve leaflets, as seen in FIG. 71. The outer cutting catheter 204 can be configured to cut the leaflet tissue with a variety of different mechanisms, such as mechanical (e.g., rotation or forward pressure) and/or electrosurgical cutting device (i.e., electrical or cryo). As seen the FIG. 72, once freed from the leaflet tissue, the leaflet clip 40 can be removed by the elongated piercing member 202.

FIGS. 73-75 illustrate a removal catheter 210 that is similar to the previously described catheter 200, except that the cutting catheter 212 also includes a grasping mechanism having to two articulating jaw members connected via a joint (FIG. 76). After the elongated piercing member 202 has engaged the leaflet clip 40 (FIG. 73), the outer cutting member 212 is distally advanced over the elongated piercing member 202 until it contacts the top surface of the leaflets (FIG. 74). The articulating jaw members preferably include tissue cutting mechanisms on their ends, such as blades or electrical/cryo electrosurgical cutting device mechanisms, allowing the leaflet tissue around the leaflet clip 40 to be cut. Finally, in FIG. 75, the jaw members of the cutting catheter 212 are brought towards each other to engage and grasp the tissue clip 40.

FIGS. 77-82 illustrates another embodiment of a removal catheter 220 that embeds in the previously placed leaflet clip 40, followed by passage of a loop-based tool 224 that encapsulates, cuts, and removes the clip 40. In FIG. 77, the loop-based removal catheter 220 includes an anchoring mechanism 226 connected to a central push rod 227, side push rods 223, and pushability elements 225.

FIG. 78 illustrates an end face view of the loop-based removal catheter 220, which may be circular, oval, multi-segmented, or a combination of these shapes and elements. The side rods 223 push on pushability elements 225, while the central push rod 227 applies force to anchoring mechanism 226. In FIG. 79, the entire loop-based removal catheter 220 is folded for placement inside delivery catheter sheath 221. In FIG. 80, the anchoring mechanism 226 is advanced into the heart valve therapy hardware (i.e., leaflet clip 40) using the central push rod 227 and pushability element 125. In FIGS. 78 and 79, the side push rods 223 then are used push on the pushability element 225 to wrap the loop-based removal catheter 220 completely or partially around the leaflet clip 40. Cutting is performed mechanically or electrically followed by removal of the targeted tissue.

Figures 83, 88:
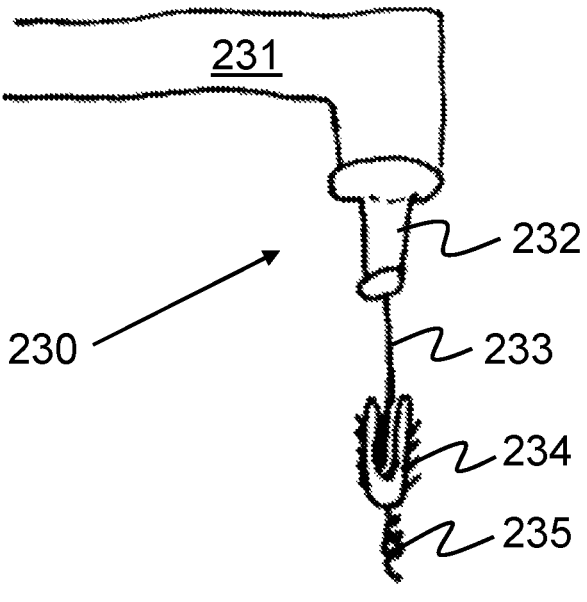
FIG. 83 illustrates a side view of a removal catheter procedure according to the present invention.
FIG. 88 illustrates a side view of a removal catheter procedure according to the present invention.

FIGS. 83-88 illustrate a removal catheter 230 that embeds in the previously placed heart valve therapy (e.g., leaflet clip 40), followed by passage of a tool that expands the leaflet clip 40, followed by removal of the hardware. In FIG. 83, the steerable guide catheter 231 is used to position the removal catheter 232, which contains the expanding tool 234 for expanding the leaflet clip 40. The expanding tool 234 may have barbs, anchors, or embedding mechanisms to remove or grasp native or foreign, leaflet or tissue material from the tissue clip 40. In FIG. 84, an anchor 235 is advanced and implanted. In FIG. 85, the expanding tool 234 is advanced inside the leaflet clip 40. In FIG. 86, the expanding tool 235 is mechanically expanded to expand the leaflet clip 40. The expansion may be aided by electrification, heating, hydraulic means, rotation, internal or external ultrasound or energy. The tissue is cut from the leaflet clip 40. In FIG. 89, the expansion tool 235 is closed and then removed, free from the leaflets. FIG. 88 shows a similar approach with a balloon expandable element 129.

FIGS. 89 and 90 are cross-sectional views of the mitral valve 20 that has been treated with a heart valve therapy comprising one or more chordal structures 50. The chordal structures 50 typically include a chord or strand 52 that is connected to a leaflet via anchors 54 and to the left ventricle. The cord 52 may be anchored on the ventricular side of the leaflet 24 (FIG. 89) or the atrial side of the leaflet 24 (FIG. 90). As further described in the embodiments below, similar device can be used to remove the chordal structures 50 as were used to remove a leaflet clip 40.

FIGS. 91-92 illustrate a removal tool 240 for cutting and capturing previously placed heart valve therapy involving cord or chordal structures implanted into the leaflets. In FIG. 91, the procedure is performed with a previously described cutting catheter 212 with capabilities of opening, closing, electrification, and removal of the hardware, similar to the above description for other heart valve therapy in FIGS. 73-76.

In FIG. 93-97, the procedure is performed with passage of a loop-based tool 250 that encapsulates, cuts, and removes the hardware, similar to the above description of FIGS. 77-82.

In FIGS. 98-100, the procedure is performed with a cutting catheter 260, similar to the above description for other heart valve therapy seen in FIGS. 70-72.

Figure 109:
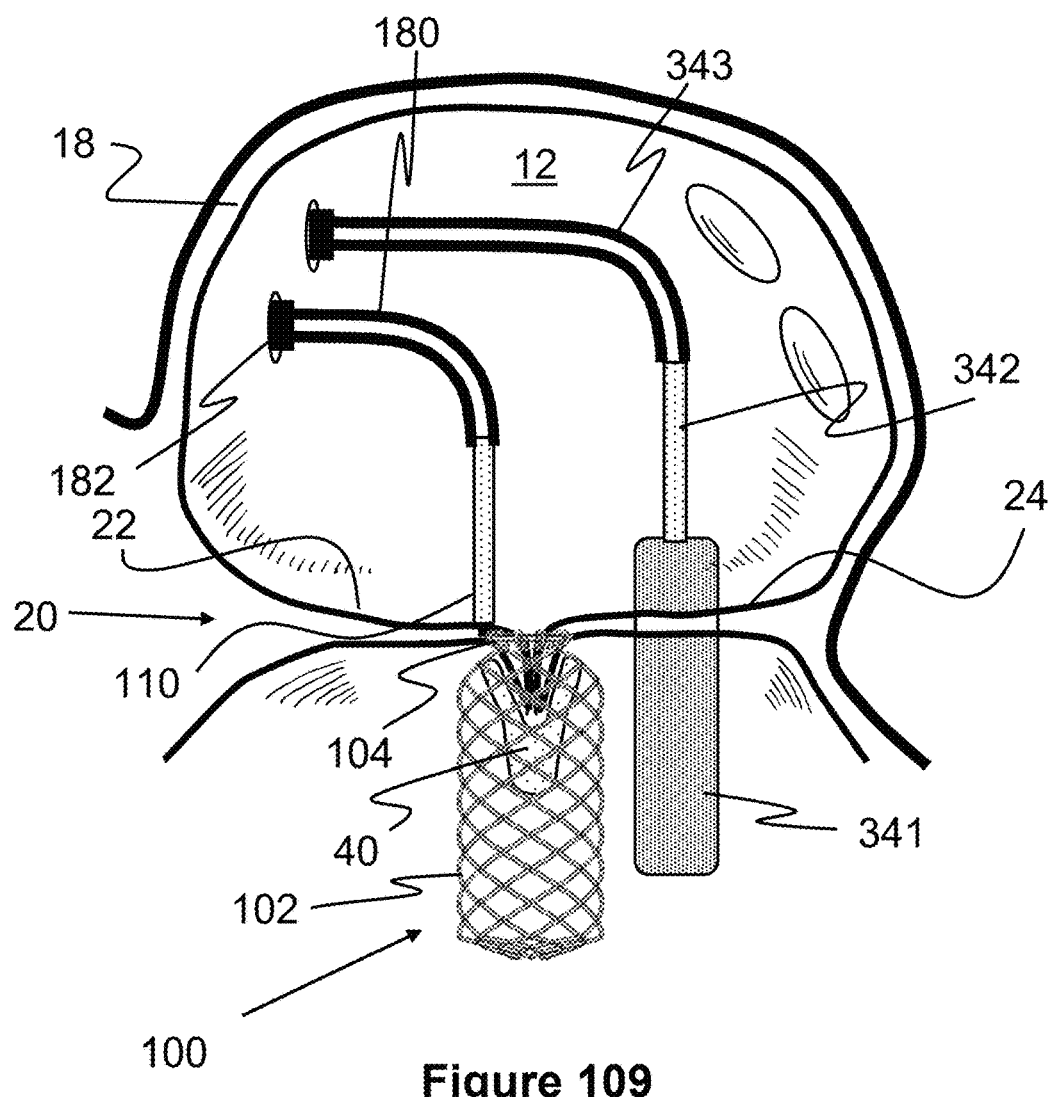
FIG. 109 illustrates a perspective view of a removal catheter apparatus according to the present invention.

Additionally, a flow limiter can be used to help limit flow during any of the procedures described in this specification. For example FIG. 109 illustrates the embodiment of the removal catheter 100 of FIG. 60 with an additional flow limiting device 341. This flow limiting device 341 can be positioned within the region of valve 20 (e.g., through the valve 20) before, during, or after the removal of the clip 40 and is maintained in the valve region to manage the blood flow of the patient by limiting the blood flow. The flow limiting device 341 can be any flow limiter known to those familiar with the art, such as but not limited to, a balloon, a stent with covering, or a catheter. Any or all of these examples being configured to or have the ability to expand to occupy the clinically appropriate space to manage the blood flow by itself or in combination with the valve structure. The flow limiting device 341 can be introduced independently as shown here via delivery catheters 342 and 343. Additionally, the flow limiting device 341 can be integral into the delivery mechanism, such as the inner steerable catheter 180. Alternatively, the flow limiting device 341 can be the delivery system of another therapy such as but not limited to a heart valve.

While different embodiments and examples have been separately discussed in this specification, it is intended that any of the features described can be mixed, swapped, or added to other embodiments in this specification. In other words, each described embodiment is not intended to limit its features and any feature described in any of the other embodiments can be explicitly added to that embodiment.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description should be read to include one or at least one and the singular also includes the plural unless it is obvious that it is meant otherwise.

Still further, the figures depict preferred embodiments for purposes of illustration only. One skilled in the art will readily recognize from the discussion herein that alternative embodiments of the structures and methods illustrated herein may be employed without departing from the principles described herein.

Upon reading this disclosure, those skilled in the art will appreciate still additional alternative structural and functional designs for the customized urn. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A system for removing a heart valve therapy, comprising:

an outer tubular sheath;

a cutting element comprising a first cutting loop connected to a first inner control member and movable from a first compressed configuration within the outer tubular sheath to a second expanded configuration outside of the outer tubular sheath; wherein in the second expanded configuration of the cutting element, a plane aligned across an opening of the first cutting loop is angled between 45 degrees and 135 degrees relative to a longitudinal axis of the first inner control member and wherein the opening of the first cutting loop is positioned asymmetrically to a side of the longitudinal axis of the first inner control member so that the opening of the first cutting loop is rotatable to a plurality of asymmetric locations around the longitudinal axis of the first inner control member; and, a basket connected to a second inner control member and movable from a first compressed configuration within the outer tubular sheath to a second expanded configuration outside of the outer tubular sheath; wherein in the second expanded configuration of the basket, a plane aligned across an opening of the basket is angled between 45 degrees and 135 degrees relative to a longitudinal axis of the second inner control member, the opening of the basket is positioned asymmetrically to a side of the longitudinal axis of the second inner control member so that the opening of the of the basket is rotatable to a plurality of asymmetric locations around the longitudinal axis of the second inner control member, and the opening of the basket opens in a proximal direction.

2. The system of claim 1, wherein the plane of an opening of the first cutting loop is angled at about 90 degrees relative to the longitudinal axis of the first inner control member.

3. The system of claim 1, wherein the plane of an opening of the basket is angled at about 90 degrees relative to the longitudinal axis of the second inner control member.

4. The system of claim 1, wherein the first cutting loop comprises one or more insulated portions and one or more uninsulated portions positioned to contact valve tissue.

5. The system of claim 1, wherein the first cutting loop comprises a single wire composed of a single conductive material, two or more wires that are each composed of a different conductive material, or a wire having a plurality of strands that are composed of different conductive material.

6. The system of claim 1, wherein the first cutting loop has one or more uninsulated portions limited to only a radially inner surface of the second expanded configuration of the cutting element.

7. The system of claim 1, wherein the basket further comprises a plurality of loops positioned around the opening, and a cinch wire positioned through the plurality of loops; wherein moving the cinch wire proximally into the outer tubular sheath closes the opening of the basket.

8. The system of claim 1, wherein the basket further comprises a plurality of loops positioned around the opening of the basket, wherein the cutting element is positioned through the plurality of loops and wherein moving the cutting element proximally into the outer tubular sheath closes the opening of the basket.

9. The system of claim 1, further comprising a steerable inner catheter having a passage sized to accommodate passage of the outer tubular sheath, and an outer guide catheter having a passage sized to accommodate passage of the steerable inner catheter.

10. The system of claim 1, wherein the cutting element further comprises a second cutting loop.

11. The system of claim 10, wherein the second cutting loop is connected to a third inner control member movable within the outer tubular sheath.

12. The system of claim 1, wherein the first cutting loop is circular, oval, or saddle shaped.

13. The system of claim 1, wherein the basket is composed of a plurality of braided wires, each of which is composed of a shape memory material.

14. The system of claim 13, wherein the plurality of braided wires have an electrically insulating coating on their outer surface.

15. The system of claim 1, wherein the basket is composed of silicone, PET, polyester, nylon, polypropylene, or Kevlar.

16. The system of claim 1, wherein the basket is composed of a polymer in a braid, mesh, weave, knit, or injection molded shape.

17. The system of claim 1, wherein the basket is composed of a laser-cut metal having a plurality of pores.

18. The system of claim 1, wherein the first cutting loop has side portions that form a saddle shape.

19. The system of claim 18, wherein the side portions dip downward and upward in a wave shape.

20. The system of claim 1, wherein the first cutting loop comprises a plurality of uninsulated regions that can be electrically activated individually at different times or all together at a same time.

21. The system of claim 1, wherein the first cutting loop is electrically isolated from the basket.

22. The system of claim 21, wherein the basket further comprises a cinching loop to close a top of the basket and the first cutting loop is also electrically isolated from the cinching loop.

23. A system for removing a heart valve therapy, comprising:
an outer tubular sheath;
a cutting element comprising a first cutting loop connected to a first inner control member and movable from a first compressed configuration within the outer tubular sheath to a second expanded configuration outside of the outer tubular sheath; wherein in the second expanded configuration of the cutting element, a plane aligned across an opening of the first cutting loop is angled between 45 degrees and 135 degrees relative to a longitudinal axis of the first inner control member and the opening of the first cutting loop is completely positioned to a side of the longitudinal axis of the first inner control member and is rotatable to a plurality of different positions around the longitudinal axis of the first inner control member; and, a basket connected to the first inner control member and movable from a first compressed configuration within the outer tubular sheath to a second expanded configuration outside of the outer tubular sheath; wherein in the second expanded configuration of the basket, a plane aligned across an opening of the basket is angled between 45 degrees and 135 degrees relative to the longitudinal axis of the first inner control member and the opening of the basket is positioned completely to a side of the longitudinal axis of the first second inner control member and opens in a proximal direction and is rotatable to a plurality of different positions around the longitudinal axis of the second inner control member.

24. A method of treating a heart valve, comprising:
positioning a steerable guide catheter transeptally into a left atrium of a heart;
positioning a first cutting loop connected to a first inner control member outside of an outer tubular sheath and into a left ventricle of a heart so that a plane of an opening of the first cutting loop is angled between 45 degrees and 135 degrees relative to an axis of the first inner control member and the first cutting loop is positioned to a side of the axis of the first inner control member;
moving the first cutting loop so that a heart valve therapy connected to mitral valve leaflets passes through the first cutting loop;
electrically activating the first cutting loop and cutting tissue to free the heart valve therapy; and,
capturing the heart valve therapy within a receptacle and removing the heart valve therapy from the heart.

25. The method of claim 24, further comprising decreasing a diameter of an opening of the receptacle.

26. The method of claim 25, wherein activating the first cutting loop further comprises delivering radio frequency current to one or more electrodes of the first cutting loop.

27. The method of claim 25, wherein positioning the first cutting loop connected to the first inner control member so that the plane of the opening of the first cutting loop is angled between 45 degrees and 135 degrees relative to the axis of the first inner control member further comprises positioning the first cutting loop so that the plane of the opening of the first cutting loop is about 90 degrees relative to the axis of the first inner control member.

28. The method of claim 25, wherein electrically activating the first cutting loop includes closing the opening of the first cutting loop around the tissue.

29. The method of claim 25, wherein the first cutting loop comprises a wave shape in which side portions of the first cutting loop form a dip.

30. The method of claim 29, wherein the first cutting loop comprises one or more insulated portions and wherein the first cutting loop comprises one or more uninsulated portions at a distal region of the first cutting loop.

31. The method of claim 25, further comprising positioning a second loop within the left ventricle of the heart.

32. The method of claim 31, wherein the first cutting loop is activated independently of the second loop.

\* \* \* \* \*